US009084754B2

(12) United States Patent
Buyuktimkin et al.

(10) Patent No.: US 9,084,754 B2
(45) Date of Patent: Jul. 21, 2015

(54) HIGHLY PERMEATING TERBINAFINE FORMULATION

(75) Inventors: Servet Buyuktimkin, San Diego, CA (US); Nadir Buyuktimkin, San Diego, CA (US); Jagat Singh, Toronto (CA); John M. Newsam, La Jolla, CA (US); Dominic King-Smith, San Diego, CA (US); Edward Kisak, San Diego, CA (US)

(73) Assignee: NUVO RESEARCH INC., Mississauga (CA)

( * ) Notice: Subject to any disclaimer, the term of this patent is extended or adjusted under 35 U.S.C. 154(b) by 76 days.

(21) Appl. No.: 13/525,108

(22) Filed: Jun. 15, 2012

(65) Prior Publication Data

US 2012/0309843 A1    Dec. 6, 2012

Related U.S. Application Data

(63) Continuation of application No. PCT/US2010/061940, filed on Dec. 22, 2010.

(60) Provisional application No. 61/289,967, filed on Dec. 23, 2009, provisional application No. 61/289,962, filed on Dec. 23, 2009.

(51) Int. Cl.
| | |
|---|---|
| *A01N 33/02* | (2006.01) |
| *A01N 33/24* | (2006.01) |
| *A61K 31/13* | (2006.01) |
| *A61K 31/135* | (2006.01) |
| *A61K 31/137* | (2006.01) |
| *A61K 9/00* | (2006.01) |
| *A61K 47/10* | (2006.01) |
| *A61K 47/12* | (2006.01) |
| *A61K 47/18* | (2006.01) |
| *A61K 47/20* | (2006.01) |
| *A61K 47/34* | (2006.01) |
| *A61K 47/38* | (2006.01) |

(52) U.S. Cl.
CPC .............. *A61K 31/137* (2013.01); *A61K 9/0017* (2013.01); *A61K 47/10* (2013.01); *A61K 47/12* (2013.01); *A61K 47/18* (2013.01); *A61K 47/186* (2013.01); *A61K 47/20* (2013.01); *A61K 47/34* (2013.01); *A61K 47/38* (2013.01)

(58) Field of Classification Search
None
See application file for complete search history.

(56) References Cited

U.S. PATENT DOCUMENTS

| 4,529,601 A | 7/1985 | Broberg et al. |
| 6,368,618 B1 | 4/2002 | Jun et al. |
| 6,841,161 B1 | 1/2005 | Passmore et al. |
| 7,138,394 B2 | 11/2006 | Schwarz et al. |
| 7,462,362 B2 | 12/2008 | Kepka et al. |
| 2003/0091666 A1* | 5/2003 | Murad .......................... 424/765 |
| 2004/0022831 A1* | 2/2004 | Mailland ....................... 424/443 |
| 2005/0075407 A1 | 4/2005 | Tamarkin et al. |
| 2005/0158348 A1 | 7/2005 | Schwarz et al. |
| 2006/0078599 A1 | 4/2006 | Ebmeier et al. |
| 2007/0224261 A1 | 9/2007 | Draper |
| 2008/0261986 A1* | 10/2008 | Friden et al. ............... 514/239.5 |

FOREIGN PATENT DOCUMENTS

| CA | 2 500 907 A1 | 9/2006 |
| EP | 0197076 A1 | 10/1986 |
| EP | 0503988 A1 | 9/1992 |
| WO | WO9953913 * | 10/1999 |
| WO | 03/020250 A1 | 3/2003 |
| WO | WO 2005/018530 A2 | 3/2005 |
| WO | WO 2006/042059 A1 | 4/2006 |
| WO | WO 2006/096955 A1 | 9/2006 |
| WO | WO 2006/131721 A2 | 12/2006 |
| WO | WO 2004/084826 A2 | 10/2007 |
| WO | 2007/147052 A2 | 12/2007 |
| WO | 2010/010470 A2 | 1/2010 |
| WO | WO 2011/014850 A2 | 2/2011 |

OTHER PUBLICATIONS

Barry et al., "Novel mechanisms and devices to enable successful transdermal drug delivery," European Journal of Pharmaceutical Sciences, 2001, vol. 14, pp. 101-114.
Bennett, John E., "Antimicrobial Agents, Antifungal Agents," Goodman & Gilman's The Pharmacological Basis of Therapeutics, 11/E, McGraw-Hill, Brunton, L.L., Ed., 2006, Chapter 48, pp. 1225-1241.
Benson, "Transdermal Drug Delivery: Penetration Enhancement Techniques," Curr. Drug Del. 2005, vol. 2, pp. 23-33.
Blumberg, M., "Onychomycosis," http://www.emedicine.com/derm/topic300.htm, accessed Jul. 7, 2008.
Casciano, J. et al., "Economic Analysis of Oral and Topical Therapies For-Onychomycosis of the Toenails and Fingernails," *Manag. Care* 2003, 12(3), 47-54.
Dhamecha et al., "Drug Vehicle Based Approaches of Penetration Enhancement," Intl. J. of Pharmacy and Pharmaceutical Sciences, 2009, vol. 1, Issue 1, pp. 24-46.

(Continued)

*Primary Examiner* — Anoop Singh
*Assistant Examiner* — Doan Phan
(74) *Attorney, Agent, or Firm* — Kilpatrick Townsend & Stockton LLP

(57) ABSTRACT

The present invention provides topical compositions, methods of preparation, and methods of treatment for onychomycosis. In certain specific embodiments, the invention provides an anti-fungal pharmaceutical composition for topical application comprising an anti-fungal agent, a zwitterionic surfactant or charged derivative thereof; a carboxylic acid, a lower alcohol, and water. The acid is selected from a short-chain hydroxy acid, a short-chain fatty acid, and a mixture thereof. In certain other specific embodiments, the invention provides an anti-fungal pharmaceutical composition for topical application comprising an anti-fungal agent, a quarternary amino acid, a keratolytic agent; a lower alcohol; and water. In certain embodiments, the keratolytic agent is urea, ammonium thioglycolate, or a mixture thereof.

40 Claims, 49 Drawing Sheets

(56) References Cited

OTHER PUBLICATIONS

Finlay, A.Y., "Pharmacokinetics of terbinafine in the nail," *Br J Dermatol*. 1992, 126 Suppl. 39:28-32.

Lamisil® package information, http://www.accessdata.fda.gov/drugsatfda_docs/label/2007/020980s005lbl.pdf, accessed Jul. 30, 2010, 2 pp.

Penlac® Nail Lacquer "Prescribing Information," http://products.sanofi-aventis.us/penlac/penlac.html, accessed Aug. 18, 2008, pp. 1-18.

Remington: *The Science and Practice of Pharmacy*, Nineteenth Edition, pp. 878-879, 1995.

Shaw et al. "The peripheral circulatory effects of clonidine and their role in the production of arterial hypotension," European Journal of Pharmacology, 1971, vol. 14, pp. 101-111.

Sigurgeirsson et al.. "Long-term Effectiveness of Treatment with Terbinafine vs. Itraconazole in Onychomycosis, *A 5-Year Blinded Prospective Follow-up Study*," Arch. Dermatol., 2002, vol. 138, pp. 353-357.

Tosti, A. et al., "Relapses of onychomycosis after successful treatment with systemic antifungals: A three-year follow-up," *Dermatology* 1998, 197(2), 162-166.

International Search Report mailed Jun. 6, 2011 for Application No. PCT/US2010/061940, 14 pages.

International Search Report mailed Sep. 29, 2011 for Application No. PCT/US2010/044036, 5 pages.

\* cited by examiner

Comparison of Terbinafine Content for F142 at 25°C and 40°C

Study I:

Study II:

1 nail ~ 50 mg

HIGHLY PERMEATING TERBINAFINE FORMULATION

CROSS-REFERENCES TO RELATED APPLICATIONS

This application is a continuation of International Patent Application No. PCT/US10/61940 (filed Dec. 22, 2010), which claims the benefit of U.S. Provisional Patent Application Nos. 61/289,962 and 61/289,967 (both filed Dec. 23, 2009). The disclosure of all priority applications is hereby incorporated by reference in its entirety for all purposes.

BACKGROUND OF THE INVENTION

Onychomycosis is a fungal infection that affects the toenails (~80% of cases) and the fingernails (~20% of cases). The most common causative pathogens of onychomycosis are the dermatophytes *Trichophyton rubrum* and *Trichophyton interdigitale* (also known as *Trichophyton mentagrophytes*). These pathogens represent the cause of roughly 70% and 20% of onychomycosis cases, respectively. Other causative agents include dermatophytes such as *Epidermophyton floccosum, Trichophyton violaceum, Microsporum gypseum, Trichophyton tonsurans, Trichophyton soudanense, Trichophyton verrucosum*, nondermatophyte fungi such as *Neoscytalidium* (also known as *Scytalidium*), *Scopulariopsis, Aspergillus, Fusarium, Acremonium*, and yeasts such as *Candida*. The infection may involve any component of the nail unit, including the nail matrix, the nail bed or the nail plate. See Blumberg, M. "Onychomycosis," http://www.emedicine.com/derm/topic300.htm, accessed Jul. 7, 2008.

Distal lateral subungual onychomycosis is the most common form of infection. In this variant, the infection begins around the edges of the nail and can cause inflammation in these areas while concurrently spreading to the underside of the nail. The result is disfigurement of the nail and potentially some pain, discomfort and transmission of infection to other nails. If left untreated, onychomycosis can result in permanent nail deformity.

Onychomycosis is a very difficult condition to cure. Today, it is commonly treated with an antifungal medication that is delivered to the systemic circulation, in spite of the fact that the onychomycosis infection is localized to the nail structure. This can result in serious and unwanted side effects, including gastrointestinal symptoms, liver abnormalities, rashes, taste disturbances, hypertension, and drug-drug interactions with a wide range of other medications.

Topical drugs for the treatment of onychomycosis are available, but they are not very effective in the treatment of the disease. For example, Penlac® (ciclopirox 8% solution) is a topical treatment which has been approved in the United States for the treatment in immunocompetent patients with mild to moderate onychomycosis of fingernails and toenails without lunula involvement, due to *Trichophyton rubrum*. However, the drug is not very effective in the treatment of onychomycosis, providing complete cure (defined as clear nail and negative mycology) in less than 10% of the intent-to-treat population in the Phase III studies used to obtain approval in the United States. Further, relapse appears to be a significant issue with this drug. See Casciano J. et al. *Manag. Care* 2003, 12(3), 47-54; Tosti, A. et al. *Dermatology* 1998, 197(2), 162-166; Sigurgeirsson, B. et al. *Arch. Dermatol.* 2002, 138(3), 353-7; and Penlac® prescribing information, http://products.sanofi-aventis.us/penlac/penlac.html, accessed May 19, 2008.

One of the leading anti-fungal agents for oral treatment of onychomycosis is the drug terbinafine. Terbinafine has also been approved by the US Food and Drug Administration in cream, gel, solution and spray dosage forms for use in topical treatment of fungal infections. However, these products are not approved for the treatment of onychomycosis. For example, terbinafine hydrochloride cream 1% (tradename Lamisil®) is available as an over-the-counter product, and the label specifically notes that the product should not be used on nails. (For package information, see http://www.accessdata.fda.gov/drugsatfda_docs/label/2007/020980s0051b1.pdf, accessed Jul. 30, 2010.)

There is a strong need for a new topical drug composition that can provide good efficacy in treating onychomycosis while avoiding the systemic side effects of oral treatments. The present invention satisfies these and other needs.

BRIEF SUMMARY OF THE INVENTION

The present invention provides topical drug compositions that are efficacious in treating onychomycosis while avoiding systemic side effects. As such, in one embodiment, the present invention provides a topical formulation for the treatment of onychomycosis, comprising, consisting essentially of, or consisting of:
  terbinafine or a salt thereof;
  a zwitterionic surfactant or a charged derivative thereof;
  an acid, which is a member selected from the group consisting of a short-chain hydroxy acid, a short-chain fatty acid, and a mixture thereof;
  a lower alcohol; and
  water.

In certain aspects, the inclusion of a keratolytic agent (e.g., urea) is particularly advantageous as it increases the penetration of the antifungal agent through the nail.

In certain aspects, the inclusion of a terpene (e.g., menthol) is particularly advantageous as it increases the penetration of the antifungal agent through the nail.

In certain aspects, the inclusion of a second lower alcohol (e.g., a polyol; a diol or triol, such as hexanetriol) is particularly advantageous as it increases the penetration of the antifungal agent through the nail.

In certain aspects, the inclusion of panthenol is particularly advantageous as it increases the penetration of the antifungal agent through the nail.

In another embodiment, the present invention provides a topical formulation for the treatment of onychomycosis, comprising, consisting essentially of, or consisting of:
  terbinafine or a salt thereof;
  a zwitterionic surfactant or a charged derivative thereof;
  an acid, which is a member selected from the group consisting of a short-chain hydroxy acid, a short-chain fatty acid, and a mixture thereof;
  a keratolytic agent;
  a terpene;
  panthenol, optionally D-panthenol;
  a lower alcohol; and
  water.

In certain aspects, the formulation can be applied to the nail exterior for transungual delivery of the antifungal agent and has superior balance between permeation and retention.

In yet another embodiment, the present invention provides a topical formulation for the treatment of onychomycosis, comprising, consisting essentially of, or consisting of:
  an antifungal agent such as terbinafine or a salt thereof;
  a quarternary amino acid;
  a keratolytic agent;

a lower alcohol; and water.

In certain aspects, the combination of an antifungal agent and a keratolytic agent is particularly advantageous as it increases the penetration of the antifungal agent through the nail.

In still another embodiment, the present invention provide a topical formulation for the treatment of onychomycosis, comprising, consisting essentially of, or consisting of:

an antifungal agent such as terbinafine or a salt thereof;

a keratolytic agent;

a short-chain detergent;

a lower alcohol; and water.

In certain aspects, the formulation can be applied to the nail exterior for transungual delivery of the antifungal agent and has superior balance between permeation and retention.

In another embodiment, the present invention provides a method for treating onychomycosis by administering a composition described herein.

In still yet another embodiment, the present invention provides a use of a composition described herein in the manufacture of a medicament for treating onychomycosis.

These and other aspects, objects, and advantages will become more apparent when read with the following detailed description and drawings.

BRIEF DESCRIPTION OF THE DRAWINGS

The embodiments of the application will now be described in greater detail with reference to the attached drawings in which:

FIG. 1A shows the permeation of active ingredient through shed snakeskin at 4, 24, and 48 hr. FIG. 1B shows the total snakeskin retention of the active ingredient.

FIG. 2A shows the permeation of active ingredient through shed snakeskin at 4, 24, and 48 hr. FIG. 2B shows the total snakeskin retention of the active ingredient.

FIG. 3A shows the permeation of the active ingredient through shed snakeskin at 4, 24, and 48 hr. FIG. 3B shows the total snakeskin retention of the active ingredient.

FIG. 4A shows the permeation of active ingredient through shed snakeskin at 3.5, 24, and 48 hr. FIG. 4B shows the total snakeskin retention of the active ingredient.

FIG. 5 shows the permeation of active ingredient through bovine hoof at 44, 92, and 144 hr.

FIG. 6A shows the permeation of active ingredient through shed snakeskin at 4, 21, and 26 hr. FIG. 6B shows the total snakeskin retention of the active ingredient.

FIG. 7A shows the total snakeskin retention of the active ingredient through shed snakeskin at 4, 20, and 24 hr. FIG. 7B shows the total snakeskin retention of the active ingredient.

FIG. 8A shows the permeation of active ingredient through shed snakeskin at 4 and 21 hr. FIG. 8B shows the total snakeskin retention of the active ingredient.

FIG. 9 shows the permeation of active ingredient through shed snakeskin at 4, 20, and 24 hr.

FIG. 10A shows the total snakeskin retention of the active ingredient through shed snakeskin at 4, 21, and 24 hr. FIG. 10B shows the total snakeskin retention of the active ingredient.

FIG. 12 shows the permeation of the active ingredient through bovine hoof at 44, 92, and 144 hr.

FIG. 13A shows the permeation of active ingredient through bovine hoof at 66, 114, 162, 234, 282, or 330 hr. FIG. 13B shows the total bovine hoof retention of the active ingredient.

FIG. 14A shows the permeation of active ingredient through bovine hoof at 67, 115, 163, 235, or 307 hr. FIG. 14B shows the total bovine hoof retention of the active ingredient.

FIG. 15A shows the permeation of active ingredient through bovine hoof at 95, 143, 215, 263, 311, and 383 hr. FIG. 15B shows the total bovine hoof retention of the active ingredient.

FIG. 17A shows the results of F132 and F133 (Table 21). FIG. 17B shows the results of F141 (Table 23).

FIG. 18A shows permeation results for twice-daily (BID) application of F141 (Table 24). FIG. 18B shows a comparison of F131 and F141 (Table 25).

FIG. 19A shows cadaver nail permeation results for F143 (Table 26). FIG. 19B shows a comparison of F141 and F143 with F40 (Control 2) (Table 27).

FIG. 22A shows permeation results for F141 and F143 (Table 33). FIG. 22B shows shed snakeskin permeation results for F141, F142, and F143 (Table 34).

FIG. 23A shows shed snakeskin permeation results for F131, F132, and F133 (Table 35). FIG. 23B shows cadaver nail permeation results for F141, F142, and F143 (Table 36).

FIG. 24A illustrate the results for F131 (Table 37, 39, and 40); FIG. 24B, for F141 (Tables 38, 41, and 42).

FIG. 26A shows the permeation of active ingredient over time. FIG. 26B shows the total amount of active ingredient as a snakeskin retention value.

FIG. 27A shows the permeation of active ingredient over time. FIG. 27B shows the total amount of active ingredient as a snakeskin retention value.

FIG. 28A shows the permeation of active ingredient over time. FIG. 28B shows the total amount of active ingredient as a snakeskin retention value.

FIG. 29 shows the permeation of active ingredient over time.

FIG. 30A shows the permeation of active ingredient over time. FIG. 30B shows the total amount of active ingredient as a bovine hoof retention value.

FIG. 31A shows the total amount of active ingredient as a bovine hoof retention value. FIG. 31B shows the permeation of active ingredient over time.

FIG. 32A shows the total amount of active ingredient as a snakeskin retention value. FIG. 32B shows the permeation of active ingredient over time.

FIG. 33A shows the total amount of active ingredient as a bovine hoof retention value. FIG. 33B shows the permeation of active ingredient over time.

FIG. 34 shows the permeation of active ingredient over time.

FIG. 35A shows the total amount of active ingredient as a snakeskin retention value. FIG. 35B shows the permeation of active ingredient over time.

FIG. 35A shows the permeation of active ingredient over time. FIG. 35B shows the total amount of active ingredient as a snakeskin retention value.

FIG. 37A shows the permeation of active ingredient over time. FIG. 37B shows the total amount of active ingredient as a snakeskin retention value.

FIG. 38A shows the permeation of active ingredient over time. FIG. 38B shows the total amount of active ingredient as a snakeskin retention value.

FIG. 39A shows the permeation of active ingredient over time. FIG. 39B shows the total amount of active ingredient as a snakeskin retention value.

FIG. 40A shows the permeation of active ingredient over time. FIG. 40B shows the total amount of active ingredient as a snakeskin retention value.

FIG. 41A shows the permeation of active ingredient over time. FIG. 41B shows the total amount of active ingredient as a snakeskin retention value.

FIG. 42A shows the permeation of active ingredient over time. FIG. 42B shows the total amount of active ingredient as a snakeskin retention value.

FIG. 43 shows the permeation of active ingredient over time.

FIG. 44A shows the total amount of active ingredient as a snakeskin retention value. FIG. 44B shows the permeation of active ingredient over time.

FIG. 45 shows the permeation of active ingredient over time.

FIGS. 46A-B show the permeation of active ingredient over time versus a prior art formulation (Control 1).

FIG. 47A shows the permeation of active ingredient over time with finite dose. FIG. 47C shows the total amount of active ingredient as a human cadaver nail retention value. FIG. 47B shows the permeation of active ingredient over time with infinite dose. FIG. 47D shows the total amount of active ingredient as a human cadaver nail retention value.

FIG. 48A shows the total amount of active ingredient as a human cadaver retention value; FIG. 48B shows the permeation of active ingredient over time versus a prior art formulation (Control 2).

FIG. 49A shows the total amount of active ingredient as a snakeskin retention value; FIG. 49B shows the permeation of active ingredient over time.

DETAILED DESCRIPTION OF THE INVENTION

I. Definitions

Figure 1A:
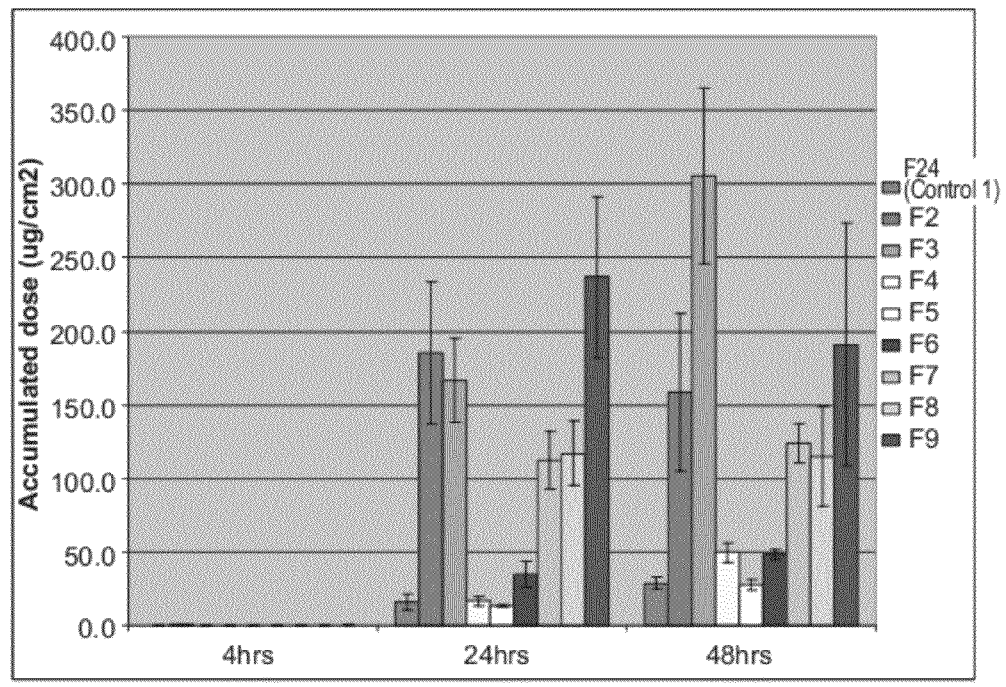
FIGS. 1A and 1B illustrate the results of shed snakeskin permeation studies on the formulations of Table 1.

The terms "a," "an," or "the" as used herein not only include aspects with one member, but also include aspects with more than one member. For example, an embodiment including "an anti-fungal agent and a zwitterionic surfactant" should be understood to present certain aspects with two or more antifungal agents, two or more zwitterionic surfactants, or both.

"About" as used herein applies to a defined range around a numerical value. When "X" is a numerical value, "about X,"

generally indicates a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to imply and provide written description support for a claim limitation of, e.g., "0.98X." However, when the quantity measured in "X" only includes whole integer values (e.g., "X carbons"), "about X" indicates from (X−1) to (X+1). In this case, "about X" as used herein specifically indicates at least the values X, X−1, and X+1. When "about" is applied to the beginning of a numerical range, it applies to both ends of the range. Thus, "from about 5 to 20%" is equivalent to "from about 5% to about 20%" (and vice versa). When "about" is applied to the first value of a set of values, it applies to all values in that set. Thus, "about 7, 9, or 11%" is equivalent to "about 7%, about 9%, or about 11%."

"Anti-fungal agent" as used herein includes a compound that has the ability to kill, to stop the growth, or to slow the growth of a fungus in vitro or in vivo as well as a compound that can prevent or alleviate a fungal infection in vitro or in vivo. Representative anti-fungal agents include allylamine anti-fungal agents such as terbinafine, amorolfine, naftifine, butenafine, and the like; pharmaceutically acceptable salts thereof; and mixtures of the compounds or salts thereof.

"Cellulosic thickening agent" as used herein includes a thickening agent that is 1) a natural or synthetic polymeric carbohydrate (e.g., cellulose, pharmaceutically acceptable vegetable gums); 2) a polymeric or oligomeric derivative of a polymeric carbohydrate that is produced by chemical modification (e.g., hydroxypropyl cellulose, hydroxypropyl methyl cellulose, hydroxyethyl cellulose); or 3) mixtures thereof. Representative cellulosic thickening agents include cellulose, hydroxypropyl cellulose ("HPC"), hydroxypropyl methyl cellulose, hydroxyethyl cellulose, methyl cellulose, carboxymethyl cellulose, and the like.

In general, "detergent" is used interchangeably with "surfactant." "Short-chain detergent" as used herein includes molecules comprising 1 to about 10 carbon atoms and functioning as a surfactant.

In general, embodiments described herein that include chiral compounds (e.g., lactic acid) may include embodiments with the racemic form or embodiments enriched in the D- or L-enantiomer thereof (up to and including essentially pure D-lactic acid or L-lactic acid).

"Film-forming agent" as used herein generally includes an agent or combination of agents that assists in the formation of a continuous layer covering a surface. A film-forming agent may be a pure substance, or it may comprise, consist essentially of, or consist of a mixture of different chemical entities. Exemplary film-forming agents include polyacrylates, polyacrylamides, polyvinylpyrrolidones, carbomer polymers (e.g., polymers comprising poly(methyl methacrylate)), carbomer derivatives (e.g., polymers comprising amide or ester derivatives of poly(methyl methacrylate)), and the like, as well as mixtures thereof.

"Finite dosing" as used herein generally includes an application of a limited reservoir of an active agent. The active agent in the reservoir is depleted with time, leading to a tapering off of the absorption rate of the active agent after a maximum absorption rate is reached.

"Infinite dosing" as used herein generally includes an application of a large reservoir of an active agent. The active agent in the reservoir is not significantly depleted with time, thereby providing a long-term, continuous steady-state of active absorption.

"Lower alkanol" as used herein includes straight- or branched-chain alkyl alcohols of 1 to about 6 carbon atoms. Representative lower alkanols include methanol, ethanol, n-propanol, isopropanol, n-butanol, i-butanol, t-butanol, n-pentanol, i-pentanol, 3-pentanol, and the like.

"Penetration enhancer," "molecular penetration enhancer," or "MPE™" as used interchangeably herein includes an agent or a combination of agents that improves the transport of molecules such as a pharmaceutically or cosmetically active agent into or through a natural membrane, such as skin or nail. Various conditions may occur at different sites in the body, either in the skin or below the skin, creating a need to target delivery of compounds. For example, in a treatment for onychomycosis, delivery of the active agent to the tissue underlying or surrounding the nail may be necessary to achieve therapeutic benefit. An MPE™ may be used to assist in the delivery of an active agent i) directly into the skin, or nail; ii) locally, or regionally, into tissue(s) underlying or near to the skin or nail; or iii) indirectly via systemic distribution to the site of the disease. If systemic distribution of an active agent (e.g., terbinafine) would be likely to produce side effects, an MPE™ is preferably selected to maximize direct delivery and to minimize systemic distribution. An MPE™ may be a pure substance or may comprise, consist essentially of, or consist of a mixture of different chemical entities.

Generally, when a percentage range is taught, it incorporates all full or partial percentages in between (i.e., within the bounds of the range). For example, a percentage range of 15 to 25% would also teach inter alia the specific values of 17.36% and 21%. A percentage range of about 13 to 17% would also teach inter alia the specific values of 12.97%, 16%, and 17.1%.

Where a formulation is not aqueous, the term "pH", as used herein, refers to the apparent pH of the formulation as determined by methods standard in the art.

"Short-chain acid" as used herein includes molecules comprising 1 to about 10 carbon atoms and including at least one carboxylic acid functional group. Examples include lactic acid, glycolic acid, citric acid, malic acid, caproic acid, and caprylic acid.

"Thickening agent" as used herein includes an agent or combination of agents that increases the viscosity of a composition. A thickening agent may be a pure substance, or it may comprise, consist essentially of, or consist of a mixture of different chemical entities. Exemplary thickening agents include cellulose polymers, carbomer polymers, carbomer derivatives, cellulose derivatives, polyvinyl alcohol, poloxamers, polysaccharides, and the like, as well as mixtures thereof.

"Topical application" as used herein includes the administration of a composition (e.g., a formulation containing a pharmaceutically or cosmetically active agent) to the skin, nail, mucosa, or other localized region of the body. Topical application may result in the delivery of an active agent to the skin, the nail plate, the nail bed, a localized region of the body, a localized volume of the body, or the systemic circulation.

"Topical formulation" as used herein includes a formulation that is suitable for topical application to the skin, a nail, or a mucosa. A topical formulation may, for example, be used to confer a therapeutic or cosmetic benefit to its user. Topical formulations can be used for topical, local, regional, transdermal, or transungual application of substances.

"Transdermal" as used herein includes a process that occurs through the skin. The terms "transdermal," "percutaneous," and "transcutaneous" can be used interchangeably. In certain embodiments, "transdermal" may also include epicutaneous.

"Transdermal application" as used herein includes administration through the skin. Transdermal application can be used for systemic delivery of an active agent; however, it is also useful for delivery of an active agent to tissues underlying the skin with minimal systemic absorption. In certain embodiments, "transdermal application" may also include epicutaneous application.

"Transungual" as used herein includes a process that occurs through the nail.

"Transungual application" as used herein includes administration to or through a nail. Transungual application can be used for systemic delivery of an active agent. However, it is preferably used for delivery of an active agent to the nail or to tissues underlying or surrounding the nail with minimal systemic absorption.

"Treatment" as used herein includes any cure, amelioration, or prevention of a disease in a mammal, particularly a human. Treatment may prevent the disease from occurring; inhibit the disease's spread; relieve the disease's symptoms, fully or partially remove the disease's underlying cause (e.g., destroy or diminish a fungal infection), shorten a disease's duration, or do a combination of these things.

"Zwitterionic surfactant" as used herein includes a surface-active agent that comprises atoms bearing a formal charge other than zero, but in which the agent has a net charge of zero. Examples include cocoamidopropyl betaine, cocoamphoacetate (i.e., cocoamphoglycinate), cocoamidopropyl hydroxysultaine, dodecyl betaine, phospholipids (e.g., lecithin), alkyl or acyl amphopropionates or sulfobetaines (i.e., sulfonic acid analogs to carboxylic acid betaines), and the like, as well as mixtures and poly(ethylene glycol) derivatives thereof.

A "charged derivative of a zwitterionic surfactant" or "charged derivative thereof" as used herein indicates a cationic or anionic surfactant that is a salt of a zwitterionic surfactant produced by either protonation or deprotonation (e.g., by reaction of cocoamphodiacetate with sodium hydride or hydroxide to produce disodium cocoamphodiacetate). Examples include sodium cocoamphoacetate, sodium lauroamphoacetate, disodium dicocoamphodicetate, potassium cocoamphodiacetate, dipotassium cocoamphodiacetate, disodium dicocoamphodipropionate, and the like (e.g., metal salts of alkyl or acyl amphopropionates or sulfobetaines), as well as mixtures and poly(ethylene glycol) derivatives thereof.

In general, the unit prefix "u" as used herein is equivalent to "μ" or "micro." For example, "ul" is equivalent to "μl" or "microliters."

The term "w/w" or "wt/wt" means a percentage expressed in terms of the weight of the ingredient or agent over the total weight of the composition multiplied by 100.

II. Embodiments

In one embodiment, the present invention provide a topical formulation for the treatment of onychomycosis, comprising:
an antifungal agent, such as terbinafine or a salt thereof;
a zwitterionic surfactant or charged derivative thereof;
a carboxylic acid, which is selected from the group consisting of a short-chain hydroxy acid, a short-chain fatty acid, and a mixture thereof;
a lower alcohol; and
water.

In another embodiment, the present invention provide a topical formulation for the treatment of onychomycosis, comprising:
an antifungal agent, such as terbinafine or a salt thereof;
a zwitterionic surfactant or charged derivative thereof;
a carboxylic acid, which is selected from the group consisting of a short-chain hydroxy acid, a short-chain fatty acid, and a mixture thereof;
a keratolytic agent, such as urea;
a terpene, such as menthol;
panthenol;
a lower alcohol; and
water.

In another embodiment, the present invention provide a topical formulation for the treatment of onychomycosis, comprising:
an antifungal agent, such as terbinafine or a salt thereof;
a zwitterionic surfactant or charged derivative thereof;
a carboxylic acid, which is selected from the group consisting of a short-chain hydroxy acid, a short-chain fatty acid, and a mixture thereof;
a keratolytic agent, such as urea;
a triol, such as hexanetriol;
a lower alcohol; and
water.

In still another embodiment, the present invention provides a topical formulation for the treatment of onychomycosis, comprising:
an antifungal agent, such as terbinafine or a salt thereof;
a quarternary amino acid;
a keratolytic agent;
a lower alcohol; and
water.

In yet another embodiment, the present invention provide a topical formulation for the treatment of onychomycosis, comprising:
an antifungal agent, such as terbinafine or a salt thereof;
a keratolytic agent;
a short-chain detergent;
a lower alcohol; and
water.

The formulations of the present invention are especially advantageous in the amount of antifungal agent delivered to the site of fungal infection. In certain aspects, the inventive formulations are designed i) for high penetration into the skin or nail; ii) for high retention in the skin or nail; or iii) for both high penetration and high retention. The formulations are designed to balance penetration and retention, enabling an effective amount of the active ingredient to pass through the skin or nail, but also to stay in the target area for a sufficient duration to achieve its intended effect upon the fungus.

A. Anti-Fungal Agents

In certain aspects, the pharmaceutical compositions of the instant invention incorporate an anti-fungal agent. In a preferred aspect, the anti-fungal agent is a member of the classes of allylamines such as terbinafine, amorolfine, naftifine, and butenafine; azoles (including imidazoles and triazoles) such as miconazole, ketoconazole, clotrimazole, econazole, bifonazole, butoconazole, fenticonazole, isoconazole, oxiconazole, sertaconazole, sulconazole, tioconazole, itraconazole, fluconazole, voriconzole, terconazole, isavuconazole, ravuconazole, and posaconazole; polyenes such as natamycin, rimocidin, filipin, nystatin, candicidin, nystatin, candicidin, and amphoteracin B; thiazoles such as abafungin; echinocandins; thiocarbamates such as tolnaftate; phenolic compounds such as haloprogin; pyridones such as ciclopirox olamine; and miscellaneous antifungal agents such as sordarins and undecylenic acid. See Brunton, L. L. et al. *The Goodman and Gilman's Manual of Pharmocology and Therapeutics*, McGraw-Hill, New York, 2007. Various pharmaceutically acceptable salts, mixtures, and combinations of anti-fungal are also contemplated in this invention.

In a more preferred aspect, the antifungal agent is an allylamine anti-fungal agent. In a more preferred embodiment, the allylamine anti-fungal agent is selected from the group of amorolfine, butenafine, naftifine, terbinafine, and a pharmaceutically acceptable salt thereof. In an even more preferred embodiment, the allylamine anti-fungal agent is terbinafine or a pharmaceutically acceptable salt thereof (e.g., terbinafine hydrochloride).

In an alternative preferred aspect of the invention, the anti-fungal agent's mechanism of action is inhibition of the ergosterol synthesis pathway in a fungus. In a more preferred aspect, the anti-fungal agent's mechanism of action is inhibition of the enzyme squalene epoxidase.

In still another preferred aspect, the anti-fungal agent is useful in the treatment of a mammal, including a human or a domestic or farm animal, such as a dog, horse, cat, sheep, pig, or cow. A more preferred, but non-limiting, mammal is a human.

In still yet another preferred aspect, the formulation comprises at least about 1% to 15% or to 20% (w/w) of terbinafine or a pharmaceutically acceptable salt thereof (e.g., hydrochloride). For example, the anti-fungal agent is present at about 1, 2, 3, 4, 5, 6, 7, 8, 9, 10, 11, 12, 13, 14, 15, 16, 17, 18, 19, or 20% by weight, such as about 10% or 17% (w/w). Alternatively, the formulation comprises at most about 1, 2, 3, 4, 5, 6, 7, 8, 9, 10, 11, 12, 13, 14, 15, 16, 17, 18, 19, or 20% (w/w) of the anti-fungal agent.

More preferably, the formulation can comprise about 5% to 25% of the anti-fungal agent, and preferably, about 10% to 17% (w/w). For example, the anti-fungal agent is present at about 10, 11, 12, 13, 14, 15, 16, or 17% by weight such as about 10% or 17% (w/w). Alternatively, the formulation comprises at most about 7, 8, 9, 10, 11, 12, 13, 14, 15, 16, or 17% (w/w) of the anti-fungal agent.

In certain alternative embodiments, the anti-fungal agent by weight can be about 10%, 15%, 20%, 25%, or even 30% (w/w).

In certain preferred aspects, the formulations of the current invention have the advantage of containing high concentrations of low-solubility or hard-to-formulate drugs such as terbinafine or butenafine. Such concentrated formulations may be of particular benefit in treatment of chronic diseases of the nail or other difficult-to-treat areas of the body (e.g., onychomycosis) because the high concentrations can 1) increase the effective concentration of drug in the affected area or 2) improve retention of the drug at or near the affected area.

B. Zwitterionic Surfactants

In one aspect, the composition comprises a zwitterionic surfactant or a charged derivative thereof. In one aspect, the zwitterionic surfactant is selected from the group of disodium cocoamphodiacetate, sodium cocoamphodiacetate, cocoamidopropyl betaine, and a mixture thereof.

Other zwitterionic surfactants or charged derivatives thereof include, but are not limited to, amino acids such as β-N-alkylaminopropionic acids, aminopropyl alkylglutamide, alkylaminopropionic acid, sodium alkylimidodipropionate, dihydroxyethyl alkyl glycinate, and lauroamphocarboxyglycinate; imino acids such as N-alkyl-β-iminodipropionic acids; imidazoline derivatives that are not N,N'-dialkylated; quaternary ammonium amino acid sulfobetaines such as alkyl amidopropyl hydroxysultaines, cocoamidopropyl hydroxysultaine, sodium cocoamphohydroxypropyl sulfonate, or sodium capryloamphohydroxypropyl sulfonate; quaternary ammonium amino acid betaines, e.g., dodecyl betaine; alkyl amidopropyl betaines such as cocoamidopropyl betaine; alkyl dimethyl betaines; phospholipids such as lecithin; acyl dialkyl ethylenediamines, e.g., sodium acyl amphoacetate, disodium acyl amphodipropionate, disodium alkyl amphodiacetate, sodium acyl amphohydroxypropyl sulfonate, disodium acyl amphodiacetate, and sodium acyl amphopropionate; and the like.

In a preferred aspect, the zwitterionic surfactant or charged derivative thereof is a salt of cocamphodiacetate. More preferably, the salt of cocamphodiacetate is disodium cocamphodiacetate.

Advantageous zwitterionic surfactants with quaternary nitrogens include alkylbetaines, alkylamidopropylbetaines, and alkylamidopropyl-hydroxysulfaines.

In preferred aspects, the composition comprises about 5% to 25% (w/w) of the zwitterionic surfactant or charged derivative thereof (e.g., about 5, 6, 7, 8, 9, 10, 11, 12, 13, 14, 15, 16, 17, 18, 19, 20, 21, 22, 23, 24, or 25% by weight). In more preferred aspects, the compositions include about 10% to 20% (w/w) of the zwitterionic surfactant or charged derivative thereof (e.g., about 10, 11, 12, 13, 14, 15, 16, 17, 18, 19, or 20% by weight). Still more preferably, the composition comprises about 10% (w/w) of the zwitterionic surfactant or charged derivative thereof. Alternatively, the composition comprises about 15%, 17%, or 20% (w/w) of the zwitterionic surfactant or charged derivative thereof.

In certain alternative preferred aspects, the composition comprises about 10% to 20% (w/w) of the zwitterionic surfactant, such as about 10, 11, 12, 13, 14, 15, 16, 17, 18, 19, or 20% (w/w). In other aspects, the compositions include about 0.5% to 20% (w/w) of the zwitterionic surfactant. More preferably, the composition comprises 5% (w/w) of the zwitterionic surfactant.

C. Short-Chain Carboxylic Acids

In certain aspects, the topical formulation further comprises a carboxylic acid; preferably, a short-chain carboxylic acid such as acetic acid, lactic acid, tartaric acid, malic acid, succinic acid, glycolic acid, citric acid, caprylic acid, caproic acid, and the like, as well as a mixture thereof. More preferably, the carboxylic acid is a short-chain hydroxy acid such as lactic acid. Alternatively, the carboxylic acid is a short-chain fatty acid such as caprylic acid.

In still other aspects, the composition comprises a carboxylic acid in about 3% to 10% by weight such as about 3, 4, 5, 6, 7, 8, 9, or 10% (w/w). Alternatively, the composition comprises about 5%, 7.5%, or 8.3% (w/w).

In certain alternative aspects, the topical formulation further comprises a short-chain carboxylic acid, such as acetic, lactic, tartaric, malic, succinic, or a mixture thereof. Typically, the short-chain carboxylic acid is present at about 3% to 7% (w/w), such as 3, 4, 5, 6 or 7% (w/w). Alternatively, the composition comprises about 0.5% to 12% (w/w) of the short-chain carboxylic acid, and more preferably, about 5% (w/w). Alternatively, the composition comprises 0.5% to 10% (w/w) and still more preferably, about 4, 5 or 6% (w/w).

In still other alternative aspects, the composition comprises a short-chain carboxylic acid in about 5% to 15% (w/w), such as about 5, 6, 7, 8, 9, 10, 11, 12, 13, 14 or 15% (e.g. about 10% (w/w)).

D. Lower Alcohols

In one preferred aspect, the compositions and formulations include a lower alcohol. More preferably, the lower alcohol is a monohydric lower alcohol, and still more preferably, the lower alcohol is selected from a $C_1$ to $C_6$ alkanol, such as methanol, ethanol, propanol, isopropanol, butanol, isobutanol, sec-butanol, pentanol, and the like, as well as a mixture thereof. Ethanol is especially preferred.

In certain aspects the composition includes about 10% to 60% (w/w) of the lower alcohol (e.g., ethanol). In other aspects, the formulations include about 10, 15, 20, 22, 23, 25, 30, 32, 33, 35, 36, 40, 41, 42, 45, 50, 55, or 60% (w/w) of a lower alcohol. More preferably, the composition comprises from about 20% to 50% (w/w) of a lower alcohol, such as about 20, 22, 23, 25, 30, 32, 33, 35, 36, 39, 40, 41, 42, 45, or 50%. Still more preferably, the composition comprises from about 20 to 25%, about 22.5 to 30%, about 20 to 36%, about 30 to 45%, about 30 to 40%, about 32.5 to 39.5%, about 35 to 50%, about 39 to 50%, about 39 to 45%, or about 41.7 to 50% (w/w) of a lower alcohol. Yet still more preferably, the composition comprises about 22, 22.5, 23, 25, 30, 32, 32.5, 33, 35, 35.5, 36, 39, 39.5, 40, 41, 41.7, 42, or 50% (w/w) of a lower alcohol.

In certain alternative aspects, the composition includes about 35% to 65% (w/w) of the lower alcohol (e.g., ethanol). In other aspects, the formulations include at least about 3, 5, 7, 9.5, 10, 10.5, 11, 11.5, 12, 14, 15, 20, 25, 30, 31, 31.5, 32, 32.5, 33, 35, 36, 37, 38, 39, 40, 41, 42, 43, 44, 44.5, 45, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 58, 59, 60, 61, 62, 63, 64, 65, 66, 67, 68, 69, 70, 71, 72, 73, 74, or 75% (w/w) of a lower alcohol. More preferably, the composition comprises at least about 35, 36, 37, 38, 39, 40, 41, 42, 43, 44, 44.5, 45, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 58, 59, 60, 61, 62, 63, 64, 65, 66, 67, 68, 69, 70, 71, 72, 73, 74, or 75% (w/w) of a lower alcohol. Still more preferably, the composition comprises at least about 38, 39, 40, 41, 42, 43, 44, 44.5, 45, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 58, 59, 60, 61, 62, 63, 64, 65, 66, 67, 68, 69, 70, 71, 72, 73, 74, or 75% (w/w) of a lower alcohol.

In another aspect, the lower alcohol is a diol or triol. In an alternative, preferred aspect, the formulations can alternatively or additionally include a diol or triol. Suitable diols and triols include, but are not limited to, propylene glycol, butanediol, butynediol, pentanediol, hexanediol, octanediol, neopentyl glycol, 2-methyl-1,3-propanediol, diethylene glycol, triethylene glycol, tetraethylene glycol, dipropylene glycol, dibutylene glycol, propylene glycol, butanetriol, pentanetiol, hexanetriol, glycerol, and the like, as well as a mixture thereof. In one aspect, the formulation comprises about 0% to 15% (w/w) of propylene glycol, and preferably about 0 to 5%. In certain preferred aspects, the diol is a glycol, such as ethylene glycol, propylene glycol, and a mixture thereof. In other preferred aspects, the triol is hexanetriol. In one aspect, the formulation comprises about 1% to 15% (w/w) of the triol (preferably, hexanetriol), and preferably, about 1 to 5%, or about 3% (w/w).

E. Water

In certain aspects, the compositions include water. Preferably, water is present from about 5% to 25% (w/w) such as about 5, 6, 7, 8, 9, 10, 11, 12, 12.5, 13, 14, 15, 16, 16.6, 17, 17.5, 18, 19, 20, 21, 22, 23, 24 or 25% by weight. More preferably, the composition includes from about 5 to 10%, about 10 to 20%, about 10 to 15%, or about 15 to 20% (w/w) water. Alternatively, the mixture includes about 8, 10, 12, 12.5, 13, 16, 16.6, or 17% (w/w) water.

In certain alternative aspects, water is present from about 2% (w/w) to 35% (w/w). Preferably, water is present at about 5% to 25% (w/w), such as about 5, 6, 7, 8, 9, 10, 11, 12, 13, 14, 15, 16, 17, 18, 19, 20, 21, 22, 23, 24, 25, 26, 27, 28, 29 or 30% (w/w) (e.g., about 10%, 20%, 25% or 30% (w/w)).

F. Keratolytic Agents

In certain aspects, the present formulations include a keratolytic agent. Suitable keratolytic agents include, but are not limited to, urea, ammonium thioglycolate, calcium thioglycolate, potassium thioglycolate, and the like, as well as a mixture thereof. In one preferred embodiment, the keratolytic agent is urea. In another preferred embodiment, the keratolytic agent is ammonium thioglycolate.

In one aspect, the keratolytic agent is present at about 5% to 20% (w/w), such as about 5, 6, 7, 8, 9, 10, 11, 12, 13, 14, 15, 16, 17, 18, 19, or 20% by weight. More preferably, the composition contains from about 10 to 15% (w/w) keratolytic agent. In a still more preferred aspect, the composition includes 10% or 15% (w/w) of the keratolytic agent.

In an alternative aspect, the keratolytic agent is present at about 1% to 25%, about 3% to 18% (w/w), or about 6% to 30% (w/w). For example, the keratolytic agent is present at about 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30% (w/w). In one preferred aspect, the keratolytic agent is present at about 6% (w/w) (e.g., 10% of a 60% aqueous solution of ammonium thioglycolate).

Typically, a keratolytic agent, i.e., a desquamating agent, helps loosen keratin in the nail, thus i) increasing the nail's permeability; ii) aiding in the process of desquamation or the removal of the upper layers of the damaged or diseased nail; or iii) both increasing permeability and aiding removal. Examples of keratolytic agents include, but are not limited to, urea, benzoylperoxide, salicylic acid, resorcinol, and tretinoin. Others can be found in "Remington: *The Science and Practice of Pharmacy*, Nineteenth Edition, pp. 878-879." The preferred keratolytic agents are those known in the art for use with onychomycosis medications. For example, these include ammonium thioglycolate, urea, sodium sulfide and ammonium thioglycolate.

In another aspect, the keratolytic agent will be present in an amount from about 0.01% to 25% (w/w); preferably, from about 0.5% to 20%; and more preferably, from about 1% to 20%.

In certain aspects, the keratolytic agent is a mixture of urea and ammonium thioglycolate. For example, the urea is present at about 10% to 20% (w/w) in the total amount of the mixture of keratolytic agents. That is, even though the amount of keratolytic agent in the composition is even higher (i.e., about 25%, 30% or 35% (w/w)), urea is present from about 10% to about 20% (w/w) of the composition. Alternatively, urea is present at about 15% (w/w) in the mixture of keratolytic agents.

In certain aspects, ammonium thioglycolate is present from about 5% to 15% (w/w) in the mixture of keratolytic agents, or from about 5% to 11% (w/w).

In certain alternative aspects, ammonium thioglycolate is present at about 3% to 9% (w/w) in the mixture, or about 3% to 7% (w/w) in the mixture of keratolytic agents. In one aspect, the keratolytic agent is a mixture of about 10% (w/w) urea and about 6% (w/w) ammonium thioglycolate. In another aspect, the keratolytic agent will be present in an amount of about 0.01% to 25% (w/w) of the composition; preferably, about 0.5% to 20%; and more preferably, about 1% to 20%.

G. Terpenes

In still other aspects, the composition includes a terpene. Examples include, but are not limited to, menthol, d-limonene, limonene oxide, geraniol, α-pinene, α-pinene oxide, thymol, menthone, neomenthol, 3-carene, l-carvol, carvone, carveol, 1,8-cineole (eucalyptol), citral, dihydrocarveol, dihydrocarvone, 4-terpinenol, fenthone, pulegone, pulegol, isopulegol, piperitone, camphor, a-terpineol, terpinen-4-ol, linalool, carvacrol, trans-anethole, ascaridole, safrole, racemic mixtures thereof, pharmaceutically acceptable isomers thereof, and mixtures thereof.

In a preferred embodiment, the composition of the present invention comprises menthol. In certain preferred aspects, a second penetration enhancer can be present (e.g., a keratolytic agent and a terpene).

In one aspect, the composition comprises from about 2% to 10% (w/w) of the terpene, such as about 2, 3, 4, 5, 6, 7, 8, 9, or 10% of the terpene. Preferably, the composition comprises from about 2% to 5% (w/w) of the terpene, such as about 2, 3, 4, or 5% of the terpene. More preferably, the composition comprises about 3% terpene; alternatively, the composition comprises about 5% terpene. Still more preferably, the terpene is menthol.

In certain aspects, the terpene penetration enhancer can be included within an essential oil. Essential oils that include a substantial proportion of at least one terpene penetration enhancer include oils of peppermint, eucalyptus, chenopodium, anise, and yling-yling.

In still other alternative aspects, the compositions include a terpene, such as menthol. The formulation typically has about 3% to 7% (w/w), such as about 3, 4, 5, 6, or 7% of such a terpene present. In other aspects, the terpene is present from about 1% to about 10% (w/w), such as about 1, 2, 3, 4, 5, 6, 7, 8, 9 or 10% (e.g., 5% (w/w)).

In an alternative specific embodiment, the composition of the present invention comprises limonene or geraniol. In one aspect, the composition comprises about 0.1% to 5% (w/w) of limonene or geraniol.

H. Panthenol

In yet another aspect, the composition further comprises panthenol. In one aspect, the panthenol is present from about 5% to 15% (w/w) such as about 5, 6, 7, 7.5, 8, 9, 10, 11, 12, 13, 14, or 15%. Preferably, the composition includes about 7.5% (w/w) panthenol.

In another aspect, the panthenol may be racemic, enantiomerically enriched L- or D-panthenol, or substantially pure L- or D-panthenol. Preferably, the panthenol is substantially pure D-panthenol.

I. Thickeners

In still yet another aspect, the compositions and formulations herein comprise at least one thickening agent, such as a cellulose polymer, a carbomer, a polyvinyl pyrrolidone, a polyvinyl alcohol, a poloxamer, a xanthan gum, a locus bean gum, a guar gum and mixtures thereof. Preferably, the formulation includes a cellulosic thickening agent. Suitable cellulosic thickening agents include, but are not limited to, hydroxypropyl cellulose (HPC) of various grades, hydroxypropyl methyl cellulose, hydroxyethyl cellulose, hydroxyethyl methyl cellulose, ethyl cellulose, methyl cellulose, carboxymethyl cellulose, dextran, guar gum, pectin, starch, cellulose, and the like. More preferably, the cellulosic thickening agent is HPC.

In a preferred aspect, the composition comprises about 0.5% to 5% (w/w) of the thickening agent, such as about 0.5, 0.6, 0.7, 0.8, 0.9, 1, 2, 3, 4, or 5%. More preferably, the composition comprises from about 0.5% to 1% of a thickening agent or about 0.5 to 2% of a thickening agent. Still more preferably, the composition comprises about 2% of a thickening agent. Alternatively, the composition comprises about 1% of a thickening agent.

In an alternative aspect, the compositions and formulations herein comprise at least one thickening agent, such as a polyacrylate, a salt or ester thereof, or a mixture of such polymers. Preferably, the polyacrylate is a Eudragit® polymer such as Eudragit® L-100 (a copolymer comprising polymethacrylate or a salt thereof). Other Eudragit® polymers include a trimethylammonioethyl or dimethylaminoethyl ester of polymethacrylate and a copolymer comprising polyacrylates, preferably a copolymer including polymethacrylate.

In an alternative, preferred aspect, the composition comprises about 0.5% to about 7% (w/w), such as about 0.5, 0.6, 0.7, 0.8, 0.9, 1, 2, 3, 4, 5, 6, or 7% (e.g., 1% to 5% (w/w)) of a thickening agent. More preferably, the composition comprises from about 1% to 2% of a thickening agent. Still more preferably, the composition comprises about 1% of a thickening agent. Alternatively, the composition comprises about 2% of a thickening agent.

J. Film-Forming Agents

In another aspect, the compositions and formulations herein comprise at least one thickening agent, such as a a polyacrylate, a salt or ester thereof, or a mixture of such polymers. Preferably, the polyacrylate is a Eudragit® polymer such as Eudragit® L-100 (a copolymer comprising polymethacrylate or a salt thereof). Other Eudragit® polymers include a trimethylammonioethyl or dimethylaminoethyl ester of polymethacrylate or a copolymer comprising polyacrylates, preferably including polymethacrylate.

In a preferred aspect, the composition comprises about 0.5% to 5% (w/w) of the film-forming agent, such as about 0.5, 0.6, 0.7, 0.8, 0.9, 1, 2, 3, 4, or 5%. More preferably, the composition comprises from about 0.5% to 1% of a film-forming agent or about 0.5 to 2% of a film-forming agent. Still more preferably, the composition comprises about 2% of a film-forming agent. Alternatively, the composition comprises about 1% of a film-forming agent.

In an alternative, preferred aspect, the composition comprises about 0.1% to 5% (w/w) of the film-forming agent, such as about 0.1, 0.2, 0.3, 0.4, 0.5, 0.6, 0.7, 0.8, 0.9, 1, 2, 3, 4, or 5% (w/w). More preferably, the composition comprises from about 0.5% to 1% of a film-forming agent or about 0.5 to 2% of a film-forming agent. Still more preferably, the composition comprises about 2% of a film-forming agent. Alternatively, the composition comprises about 1% of a film-forming agent.

K. Ester Solvents

In another aspect, the formulations optionally contain a solvent that is an ester of a lower alcohol and a short-chain carboxylic acid. Examples include butyl acetate, ethyl acetate, isopropyl acetate, ethyl propanoate, and the like. Preferably, the formulation contains ethyl acetate.

In still another aspect, the formulation comprises from about 5% to 20% (w/w) of the ester. More preferably, the formulation comprises from about 5% to 10%, about 7.5% to 15%, about 10% to 20%, or about 15% to 20% of the ester. Still more preferably, the ester comprises about 15% or 20% of the ester. Yet still more preferably, the ester is ethyl acetate.

L. Other Surfactants

1. Nonionic Surfactants

In yet another aspect, the composition comprises at least one pharmaceutically acceptable surfactant. Preferably, the surfactant is a nonionic surfactant. More preferably, the surfactant is a polysorbate surfactant. Still more preferably, the surfactant is polysorbate 20. Other surfactants include, but are not limited to, Tween® 20, POE (20) sorbitan monooleate, Tween® 40, POE (40) sorbitan monooleate, Tween® 60, POE (60) sorbitan monooleate, Tween® 80, POE (80) sorbitan monooleate, glycerine monolaurate, and a mixture thereof.

Other nonionic surfactants include, but are not limited to, cetomacrogol 1000, cetostearyl alcohol, cetyl alcohol, cocoamide diethanolamine, cocoamide monoethanolamine, decyl glucoside, glyceryl laurate, lauryl glucoside, polyoxyethylene ethers of fatty acids such as cetyl alcohol or stearyl alcohol, narrow-range ethoxylates, octyl glucoside, oleyl alcohol, poloxamers, polyethylene glycol, sorbitan monolaurate, polyoxyethylene sorbitan monolaurate, sorbitan dioleate, sorbitan trilaurate, sorbitan monopalmitate, polyoxyethylene (20) sorbitan monopalmitate, sorbitan monostearate, sorbitan tristearate, polyoxyethylene (20) sorbitan monostearate, sorbitan monooleate, sorbitan trioleate, polyoxyethylene sorbitan monooleate, stearyl alcohol, sucrose coconut fatty ester mixtures, and sucrose monolaurate.

Non-limiting examples of non-ionic surfactants include polysorbates; poly(oxyethylene) (POE) fatty acid esters, such as Myrj 45, Myrj 49, Myrj 52 and Myrj 59; poly(oxyethylene) alkylyl ethers, such as poly(oxyethylene)cetyl ether, poly (oxyethylene)palmityl ether, polyethylene oxide hexadecyl ether, polyethylene glycol cetyl ether, Brij 38, Brij 52, Brij 56 and Brij W1; sucrose esters, partial esters of sorbitol and its anhydrides, such as sorbitan monolaurate; mono or diglycerides and isoceteth-20.

Other non-ionic surfactants include, but are not limited to, fatty acid diesters, polyethylene glycol glycerol fatty acid esters, alcohol-oil transesterification products, polyglycerized fatty acids, sterol and sterol derivatives, polyethylene glycol alkyl ethers, sugar esters, polyethylene glycol alkyl phenols, polyoxyethylene-polyoxypropylene block copolymers, sorbitan fatty acid esters and lower alcohol fatty acid esters.

2. Cationic Surfactants

In yet another aspect, the composition comprises a cationic detergent or surfactant. Suitable surfactants include an octyl trimethylammonium salt, a cetyl trimethyl ammonium salt, and a mixture thereof. The cationic detergent may be present at about 1% to 10% w/w, such as about 1, 2, 3, 4, 5, 6, 7, 8, 9 or 10% w/w. Preferably, the cationic detergent is present at about 5% w/w. Cationic surfactants further include, e.g., stearyl trimethyl ammonium chloride and benzyl trimethyl ammonium chloride.

Other cationic surfactants include, e.g., alkylamines, alkylimidazoles, ethoxylated amines, quaternary surfactants (e.g., non-amphoteric quaternary surfactants), and esterquats. Quaternary surfactants contain at least one nitrogen atom, which is covalently bonded to four alkyl or aryl groups. The cationic surfactants that may be used in accordance with the invention can also be selected from non-amphoteric quaternary ammonium compounds, in particular benzyltrialkyl ammonium chlorides or bromides (e.g., benzyl dimethylstearyl ammonium chloride); alkyl trialkyl ammonium salts (e.g., cetyl trimethyl ammonium chloride or bromide, alkyl dimethylhydroxyethyl ammonium chloride or bromide, dialkyl dimethyl ammonium chloride or bromide, and alkylamide ethyltrimethyl ammonium ether sulfates); alkylpyridinium salts (e.g., lauryl or cetyl pyrimidinium chloride); imidazoline derivatives (e.g., N,N'-dialkylimidazoline derivatives); compounds having cationic character, such as amine oxides (e.g., alkyl dimethylamine oxides or alkylaminoethyl dimethylamine oxides); and the like. The use of cetyl trimethyl ammonium salts is preferred.

3. Anionic Surfactants

In yet another aspect, the compositions contain an anionic surfactant such as an alkyl sulfate, e.g., sodium, ammonium or triethylammonium (TEA) lauryl sulfate. In a preferred embodiment, the anionic surfactant is sodium lauryl sulfate. Other anionic surfactants include acylamino acids (and their salts), such as acyl glutamates (e.g., sodium acyl glutamate, di-TEA palmitoyl aspartate, and sodium caprylic/capric glutamate); acyl peptides (e.g., palmitoyl-hydrolyzed milk protein, sodium cocoyl-hydrolyzed soya protein and sodium/potassium cocoyl-hydrolyzed collagen); sarcosinates (e.g., myristoyl sarcosin, TEA lauroyl sarcosinate, sodium lauroyl sarcosinate and sodium cocoyl sarcosinate); taurates (e.g., sodium lauroyl taurate and sodium methylcocoyl taurate); acyl lactylates (e.g., lauroyl lactylate or caproyl lactylate); alaninates; and the like.

Other anionic surfactants include carboxylic acids and derivatives, such as carboxylic acids, e.g., lauric acid, aluminum stearate, magnesium alkanolate, and zinc undecylenate; ester carboxylic acids, e.g., calcium and sodium stearoyl lactylates, laureth-6 citrate, and sodium PEG-4 lauramide carboxylate; ether carboxylic acids, e.g., sodium laureth-13 carboxylate, and sodium PEG-6 cocoamide carboxylate; and the like.

Other anionic surfactants include esters of phosphoric acid and salts, e.g., dilaureth-4 phosphate.

Other anionic surfactants include sulfonic acids and salts, such as acyl isethionate, e.g., sodium-ammoniumcocoyl isethionate, alkylaryl sulfonates; alkyl sulfonates, e.g., sodium coco monoglyceride sulfate, sodium $C_{12-14}$ olefinsulfonate, sodium lauryl sulfoacetate and magnesium PEG-3 cocamide sulfate; sulfosuccinates, e.g., dioctyl sodium sulfosuccinate, disodium laureth sulfosuccinate, disodium lauryl sulfosuccinate, disodium undecylenamido-MEA-sulfosuccinate, and PEG-5 lauryl citrate sulfosuccinate; esters of sulfuric acid, such as alkyl ether sulfate, e.g., sodium, ammonium, magnesium, MIPA, TIPA, laureth sulfate, sodium myreth sulfate and sodium $C_{12-13}$ pareth sulfate; and the like.

In yet another alternative aspect, the composition comprises an anionic surfactant such as an alkyl sulfate (e.g., sodium, ammonium or TEA lauryl sulfate). In a preferred embodiment, the anionic surfactant is sodium lauryl sulfate. Other anionic surfactants include acylamino acids (and their salts), such as acyl glutamates (e.g., sodium acyl glutamate, di-TEA-palmitoyl aspartate, and sodium caprylic or capric glutamate); acyl peptides (e.g., palmitoyl-hydrolyzed milk protein, sodium cocoyl-hydrolyzed soya protein, and sodium/potassium cocoyl-hydrolyzed collagen); sarcosinates (e.g., myristoyl sarcosin, TEA-lauroyl sarcosinate, sodium lauroyl sarcosinate and sodium cocoyl sarcosinate); taurates (e.g., sodium lauroyl taurate and sodium methylcocoyl taurate); acyl lactylates (e.g., lauroyl lactylate and caproyl lactylate); and alaninates;

Other anionic surfactants include carboxylic acids and derivatives, such as carboxylic acids (e.g., lauric acid, aluminum stearate, magnesium alkanolate, and zinc undecylenate); ester carboxylic acids (e.g., calcium stearoyl lactylate, laureth-6 citrate, and sodium PEG-4 lauramide carboxylate); and ether carboxylic acids (e.g., sodium laureth-13 carboxylate and sodium PEG-6 cocoamide carboxylate).

Other anionic surfactants include esters of phosphoric acid and salts, such as dilaureth-4 phosphate.

Other anionic surfactants include sulfonic acids and salts, such as acyl isethionate, (e.g., sodium-ammoniumcocoyl isethionate); alkylaryl sulfonates; alkyl sulfonates (e.g., sodium coco monoglyceride sulfate, sodium $C_{12-14}$ olefinsulfonate, sodium lauryl sulfoacetate and magnesium PEG-3 cocamide sulfate); sulfosuccinates (e.g., dioctyl sodium sulfosuccinate, disodium laureth sulfosuccinate, disodium lauryl sulfosuccinate, disodium undecylenamido-MEA-sulfosuccinate, and PEG-5 lauryl citrate sulfosuccinate); and esters of sulfuric acid, such as alkyl ether sulfate (e.g., sodium, ammonium, magnesium, MIPA, TIPA, laureth sulfate, sodium myreth sulfate, and sodium $C_{12-13}$ pareth sulfate).

M. Zwitterionic Acids

In certain aspects, the present formulations include zwitterionic acids; more preferably, the zwitterionic acid is a quaternary amino acid. Suitable quaternary amino acids include, but are not limited to, carnitine, acetyl carnitine, quaternary amino betaines (e.g., quaternary amino carboxybetaines or sulfobetaines), and a mixture thereof. In certain preferred aspects, the quaternary amino acid is a mixture of carnitine and acetyl carnitine. In a preferred aspect, a specific betaine useful in the present invention is glycine betaine (i.e., N,N,N-trimethylglycine).

Typically, the zwitterionic acid or quaternary amino acid is present at about 5% to 20% (w/w). For example, the quaternary amino acid is present at about 5, 6, 7, 8, 9, 10, 11, 12, 13, 14, 15, 16, 17, 18, 19 or 20% by weight. In other instances, the quaternary amino acid is present at about 12% to 17% (w/w).

The term "sulfobetaine" includes zwitterionic acid molecules having a charge on the sulfur atom (e.g., S,S-dimethylsulfonioacetate), as well as a charge on the nitrogen atom (e.g., 3-(N,N-dimethyloctylammonio)propanesulfonate inner salt or octyl sulfobetaine). However, in a preferred aspect, the formulations of the present invention uses molecules wherein the nitrogen is charged.

In certain alternative aspects, the present formulations include a quaternary amino acid. Suitable quaternary amino acids include, but are not limited to, carnitine, acetyl carnitine, betaine, sulfobetaine and a mixture thereof. In certain preferred instances, the quaternary amino acid is a mixture of carnitine and acetyl carnitine. Typically, the quaternary amino acid is present at 5% to about 20% (w/w). For example, the quaternary amino acid is present at about 5, 6, 7, 8, 9, 10, 11, 12, 13, 14, 15, 16, 17, 18, 19 or 20% (w/w). In other instances, the quaternary amino acid is present at about 12% to about 17% (w/w).

N. Other Components

In certain other aspects, the topical formulation further comprises a short-chain detergent (i.e., surfactant). In a preferred embodiment, the short-chain detergent is sodium isethionate. The short-chain detergent is present at about 10% to about 20% w/w, such as about 10, 11, 12, 13, 14, 15, 16, 17, 18, 19 or 20% w/w.

In still other aspects, the topical formulation further comprises phenol or a related aryl alcohol.

In one aspect, the composition additionally comprises an anti-oxidant. Preferred anti-oxidants for use in the present invention include butylated hydroxytoluene, butylated hydroxyanisole, ascorbyl linoleate, ascorbyl dipalmitate, ascorbyl tocopherol maleate, calcium ascorbate, carotenoids, kojic acid and its pharmaceutically acceptable salts, thioglycolic acid and its pharmaceutically acceptable salts (e.g., ammonium), tocopherol, tocopherol acetate, tocophereth-5, tocophereth-12, tocophereth-18, or tocophereth-80. In certain aspects, the anti-oxidant may also be a eutectic agent.

In still other aspects, the composition additionally comprises at least one pharmaceutically acceptable surfactant, emulsifier, thickener, or lacquer-forming agent. In a preferred aspect, the composition additionally comprises at least one surfactant, emulsifier, thickener, or lacquer-forming agent.

In an alternative preferred aspect, the formulation includes a penetration enhancer. In certain aspects, the penetration enhancer is selected from terpenes, fatty acid esters, and fatty acid alcohols. More preferably, the penetration enhancer is a terpene, and preferably, a terpene as previously described.

In another alternative, preferred aspect, a fatty acid ester is used in the composition. An example of a preferred penetration enhancer is glyceryl monoesters. More preferably, the penetration enhancer is glyceryl monolaurate.

In still yet another aspect, the formulation is a composition selected from the group consisting of a cream, an emulsion, a microemulsion, a gel (e.g., a hydrogel, an organogel, or an inorganic or silica gel), a lacquer, a lotion, an ointment, a solution (e.g., a moderately to highly viscous solution) and a transdermal patch.

In another aspect, the formulation is acidic. In certain aspects, the formulation has a pH of below about 7.5, of below about 6.5, of below about 5.5, of below about 4.5, of below about 3.5, or of below about 2.5. In certain other aspects, the pH of the formulation may range from about 1.5 to about 7, about 2 to about 7, about 3 to about 7, about 4 to about 7, or about 5 to about 7. In still other aspects, the pH of the formulation may range from about 1.5 to about 5.5, about 2.5 to about 5.5, about 3.5 to about 5.5, or about 4.5 to about 5.5. The formulation may include a buffering agent to maintain its acidic pH. Preferably, the formulation has a pH value between about 4 and about 7.

In yet another aspect, the formulation is basic. In certain aspects, the formulation has a pH of above about 7, of above about 8, of above about 9, of above about 10, of above about 11, or of above about 12. In certain other aspects, the pH of the formulation may range from about 7 to about 12.5, about 7 to about 11.5, about 7 to about 10.5, about 7 to about 9.5, or about 7 to about 8.5. In still other aspects, the pH of the formulation may range from about 9 to about 12.5, about 9 to about 11.5, about 9 to about 10.5, or about 8.5 to about 10. The formulation may include a buffering agent to maintain its basic pH. Preferably, the formulation has a pH value between about 7 and about 10.

In still yet another aspect, the formulation is neutral. In certain aspects, the formulation has a pH of about 7. In certain other aspects, the formulation has a pH from about 6 to about 8.5, from about 5.5 to 8, about 6 to about 8, about 6.5 to about 8.5, or from about 6.5 to about 7.5. The formulation may include a buffering agent to maintain its neutral pH. Preferably, the formulation has a pH value between about 6 and about 8.5.

In one embodiment, the compositions of the present application include a pH adjusting agent. In a preferred embodiment, the pH adjusting agent is present in an effective amount.

In one embodiment, the pH-adjusting agent is a base. Suitable pH-adjusting bases include bicarbonates, carbonates, hydroxides (such as alkali or alkaline earth metal hydroxides as well as transition metal hydroxides), and the like. In an alternative aspect, suitable pH-adjusting bases include amines, such as diethanolamine, triethanolamine, and aminopropanol; bicarbonates; carbonates; and hydroxides, such as ammonium hydroxide, alkali or alkaline earth metal hydroxides, and transition metal hydroxides. Additionally or alternatively, the pH-adjusting agent can be an acid, an acid salt, or mixtures thereof. More particularly, the pH-adjusting agent comprises two agents (e.g., sodium hydroxide and hydrochloric acid) that are included as needed to adjust the final pH of the composition to a desired pH.

Other pH adjusting agents can also be used, including other acid, acid salts, or mixtures thereof. Further, the pH adjusting agent can additionally or alternately be a buffer. Suitable buffers include citrate/citric acid buffers, acetate/acetic acid buffers, phosphate/phosphoric acid buffers, formate/formic acid buffers, propionate/propionic acid buffers, lactate/lactic acid buffers, carbonate/carbonic acid buffers, ammonium/ammonia buffers, and the like.

In a particular embodiment, the inventive formulation includes a buffer, and a second pH-adjusting agent (e.g., sodium hydroxide or hydrochloric acid) to adjust the pH of the composition to a desired pH. More preferably, the second pH-adjusting agent comprises two agents (e.g., sodium hydroxide and hydrochloric acid) that are included as needed to adjust the pH of the hydroalcoholic chassis and/or final composition to a desired pH.

In a preferred aspect, the topical formulations of the present invention comprise a pH-adjusting agent. In one embodiment, the pH-adjusting agent is a base. Suitable pH-adjusting bases include amines (e.g., diethanolamine or triethanolamine), bicarbonates, carbonates, and hydroxides (e.g., alkali or alkaline earth metal hydroxides as well as transition metal hydroxides). The pH-adjusting agent is preferably sodium hydroxide and is present in an amount sufficient to adjust the pH of the composition to between about pH 4.0 to about 8.5; more preferably, to between about pH 5.5 to about 7.0 (e.g., pH 6.0 or 6.5). Alternatively, the pH-adjusting agent can also be an acid, an acid salt, or mixtures thereof. In a preferred embodiment, the pH-adjusting agent is an acid.

III. Characteristics of Topical Formulations

Solubility

In certain preferred aspects, the formulation embodiments of the current invention have the advantage of containing high concentrations of low-solubility or hard-to-formulate drugs such as terbinafine or butenafine. Such concentrated formulations may be of particular benefit in treatment of chronic diseases of the nail or other difficult-to-treat areas of the body (e.g., onychomycosis) because the high concentrations can (1) increase the effective concentration of drug in the affected area; (2) improve retention of the drug at or near the affected area; or both.

The solubility of terbinafine in various aqueous and organic solvents was investigated (Example 17). The findings indicated that terbinafine shows high solubility in organic solvents, lower solubility in non-polar solvents, and moderate solubility in aqueous solvents with a pH of 4 and 6.

Despite difficulties in solubilizing terbinafine, the inventors have surprisingly been able to prepare topical formulations with high concentrations of active. As shown in Table 17, for example, the solubility of terbinafine in preferred formulation embodiments of the invention was relatively high and ranged from 239 to 280 mg/ml (24 to 28% w/v). In certain aspects of the invention, the pharmaceutical composition has a terbinafine solubility ranging from about 10% to about 30% (w/v). In certain other aspects of the invention, the pharmaceutical composition has a terbinafine solubility of at least 10% (w/v), at least 15% (w/v), at least 20% (w/v), at least 25% (w/v), or at least 30% (w/v). In still other aspects of the invention, the pharmaceutical composition has a terbinafine solubility of at least 24% (w/v), at least 25% (w/v), at least 26% (w/v), at least 27% (w/v), or at least 28% (w/v).

Stability

In certain aspects, the topical formulations of the instant invention have the advantage of maintaining chemical and/or physical stability over time, even where the concentration of the active has been increased. In Tables 28-29 and 38-49, for instance, the chemical and physical attributes of preferred topical formulations were monitored over the course of a one- to six-month period.

In certain aspects invention, the pharmaceutical composition is substantially stable with respect to its chemical or physical attributes (or both) over a predetermined period of time. The measurable attributes may include, but are not limited to, pH, percentage of active, or visual attributes such as color and the presence of particulates. In other aspects the invention, the pharmaceutical composition is substantially stable following storage for about 4, 8, 12, 16, 20 or 24 weeks at 25° C. In still other aspects of the invention, the pharmaceutical composition is substantially stable following storage for about 4, 8, 12, 16, 20 or 24 weeks at 40° C.

Active Penetration and Retention

In certain aspects, select components of the formulation can function as penetration enhancers and, as a result, the formulation may display superior penetration abilities in comparison to a formulation with a similar concentration of active ingredient that contains no MPEs.

In certain other aspects, a formulation is designed for high penetration, for high retention in the skin or nail, or for both high penetration and high retention of the anti-fungal agent. The optimal formulation will have a balance between penetration and retention, enabling an effective amount of the active ingredient to pass through the skin or nail, but also enabling it to stay in the target area for a sufficient duration to achieve its intended effect upon the fungus.

In a preferred aspect, the topical formulations of the present invention provide nail retention of the anti-fungal agent which exceeds that provided by oral therapy. For example, Finlay has reported that in onychomycosis patients receiving oral terbinafine therapy (250 mg/day), concentrations of terbinafine in distal nail clippings were in the range of 0.25 to 0.55 ng/mg. See Finlay, A. Y. "Pharmacokinetics of terbinafine in the nail," *Br J Dermatol.* 1992, 126 Suppl 39:28-32. As evidenced in Tables 22-25 and 35 of the instant application, the concentration of terbinafine in test nails treated with the inventive formulations can reach at least 18 mcg/mg after 336 h, which is more than thirty times higher than that observed in the patients receiving oral therapy.

Thus, in a preferred aspect of the present invention, the permeation rate of the anti-fungal agent will be sufficient to provide concentrations of the agent in the nail that exceed those attained when the anti-fungal agent is administered orally. In more preferred aspects of the invention, concentrations of the anti-fungal agent achieved in the nail are at least 2-, 10-, 100-, 1000- or 10.000-fold greater than the level achieved by oral therapy to achieve effective treatment of onychomycosis. In alternative preferred aspects of the invention, concentrations of the anti-fungal agent achieved in the nail are at least 1-, 2-, 3-, 4-, 5-, 10-, 50-, 100-, 500-, 1000-, 2000-, 4000-, 5000-, or 10.000-fold greater than the level achieved by oral therapy to achieve effective treatment of onychomycosis.

IV. Methods of Preparation

In one aspect, the pharmaceutical composition is formulated as a cream, an emulsion, a microemulsion, a gel (e.g., a hydrogel, an organogel, or an inorganic or silica gel), a lotion, a lacquer, an ointment, a solution (e.g., a moderately to highly viscous solution), or a transdermal patch. See also U.S. Patent Application 2007/0224261 and U.S. Pat. No. 6,368,618. In a preferred aspect, the composition is a solution or a gel.

In an alternative preferred aspect, the composition is a lacquer or a patch. Although the permeation from a lacquer may be lower, it may be easier to incorporate MPEs. Another advantage is that it is possible that to obtain a formulation with high amount of active (e.g., up to 35%). MPEs may also be incorporated into various types of patches (e.g., adhesive, reservoir, and the like).

In one embodiment, the formulation is prepared by combining terbinafine with one or more MPEs (e.g., disodium cocoamphodiacetate (DCAM)). Optionally, urea and menthol or hexanetriol is added. The mixture is then dissolved in a combination of ethanol and water. After dissolution, lactic acid is added and the composition is vortexed. Ethyl acetate is then added followed by vortex mixing. Optionally, the cellulose thickener, film forming agent, or both can be added by vortex mixing.

V. Methods of Treatment

In certain embodiments, the invention describes a method for treating a fungal infection comprising the step of applying a topical anti-fungal composition to a subject to treat the fungal infection.

In certain aspects, the pharmaceutical composition is applied to a nail of the subject. In other aspects, the pharmaceutical composition is applied to the nail and the surrounding tissue of the nail of the subject. In another aspect, the pharmaceutical composition is applied to the skin of the subject.

In another aspect, the anti-fungal agent or other drug is delivered locally to the nail with minimal systemic absorption. In yet another aspect, the anti-fungal agent or other drug is delivered to and through the nail with minimal systemic absorption. In a still yet another aspect, the anti-fungal agent or other drug is delivered to the tissue surrounding or under the nail with minimal systemic absorption.

In another aspect, the anti-fungal agent or other drug is delivered locally to the skin with minimal systemic absorption. In yet another aspect, the anti-fungal agent or other drug is delivered to and through the skin with minimal systemic absorption. In a still yet another aspect, the anti-fungal agent or other drug is delivered to the tissue surrounding or under the area of skin application with minimal systemic absorption.

In other aspects, the subject is a human. Alternatively, the subject is a non-human mammal.

In still other aspects, the fungal infection is onychomycosis. In one aspect, the fungal infection is caused by *Trichophyton rubrum* or *Trichophyton interdigitale* (also known as *Trichophyton mentagrophytes*).

In yet still other aspects, the treatment is continued for at least 12 weeks. Preferably, the treatment is continued for at least six months. More preferably, the treatment is continued for at least 12 months.

In still other aspects, the treatment is applied one, two, three or four times a day for at least 1, 2, 3, 4, 5, 6 or 7 days. In alternative aspects, the treatment is applied once every 2 days, once every 3 days, once every 4 days, once every 5 days, once every 6 days or once every week. In still other aspects, the nail or tissue to which the treatment will be applied is cleaned and the remains of prior treatment are removed prior to fresh application of the treatment.

In further aspects, the time required for the composition to dry on the nail or skin is from about 1 to about 15 minutes. Preferably, the drying time is from about 2 to about 10 minutes. More preferably, the drying time is from about 5 to about 10 minutes. In one embodiment, the drying time is about 1, 2, 3, 4, 5, 6, 7, 8, 9, 10, 11, 12, 13, 14 or 15 minutes. Notably, such drying times can improve patient compliance.

Compositions of the present invention may, if desired, be presented in a spray, bottle, jar, roll-on, brush-on, or other container-closure system acceptable to the FDA or other regulatory bodies, which may contain one or more unit dosage forms containing the active ingredient. The package or dispenser may also be accompanied by a notice associated with the container in a form prescribed by a governmental agency regulating the manufacture, use, or sale of pharmaceuticals, the notice indicating approval by the agency.

Compositions of the present invention are useful and effective when applied topically to treat the fungal infection. The amount of the compound present in the composition will be the amount that is therapeutically effective, i.e. an amount that will result in the effective treatment of the onychomycosis when applied.

The therapeutically effective amount will vary depending on the subject and the severity of the affliction and can be determined routinely by one of ordinary skill in the art. In some embodiments, the composition is a liquid or semisolid, such as a cream, ointment, lotion, lacquer, or gel (preferably a gel) having a solvent in which the antifungal compound (or other nail medicament, when used), or its salt, is dissolved. Thus, the composition will contain at least the antifungal compound, a solvent for the compound, and a gelling agent.

Preferably, the composition is water-based, which means that the solvent is preferably water-miscible. In addition, the composition may include a surfactant to aid in the delivery of the antifungal through the nail plate; a film-forming agent; a buffering agent to adjust the pH of the composition; and an adherence-promoting agent to assist in adhering the composition to the nail plate. The composition may be applied directly to the nail or applied in an absorbent pad.

VI. EXAMPLES

Below, embodiments of the present invention will be described by way of examples, which are provided for illustrative purposes only. Accordingly, they are not to be construed as limiting the scope of the present invention as defined by the appended claims. Unless otherwise specified, the percentage specified is a weight/weight percentage.

The effect of the inventive formulations containing an exemplary active anti-fungal agent (terbinafine) on transdermal permeation and skin retention was examined through shed snake skin or bovine hoof as model membranes. Permeation and nail retention studies were also carried out with human cadaver nails and human nail clippings, respectively. For permeation studies, each formulation was tested in fivefold replicate. Formulation C of Table 3 from U.S. Pat. No. 7,462,362 (Control 1), also referred to as F24 (Control 1) herein, and Lamisil® cream (Control 2), also referred to as F40 (Lamisil®) or F40 (Control 2) herein, were used as the controls.

A. General Procedure for Formulation Preparation

For a typical DCAM-containing composition, the formulation is prepared as follows:
1. Combine terbinafine hydrochloride and disodium cocoamphodiacetate (DCAM).
2. Optionally add urea and menthol or hexanetriol.
3. Dissolve the mixture in a combination of a proportion of the ethanol and the water.
4. After dissolution, add lactic acid. Vortex for 2-3 minutes.
5. Add ethyl acetate and then add the remainder of the ethanol and the water. Vortex for 2-3 minutes.
6. Slowly add the cellulose thickener (e.g., HPC HY117) and/or film forming agent (e.g., Eudragit L100-55) while vortexing.
7. Continue vortexing the mixture thoroughly for about 30 minutes or until a clear and homogenous system forms.

For a typical carnitine-containing composition, the formulation is prepared as follows:
1. Carnitine hydrochloride was weighed into an appropriate container.
2. Acetyl carnitine was weighed and quantitatively transferred into the container with carnitine.
3. To this container was added terbinafine hydrochloride.
4. Approximately half of the amount of ethanol was added and thoroughly mixed.
5. Menthol was added to the container and mixed.
6. Lactic acid and water were added to the system and mixed.
7. A 60% aqueous solution of ammonium thioglycolate was carefully transferred into the container and mixed.
8. The remaining ethanol was added to obtain a clear solution. The solution was mixed for 10 minutes.
9. Hydroxypropyl cellulose was slowly added and stirred vigorously until a homogenous dispersion is formed.
10. The resulting formulation was blanketed with nitrogen and kept in amber colored bottles protected from light.

B. General Methods for Transdermal and Transungual Experiments

Shed snakeskin was used as a model membrane as it is composed of keratinaceous material similar to a nail. In addition, experiments were performed on bovine hoof and human cadaver nails. Analysis of receptor cell matrix to determine the amount of API permeating through the nail was carried out on an Agilent 1100 HPLC. An isocratic elution method was used in conjunction with acetonitrile and an ion-pairing reagent at pH 3.0 phosphate buffer as mobile phase on a Zorbax Reverse-Phase C8 column.

1. Shed Snakeskin

Franz cells with a 3-mL receptor well volume were used in conjunction with shed snakeskin. The donor well had an area of circa 0.55 cm². Receptor wells were filled with isotonic phosphate buffered saline ("PBS") with a pH of 5.5. The flanges of the Franz cells were coated with vacuum grease to ensure a complete seal and were clamped together with uniform pressure. After the Franz cells were assembled, the skin was allowed to pre-hydrate for about 45 minutes. The dosing level was 100 µl. The Franz cells were maintained at 32° C. by placement in a humidified incubator, and the receptor wells of the Franz cells were stirred with a stir bar. Sample aliquots were drawn from the receptor wells at varying time points and replaced with fresh buffer. Measurements for each formulation were carried out in five-fold replicate. The concentration of the active in the sample aliquots was analyzed using HPLC.

2. Bovine Hoof Slices

The cleaned bovine hooves were obtained locally. Only the sole part of bovine hoof was used in the present studies. The hooves were submerged for 3 days in distilled water. They were sliced in layers of 0.5-1 mm thickness with a sharp knife. The layers were punched out to a diameter of about 15 mm and kept in distilled water until use. Receptor cells were filled with pH 5.5 buffered saline, and a small magnet was placed in the cell. The punched pieces were mounted on the receptor cells with silicone glue. After the same glue was applied to the flanges of donor cells, the compartments were clamped. Following the application of formulations, the cells were kept at 32° C. with stirring. Samples were taken at predetermined intervals and assayed by HPLC.

3. Human Cadaver Nails

Human cadaver nails were obtained from a tissue bank and were kept in a freezer until use. The nails were removed from the freezer and soaked in physiological buffer solution for several hours before starting the assay. Any residual tissue on the ventral side was removed. Receptor cells were filled with pH 5.5 buffer saline, and a small magnet was placed in the cell. The punched pieces were mounted on the receptor cells with silicone glue. After the same glue was applied to the flanges of donor cells, the compartments were clamped. Following the application of the formulations, the cells were kept at 32° C. with stirring. Samples were taken at predetermined intervals and assayed by HPLC.

Human cadaver great toenails selected for the tests were soaked in physiological buffer solution for several hours before the assay. Nails were prepared for the assay by removal of epidermal residues on the ventral side. Round nail discs of 16 mm diameter were punched. For the laser pretreated nails, the perforated area had a diameter of 13 mm. Nails were masked on the dorsal side by a silicon mounting ring leaving a nail area of 10 mm in diameter where the nails were exposed to the pharmaceutical composition and the protective layer.

C. General Method for Skin Retention Studies

1. Shed SnakeSkin:

At the end of the permeation study, skin samples were removed from the Franz cells for skin retention studies. Any excess of formulation was carefully wiped away, first with cotton swabs and then with lint-free paper. For the shed snake skin studies, the skin samples were quickly washed with cold water and ethanol, and the skin samples were then dried for 1 h at room temperature. After being cut into small pieces with a pair of stainless steel scissors, the samples were transferred into 5 mL scintillation vials, and 2 mL of absolute ethanol was added. The mixtures were homogenized with a laboratory homogenizer (PRO 250 from PRO Scientific, Oxford Conn.) for approximately 2 min. During this process, extra care was taken to avoid any excessive temperature increase. The homogenate was filtered through 9 mm diameter disposable syringe filters (0.45 µm, Acrodisc®). The filtrate, after appropriate dilution, was assayed by HPLC.

2. Bovine Hoof Slices and Nails:

For retention studies from bovine hoof slices and nails, any excess of formulation was carefully wiped away with a lint free tissue. The samples were quickly washed with an ethanol/water mixture and dried at room temperature for 1 hour. After being cut in small pieces, they were quantitatively transferred into 5 mL scintillation vials, and 2 mL of absolute ethanol was added. The samples were left overnight in the dark at room temperature with occasional shaking. The solution was then filtered through a 9-mm-diameter disposable syringe filter (0.45 µm, Acrodisc®). A sample of the filtrate, after appropriate dilution, was assayed by HPLC.

3. Nail Clippings:

Retention studies were also performed using nail clippings. The nail clippings were washed twice with distilled water and dried at room temperature with 40% humidity until the clippings were constant weight. The weighed nail clippings were transferred into 5-mL scintillation vials, and a known amount of formulation was added. After 24 hours at room temperature, the nail clippings were removed and cleaned. They were quickly washed with an ethanol-water mixture and dried at room temperature for 1 hour. After being cut in small pieces, they were quantitatively transferred into 5-mL scintillation vials, and 2 mL of absolute ethanol was added. The samples were left overnight in the dark at room temperature with occasional shaking. The solution was then filtered through a 9-mm-diameter disposable syringe filter (0.45 µm, Acrodisc®). After appropriate dilution of the filtrate, a sample was assayed by HPLC.

Results from these studies and formulations used are described in the following Examples.

Example 1

Permeation Profiles of Terbinafine Formulations I

TABLE 1

Permeation Profiles of Terbinafine Formulations I

| Ingredients | F24 | F2 | F3 | F4 | F5 | F6 | F7 | F8 | F9 |
|---|---|---|---|---|---|---|---|---|---|
| Terbinafine hydrochloride | Control 1 | 12.5 | 16.7 | 16.7 | 16.7 | 16.7 | 16.7 | 12.5 | 13.3 |
| Disodium cocoamphodiacetate | | 12.5 | 16.7 | 8.3 | | | 16.7 | 12.5 | 13.3 |
| Ethanol | | 50 | 41.7 | 58.3 | 66.7 | 66.7 | 50 | 43.8 | 33.3 |
| Caprylic acid | | | 8.3 | | | | | | 6.7 |
| Urea | | 12.5 | | | | | | | 13.3 |

TABLE 1-continued

Permeation Profiles of Terbinafine Formulations I

| Ingredients | F24 | F2 | F3 | F4 | F5 | F6 | F7 | F8 | F9 |
|---|---|---|---|---|---|---|---|---|---|
| Water |  | 12.5 | 16.6 | 16.6 | 16.7 | 16.7 | 16.7 | 12.5 | 13.3 |
| Polyvinylpyrrolidone 30 |  |  |  |  |  |  |  | 6.25 | 6.7 |

Table 16 FI = F3

Figure 1B:
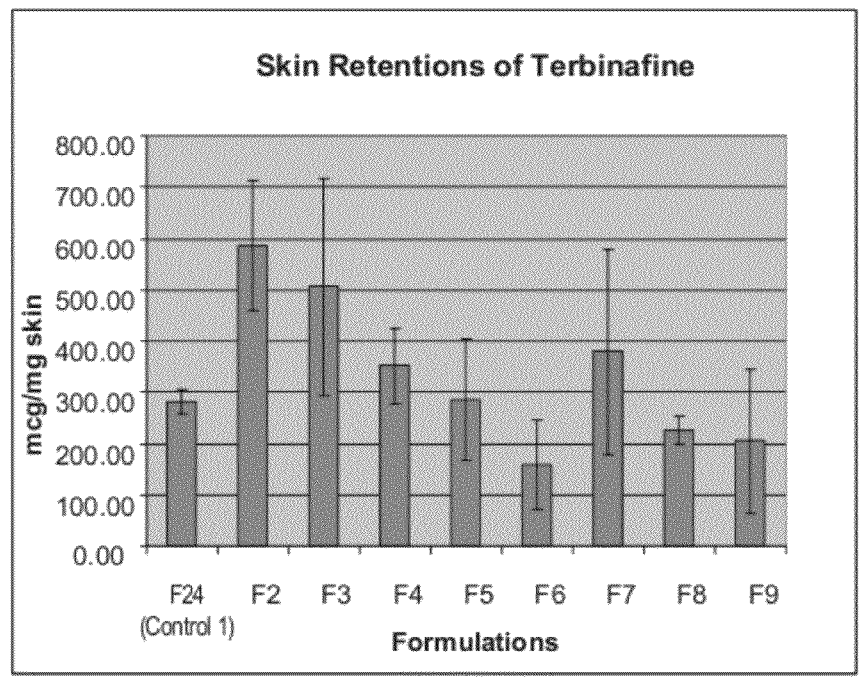

The results are shown in FIGS. 1A and 1B. Formulation F3 contains disodium cocoamphodiacetate (DCAM) and caprylic acid, whereas formulation F7 contains no acid. The results suggests that the two ingredients show synergistic activity.

Example 2

Permeation Profiles of Terbinafine Formulations II

TABLE 2

Permeation Profiles of Terbinafine Formulations II

| Ingredients | F11 | F12 | F13 | F14 | F15 | F16 | F17 | F18 | F19 |
|---|---|---|---|---|---|---|---|---|---|
| Terbinafine hydrochloride | 10 | 10 | 10 | 10 | 10 | 10 | 10 | 10 | 10 |
| Disodium cocoamphodiacetate | 15 | 15 | 15 | 15 | 15 | 15 | 15 |  |  |
| Ethanol | 52 | 39 | 45 | 42 | 42 | 46 | 44 | 57.5 | 52.5 |
| Caprylic acid |  | 6 |  |  |  |  |  |  |  |
| Urea | 15 | 15 | 15 | 15 | 15 | 15 | 15 | 15 | 15 |
| Water | 8 | 15 | 10 | 8 | 8 | 8 | 10 | 10 | 10 |
| Menthol |  |  | 5 |  |  |  |  |  | 5 |
| Propylene glycol |  |  |  | 10 |  |  |  |  |  |
| Transcutol |  |  |  |  | 10 |  |  |  |  |
| Lactic acid |  |  |  |  |  | 6 |  |  |  |
| Potassium thioglycolate |  |  |  |  |  |  | 6 |  |  |
| Sodium docusate |  |  |  |  |  |  |  | 7.5 | 7.5 |

Table 16 FII = F13

Figure 2A:
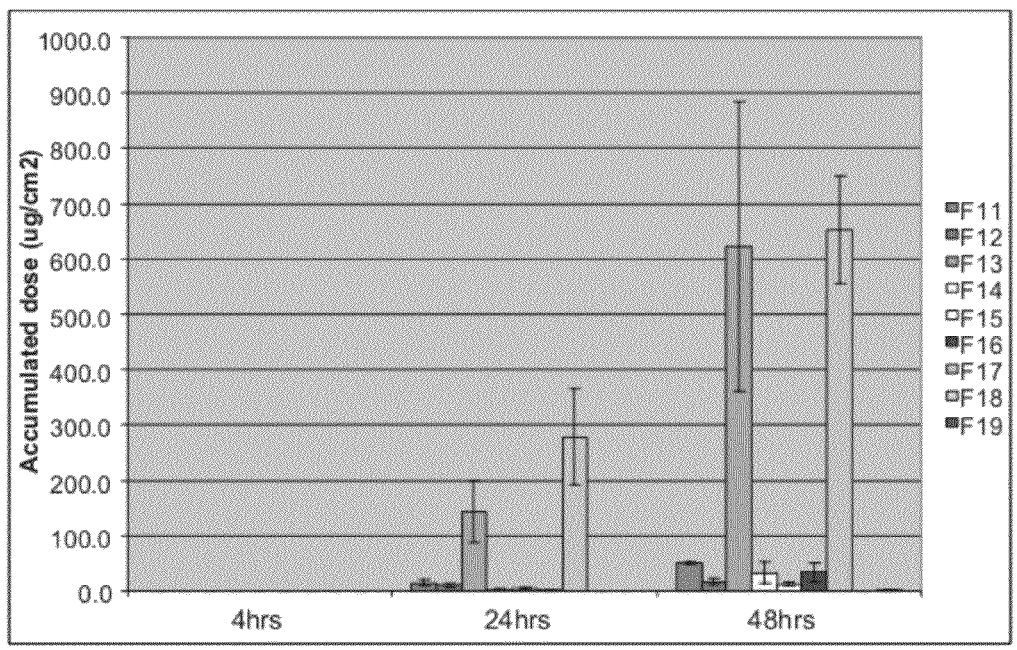
FIGS. 2A and 2B illustrate the results of shed snakeskin permeation studies on the formulations of Table 2.
Figure 2B:
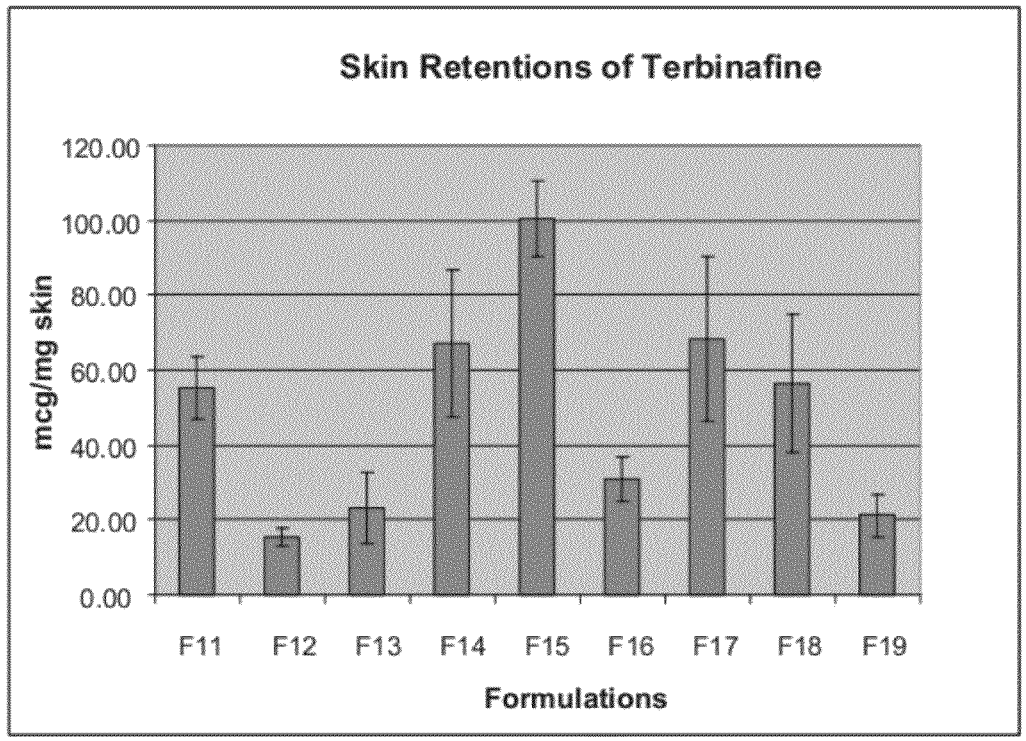

The results are shown in FIGS. 2A and 2B. Formulation F13 contains menthol in addition to DCAM and urea (F11) and shows higher permeation. The results also suggest that DCAM, urea, and menthol show synergistic activity.

Example 3

Permeation Profiles of Terbinafine Formulations III

TABLE 3

Permeation Profiles of Terbinafine Formulations III

| Ingredients | F21 | F22 | F23 | F24 | F40 |
|---|---|---|---|---|---|
| Terbinafine hydrochloride | 10 | 10 | 10 | Control 1 | Control 2 |
| Disodium cocoamphodiacetate | 15 | 15 | 15 |  |  |
| Ethanol | 40 | 39.5 | 40 |  |  |
| Urea | 15 | 15 | 15 |  |  |
| Water | 14 | 8 | 14 |  |  |
| Menthol |  | 5 |  |  |  |
| Panthenol |  | 7.5 |  |  |  |

TABLE 3-continued

Permeation Profiles of Terbinafine Formulations III

| Ingredients | F21 | F22 | F23 | F24 | F40 |
|---|---|---|---|---|---|
| Potassium thioglycolate | 6 |  |  |  |  |
| Ammonium thioglycolate |  |  | 6 |  |  |

Table 16 FIII = F22

Figure 3A:
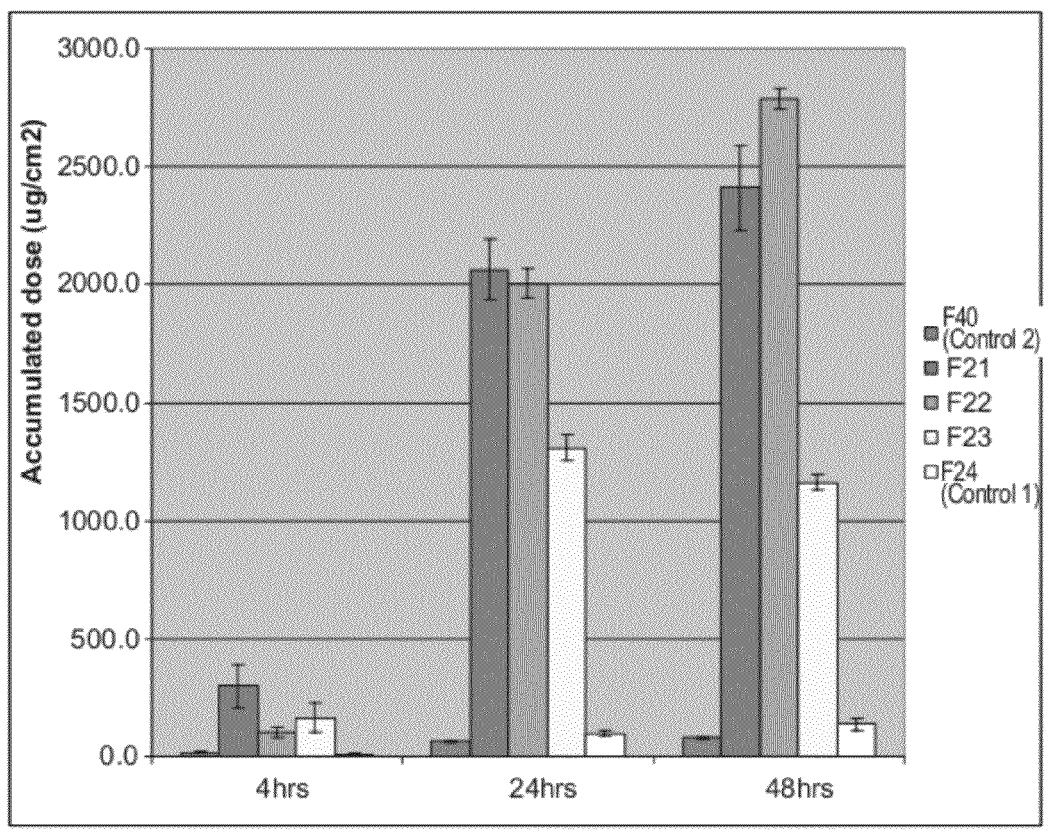
FIGS. 3A and 3B illustrate the results of shed snakeskin permeation studies on the formulations of Table 3.
Figure 3B:
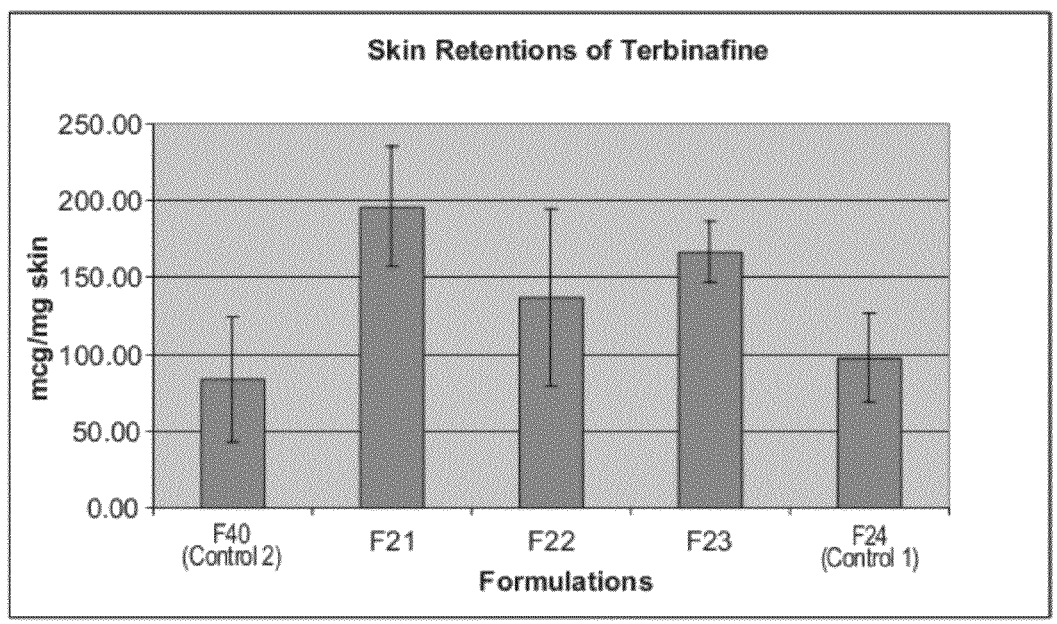

The results are shown in FIGS. 3A and 3B. Although F21 with potassium thioglycolate gives better permeation than F23, further studies were switched to the ammonium salt version due to its easier formulation. In later studies, higher permeation was also observed.

Example 4

Permeation Profiles of Terbinafine Formulations IV

TABLE 4

Permeation Profiles of Terbinafine Formulations IV

| Ingredients | F31 | F32 | F33 | F34 | F35 | F36 | F37 | F38 | F39 |
|---|---|---|---|---|---|---|---|---|---|
| Terbinafine hydrochloride | 10 | 10 | 10 | 10 | 10 | 10 | 10 | 10 | 10 |
| Disodium cocoamphodiacetate | 15 | | 15 | | 15 | | | | |
| Ethanol | 44 | 57 | 57 | 64 | 41 | 45 | 58 | 50 | 39 |
| Isethionate | | | | | | 10 | 10 | 10 | 10 |
| Urea | 15 | 15 | | | 15 | 15 | | | 15 |
| Water | 10 | 12 | 12 | 20 | 8 | 20 | 22 | 22 | 20 |
| Menthol | | | | | 5 | | | | |
| Potassium thioglycolate | 6 | 6 | 6 | 6 | 6 | | | 6 | 6 |

Figure 4A:
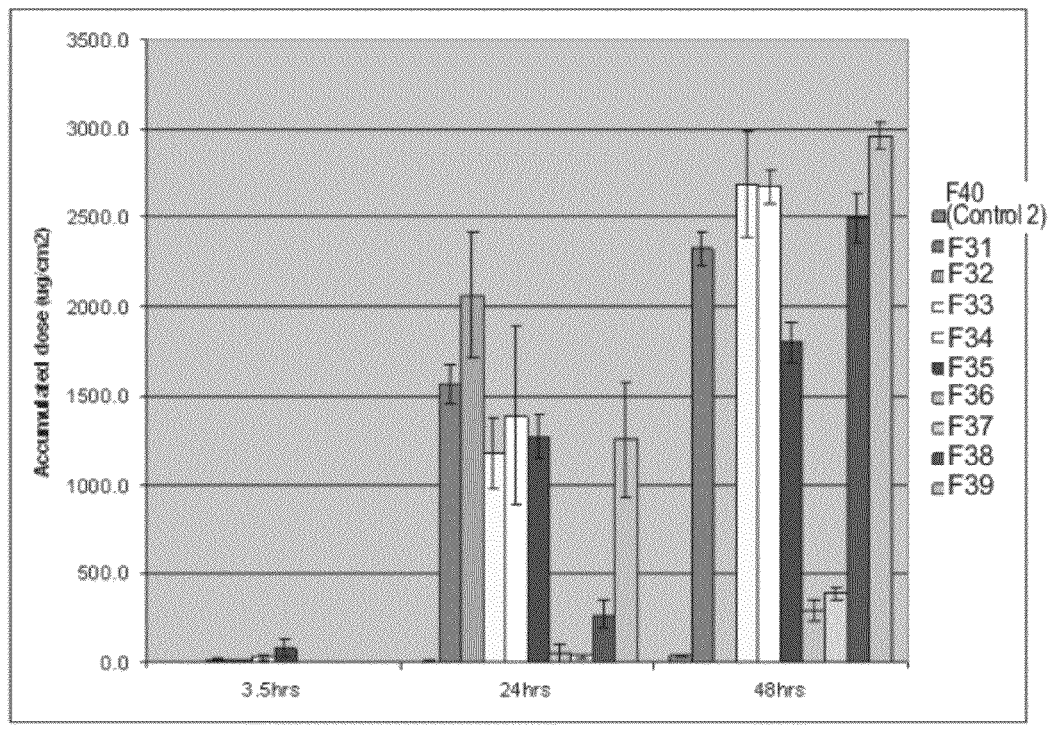
FIGS. 4A and 4B illustrate the results of shed snakeskin permeation studies on the formulations of Table 4.
Figure 4B:
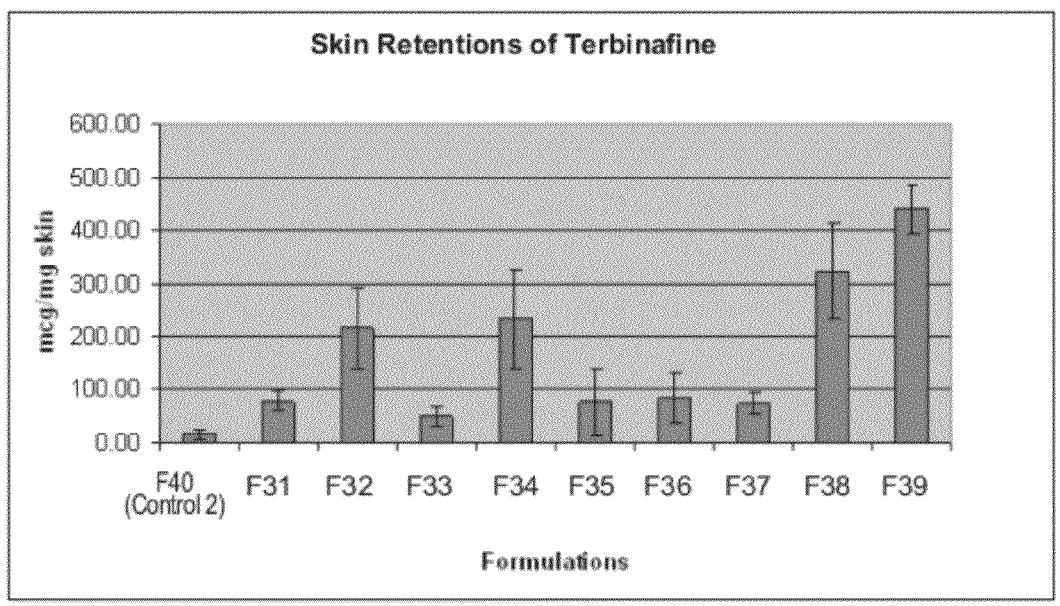

The results are shown in FIGS. 4A and 4B. In this experiment, combinations of DCAM with thioglycolate or thioglycolate with isethionate and urea (F39) were first examined. This experiment used multiple infinite dose applications.

Example 5

Bovine Hoof Permeation of Terbinafine Formulation V

TABLE 5

Bovine Hoof Permeation of Terbinafine Formulation V

| Ingredients | F22 | F24 | F40 |
|---|---|---|---|
| Terbinafine hydrochloride | 10 | Control 1 | Control 2 |
| Disodium cocoamphodiacetate | 15 | | |
| Ethanol | 39.5 | | |
| Urea | 15 | | |
| Water | 8 | | |
| Menthol | 5 | | |
| D-Panthenol | 7.5 | | |

Table 16 FIII = F22

Figure 5:
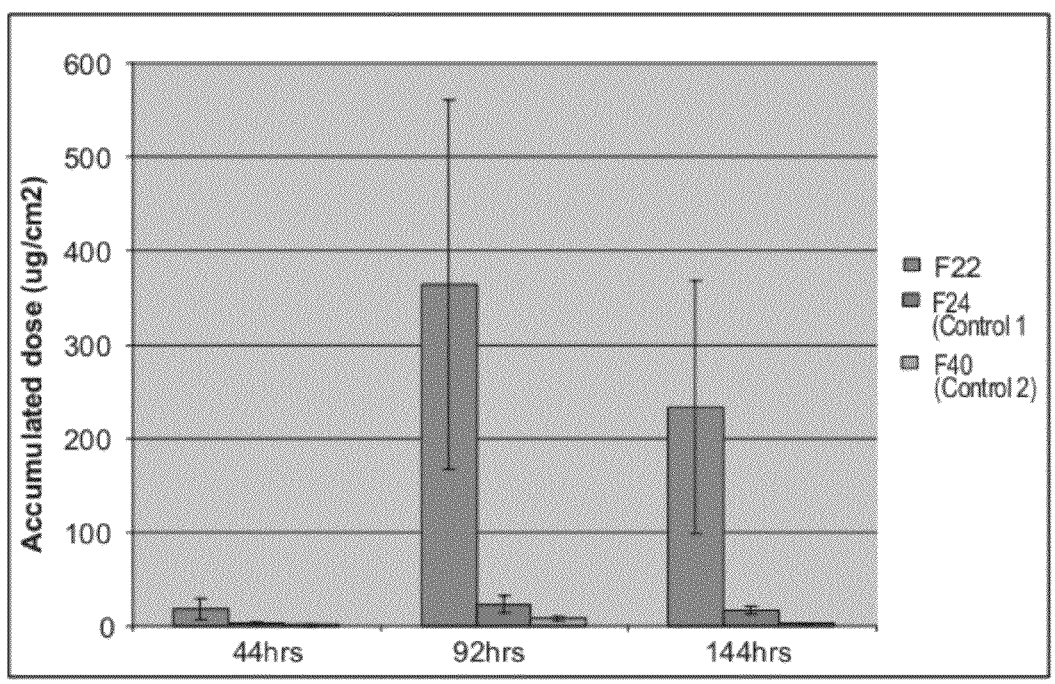
FIG. 5 illustrates the results of bovine hoof studies on the formulations of Table 5.

The results are shown in FIG. 5. A DCAM/urea/panthenol formulation was tested using the bovine hoof model

Example 6

Permeation Profiles of Terbinafine Formulations VI

TABLE 6

Permeation Profiles of Terbinafine Formulations VI

| Ingredients | F41 | F42 | F43 | F44 | F45 | F46 | F47 | F48 | F49 |
|---|---|---|---|---|---|---|---|---|---|
| Terbinafine hydrochloride | 10 | 10 | 10 | 10 | 10 | | 10 | 10 | 10 |
| Disodium cocoamphodiacetate | 15 | | 15 | 15 | 15 | | | | |
| Ethanol | 30 | 45 | 45 | 45 | 35 | 55 | 42 | 50 | 40 |
| Urea | 15 | 15 | | 15 | 15 | | 15 | 20 | 20 |
| Water | 10 | 10 | 10 | 10 | 10 | 10 | 8 | 10 | 10 |
| Acetylcarnitine | 7.5 | 7.5 | 7.5 | | 7.5 | 7.5 | 7.5 | | |
| Carnitine | 7.5 | 7.5 | 7.5 | | 7.5 | 7.5 | 7.5 | | |
| Menthol | 5 | 5 | 5 | 5 | | | | | |
| Betaine | | | | | | | | 10 | 10 |
| Ammonium thioglycolate (60% aqueous solution) | | | | | | 10 | 10 | | 10 |

Figure 6A:
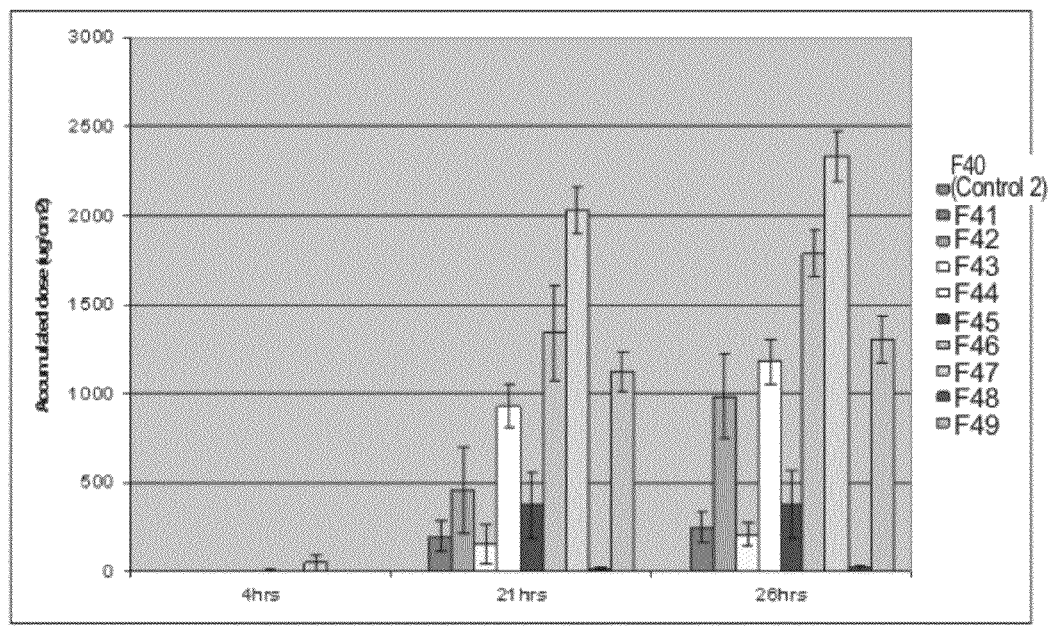
FIGS. 6A and 6B illustrate the results of shed snakeskin permeation studies on the formulations of Table 6.
Figure 6B:
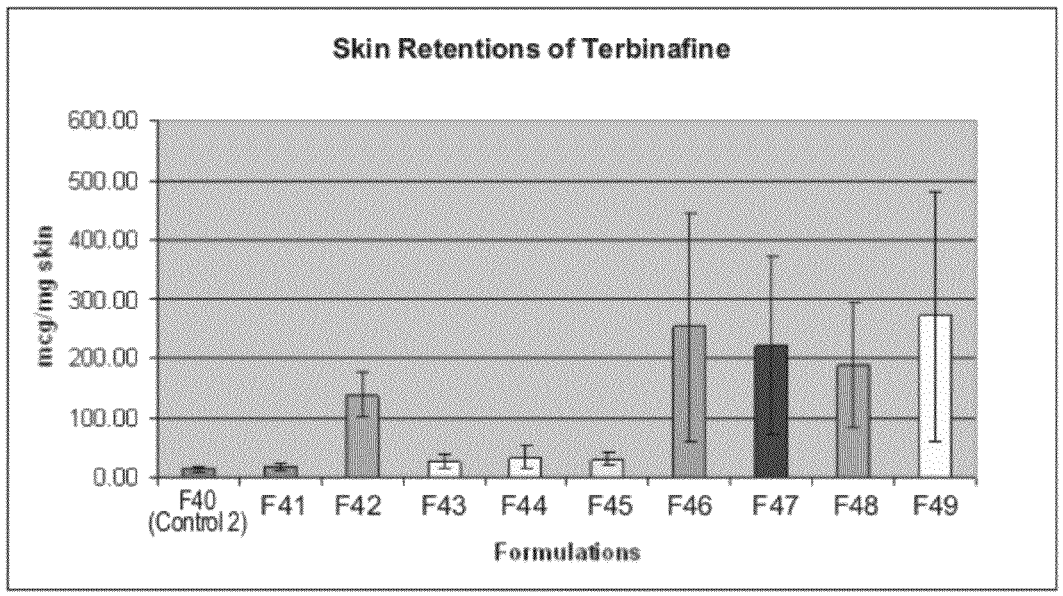

The results are shown in FIGS. 6A and 6B. Data suggest that DCAM and carnitine combinations are less effective than thioglycolate/carnitine combinations. Urea may be less beneficial for thioglycolate/carnitine combinations. Therefore, these combinations were not pursued.

Example 7

Permeation Profiles of Terbinafine Formulations VII

TABLE 7

Permeation Profiles of Terbinafine Formulations VII

| Ingredients | F40 | F51 | F52 | F53 | F54 | F55 | F56 | F57 | F58 | F24 |
|---|---|---|---|---|---|---|---|---|---|---|
| Terbinafine hydrochloride | Control 2 | 10 | 10 | 10 | 10 | 10 | 10 | 10 | 10 | Control 1 |
| Disodium cocoamphodiacetate | | 20 | 20 | 20 | | 20 | 20 | 20 | 20 | |
| Ethanol | | 47.5 | 50 | 55 | 67.5 | 45 | 30 | 45 | 45.5 | |
| Caprylic acid | | 7.5 | | | 7.5 | | | 7.5 | 7.5 | |
| Water | | 15 | 12.5 | 15 | 15 | 12.5 | 12.5 | 12.5 | 15 | |
| Lactic acid | | | 7.5 | | | 7.5 | 7.5 | | | |
| Menthol | | | | | | 5 | | 5 | | |
| Ethyl acetate | | | | | | | 20 | | | |
| Hydroxypropyl cellulose | | | | | | | | | 2 | |

Table 16 FIV = F52
Table 16 FV = F56

Figure 7A:
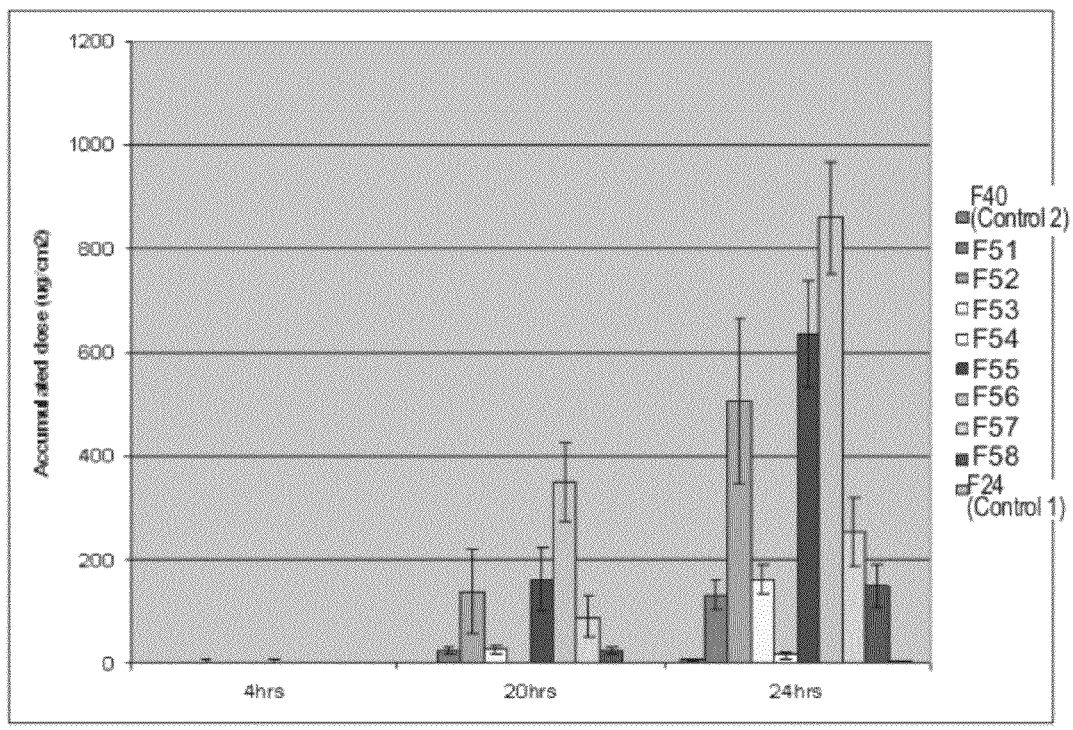
FIGS. 7A and 7B illustrate the results of shed snakeskin permeation studies on the formulations of Table 7.
Figure 7B:
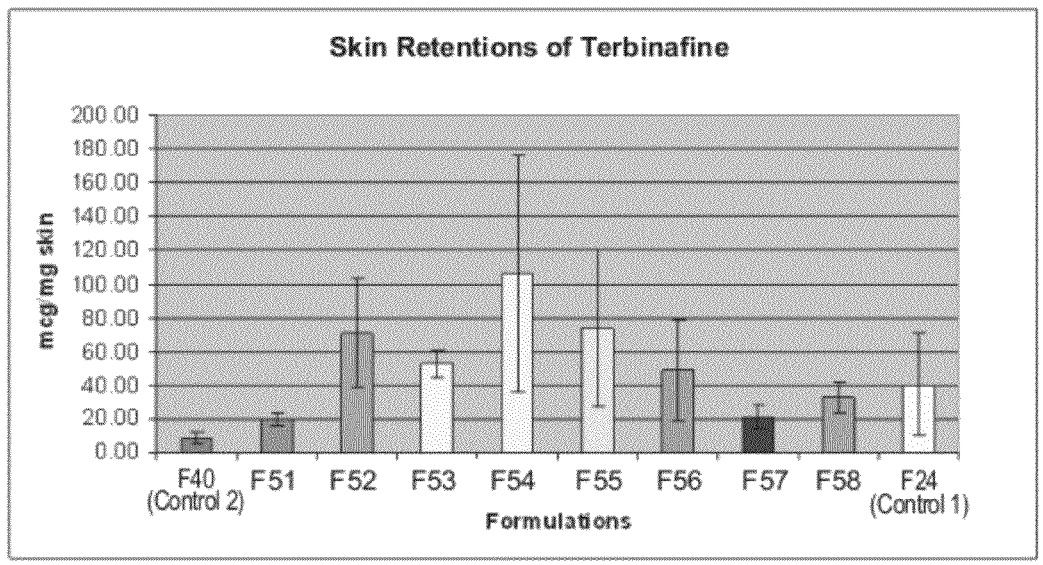

The results are shown in FIGS. 7A and 7B. Lactic acid showed higher permeation than caprylic acid (F52 vs. F51).

Example 8

Permeation Profiles of Terbinafine Formulations VIII

TABLE 8

Permeation Profiles of Terbinafine Formulations VIII

| Ingredients | F61 | F62 | F63 | F64 | F65 | F66 | F67 | F68 | F69 |
|---|---|---|---|---|---|---|---|---|---|
| Terbinafine hydrochloride | 10 | 10 | 10 | 10 | 10 | 10 | 10 | 10 | 10 |
| Disodium cocoamphodiacetate | 15 | | 15 | 15 | 15 | 15 | | | |
| Ethanol | 40 | 52.5 | 47.5 | 45 | 47.5 | 40 | 50 | 45 | 50 |
| Urea | 15 | 15 | | 15 | 15 | 15 | 15 | 15 | 15 |
| Water | 7.5 | 10 | 15 | 7.5 | 7.5 | 7.5 | 7.5 | 12.5 | 7.5 |
| Menthol | 5 | 5 | 5 | | 5 | | 5 | 5 | 5 |
| D-Panthenol | 7.5 | 7.5 | 7.5 | 7.5 | | | 7.5 | 7.5 | 7.5 |
| Thymol | | | | | | 5 | | | |
| Sodium laureth sulfate | | | | | | | 5 | | |
| Cetyl trimethylammonium chloride | | | | | | | | 5 | |
| Tween 80 | | | | | | | | | 5 |

Figure 8A:
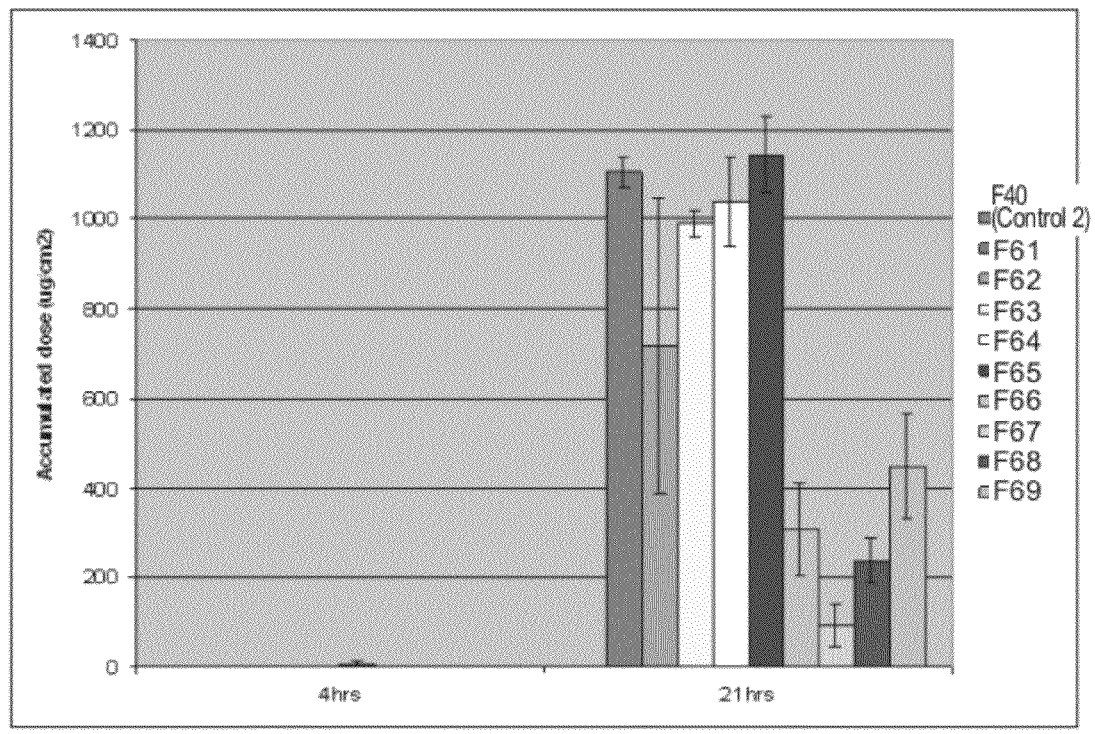
FIGS. 8A and 8B illustrate the results of shed snakeskin permeation studies on the formulations of Table 8.
Figure 8B:
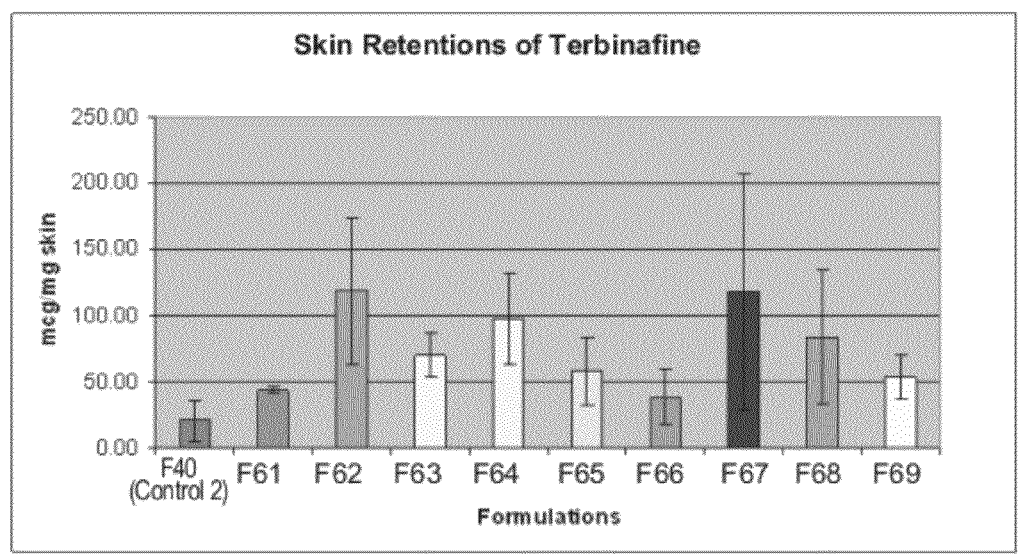

The results are shown in FIGS. 8A and 8B. Replacing DCAM with an anionic detergent (sodium lauryl sulfate), a cationic detergent (cetyl trimethylammonium chloride), or a nonionic detergent (Tween 80) reduced the delivery (F67, F68, and F69 vs. F61).

Using thymol instead of menthol also reduced the permeation (F66 vs. F61).

Example 9

Permeation Profiles of Terbinafine Formulations IX

TABLE 9

Permeation Profiles of Terbinafine Formulations IX

| Ingredients | F71 | F72 | F73 | F74 | F75 | F76 | F77 | F78 | F79 | F80 |
|---|---|---|---|---|---|---|---|---|---|---|
| Terbinafine hydrochloride | 10 | 10 | 10 | 10 | 10 | 10 | 10 | 10 | 10 | 10 |
| Disodium cocoamphodiacetate | 20 | 20 | 20 |  |  |  | 20 | 20 |  |  |
| Ethanol | 30 | 30 | 30 | 45 | 45 | 45 | 25 | 25 | 50 | 35 |
| Ethyl acetate | 20 | 18 | 18 | 20 | 20 | 20 | 10 | 5 | 20 | 20 |
| Water | 12.5 | 12.5 | 12.5 | 12.5 | 12.5 | 12.5 | 12.5 | 12.5 | 12.5 | 12.5 |
| Lactic acid | 7.5 | 7.5 | 7.5 | 7.5 | 7.5 | 7.5 | 7.5 | 7.5 | 7.5 | 7.5 |
| Urea |  |  |  |  |  |  | 15 | 15 |  | 15 |
| Menthol |  |  |  |  |  |  |  | 5 |  |  |
| Polyvinylpyrrolidone 30 |  |  | 2 |  |  |  |  |  |  |  |
| Hydroxypropyl cellulose HY117 |  | 2 |  |  |  |  |  |  |  |  |
| Sodium laureth sulfate |  |  |  | 5 |  |  |  |  |  |  |
| Cetyl trimethylammonium chloride |  |  |  |  | 5 |  |  |  |  |  |
| Tween 80 |  |  |  |  |  | 5 |  |  |  |  |

Table 16 FVI = F78

Figure 9:
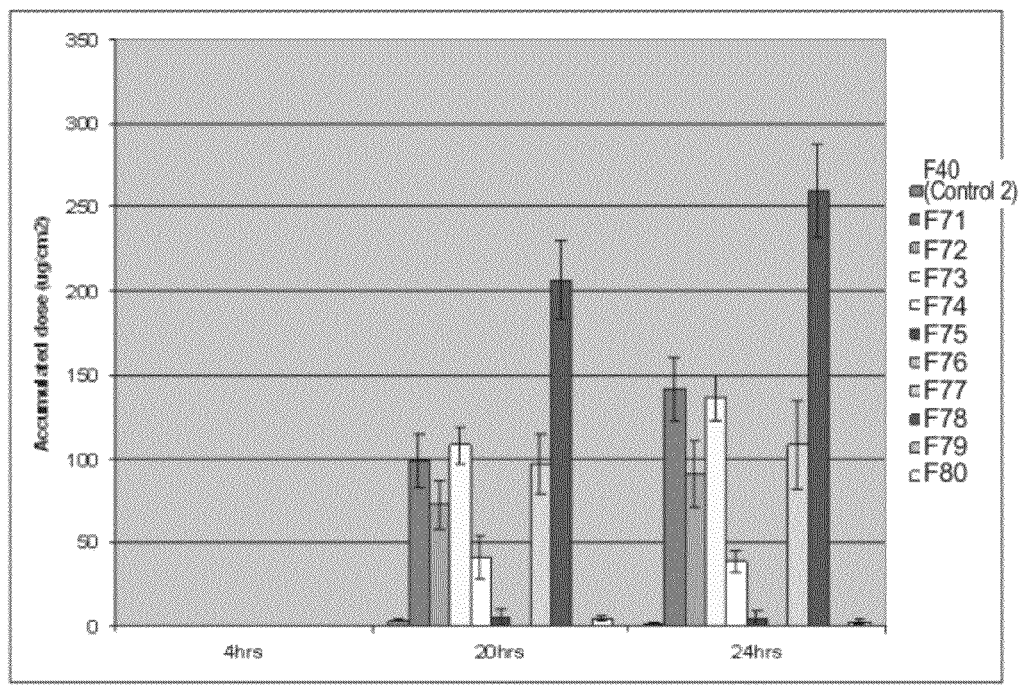
FIG. 9 illustrates the results of shed snakeskin permeation studies on the formulations of Table 9.

The results are shown in FIG. 9. Addition of urea and menthol to the DCAM/lactic acid chassis caused further permeation enhancement (F71 vs. F78).

Example 10

Permeation Profiles of Terbinafine Formulations X

TABLE 10

Permeation Profiles of Terbinafine Formulations X

| Ingredients | F81 | F82 | F83 | F84 | F85 | F86 | F87 | F88 | F89 |
|---|---|---|---|---|---|---|---|---|---|
| Terbinafine hydrochloride | 10 | 10 | 10 | 10 | 10 | 10 | 10 | 10 | 10 |
| Disodium cocoamphodiacetate | 20 | 20 | 20 | 20 | 20 | 10 | 10 | 10 | 20 |
| Ethanol | 22.5 | 30 | 13 | 21 | 25 | 30 | 30 | 35 | 20 |
| Ethyl acetate | 7.5 | 2.5 | 7 | 7.5 | 5 | 10 | 15 | 15 | 7.5 |
| Water | 12.5 | 10 | 12.5 | 12.5 | 10 | 12.5 | 12.5 | 12.5 | 7.5 |
| Lactic acid | 7.5 |  | 7.5 | 7.5 | 7.5 | 7.5 | 7.5 | 7.5 | 15 |
| Urea | 15 | 15 | 15 | 15 | 15 | 15 | 10 | 5 | 15 |
| Menthol | 5 | 5 | 5 | 5 | 7.5 | 5 | 5 | 5 | 5 |
| Caprylic acid |  | 7.5 |  |  |  |  |  |  |  |
| Isopropanol |  |  | 15 |  |  |  |  |  |  |
| Polyvinylpyrrolidone |  |  |  | 1 |  |  |  |  |  |
| Hydroxypropylcellulose HY117 |  |  |  | 1 |  |  |  |  |  |

Table 16 FVII = F81
Table 16 FVIII = F87

Figure 10A:
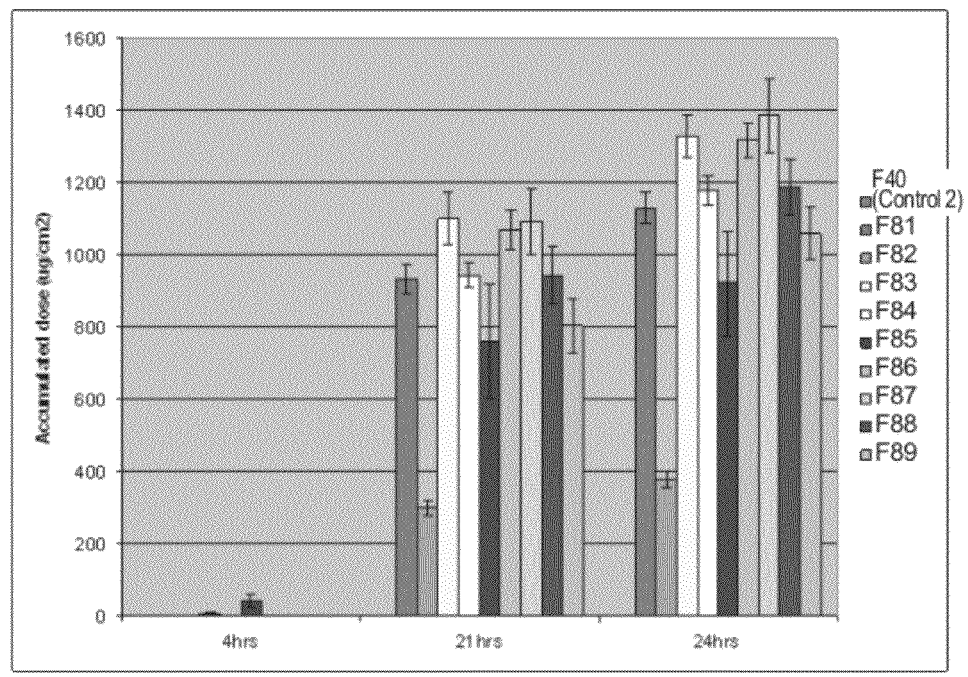
FIGS. 10A and 10B illustrate the results of shed snakeskin permeation studies on the formulations of Table 10.
Figure 10B:
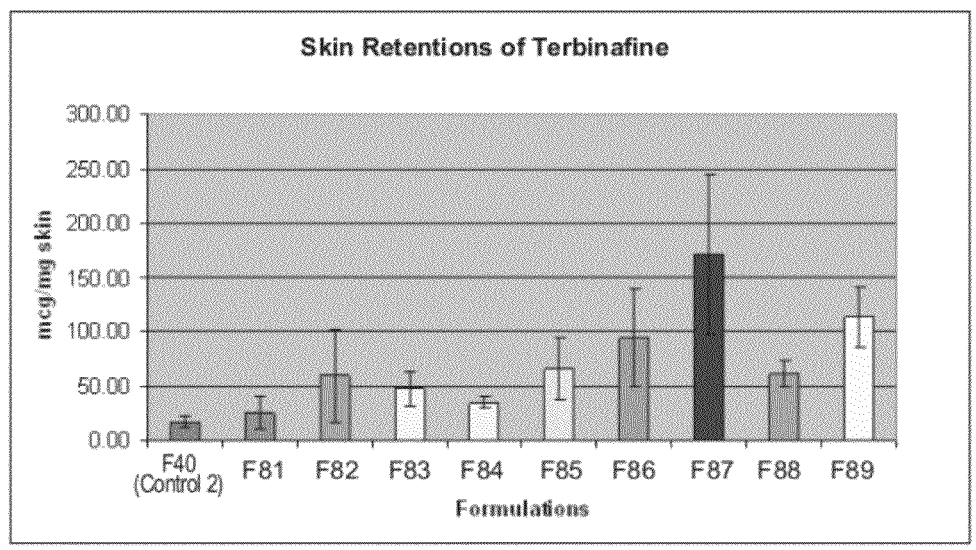

The results are shown in FIGS. 10A and 10B. The reduction of urea level from 15% (F81) to 10% (F87) did not reduce the delivery.

Increasing the amount of lactic acid from 7.5% (F81) to 15% (F89) did not influence the permeation.

Example 11

Retention of Terbinafine from Human Nail Clippings XI

TABLE 11

Retention of Terbinafine from Human Nail Clippings XI

| | Formulations | |
|---|---|---|
| Ingredients | F24 | F100 |
| Terbinafine hydrochloride | Control 1 | 10 |
| Ethanol | | 32.5 |
| Ethyl acetate | | 15 |
| Disodium cocoamphodiacetate | | 10 |
| Water | | 12.5 |
| Lactic acid | | 5 |
| Urea | | 10 |
| Menthol | | 5 |

Table 16 FIX = F100

Figure 11:
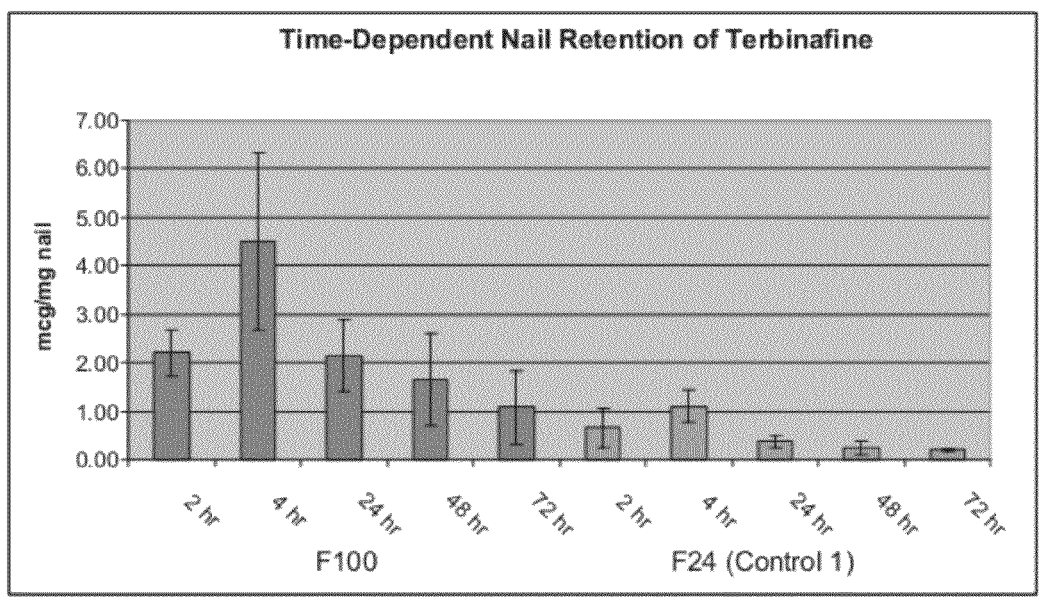
FIG. 11 illustrates the results of human nail retention studies on the formulations of Table 11.

The results are shown in FIG. 11. The retention of terbinafine from formulation FIX (F100) in human nail clippings is higher than the control.

Example 12

Bovine Hoof Permeation of Terbinafine Formulation XII

TABLE 12

Bovine Hoof Permeation of Terbinafine Formulation XII

| | Formulations | | |
|---|---|---|---|
| Ingredients | F22 | F24 | F40 |
| Terbinafine hydrochloride | 10 | Control 1 | Control 2 |
| Disodium cocoamphodiacetate | 15 | | |
| Ethanol | 39.5 | | |
| Urea | 15 | | |
| Water | 8 | | |
| Menthol | 5 | | |
| D-Panthenol | 7.5 | | |

Table 16 FIII = F22

Figure 12:
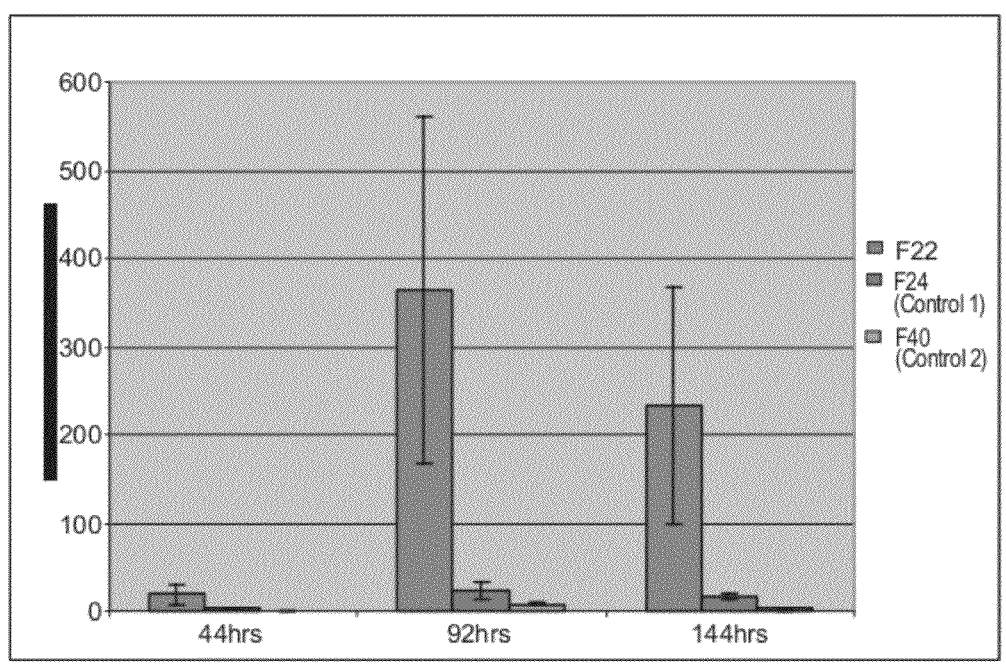
FIG. 12 illustrates the results of bovine hoof permeation studies on the formulations of Table 12.

The results are shown in FIG. 12. After multiple applications, the terbinafine formulation shows higher permeation than the controls. This experiment used multiple infinite dose applications at each time point and without stirring.

Example 13

Bovine Hoof Permeation of Terbinafine Formulations XIII

TABLE 13

Bovine Hoof Permeation of Terbinafine Formulations XIII

| | Formulations | | |
|---|---|---|---|
| Ingredients | F24 | F2 | F40 |
| Terbinafine hydrochloride | 10 | 10 | Control 2 |
| Ethanol | 32.5 | | |
| Ethyl acetate | 15 | | |
| Disodium cocoamphodiacetate | 10 | | |
| Water | 12.5 | | |
| Lactic acid | 5 | | |
| Menthol | 5 | | |
| Sodium isethionate | | 10 | |
| Ethanol | | 46 | |
| Urea | 10 | 10 | |
| Water | | 12 | |
| Ammonium thioglycolate (60% aqueous solution) | | 10 | |
| HPC HY 118 | | 2 | |

Table 16 FIX = F100

Figure 13A:
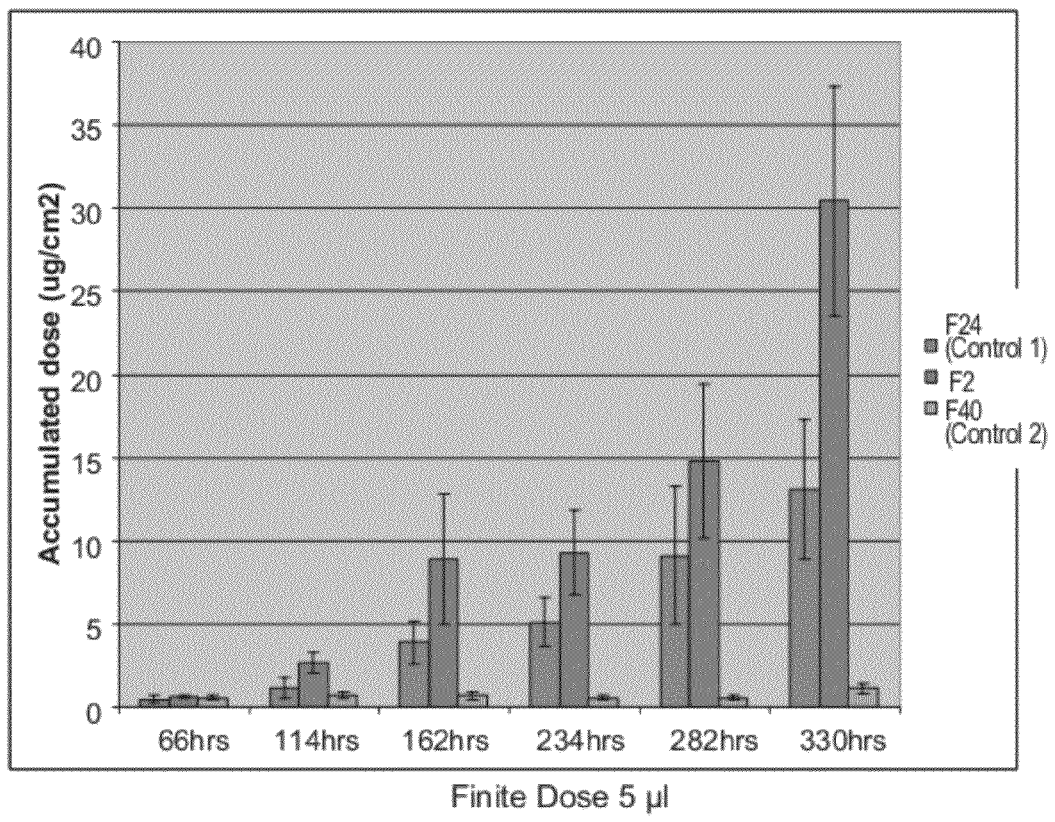
FIGS. 13A and 13B illustrate the results of bovine hoof studies on the formulations of Table 13.
Figure 13B:
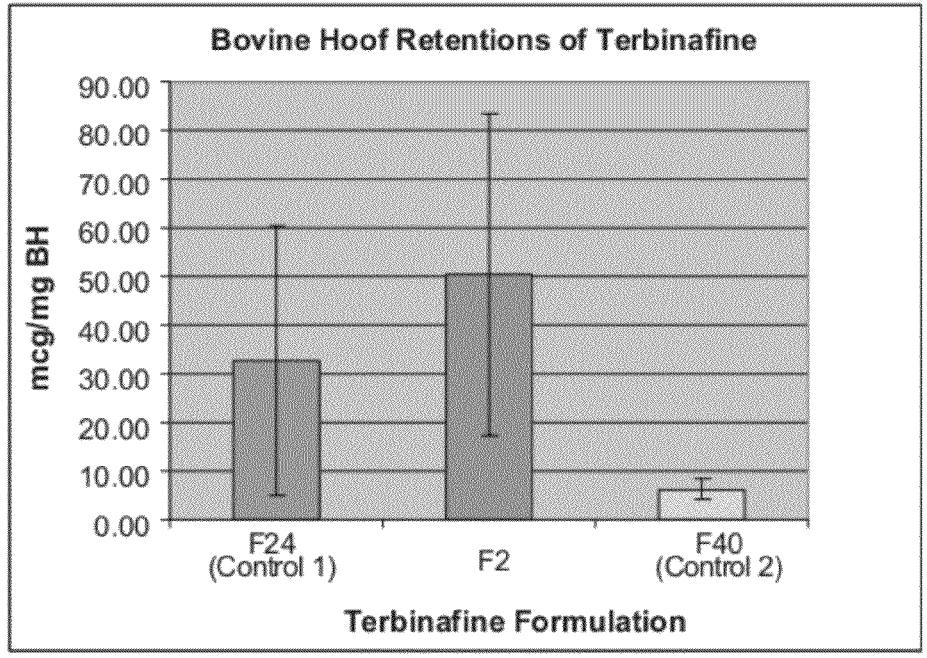

The results are shown in FIGS. 13A and 13B. Both DCAM and ammonium thioglycolate formulations show higher permeation enhancement than Control 2 (Lamisil®). This experiment used finite dose applications of 5 µl at every sampling time.

ATG formulation has somewhat higher permeation than DCAM formulations (approximately 2×) at longer exposure time During earlier exposure time period, the permeation differences are not significant.

Example 14

Bovine Hoof Permeation of Terbinafine Formulations XIV

TABLE 14

Bovine Hoof Permeation of Terbinafine Formulations XIV

| | Formulations | | |
|---|---|---|---|
| Ingredients | F40 | F111 | F112 |
| Terbinafine hydrochloride | Control 2 | 10 | 10 |
| Ethanol | | 35.5 | 35.5 |
| Ethyl acetate | | 20 | 20 |
| Disodium cocoamphodiacetate | | 10 | 10 |
| Water | | 17.5 | 17.5 |
| Lactic acid | | 5 | 5 |
| HPC HY 117 | | 2 | |
| Eudragit L100 | | | 2 |

Table 16 FX = F111
Table 16 FXI = F112

Figure 14A:
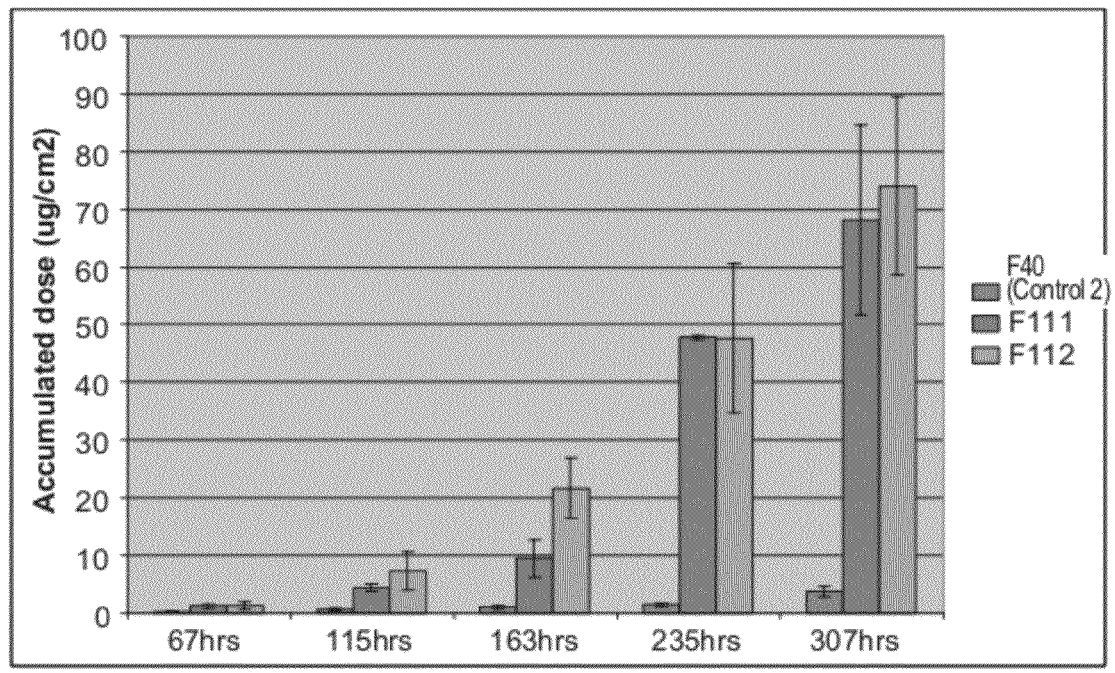
FIGS. 14A and 14B illustrate the results of bovine hoof permeation studies on the formulations of Table 14.
Figure 14B:
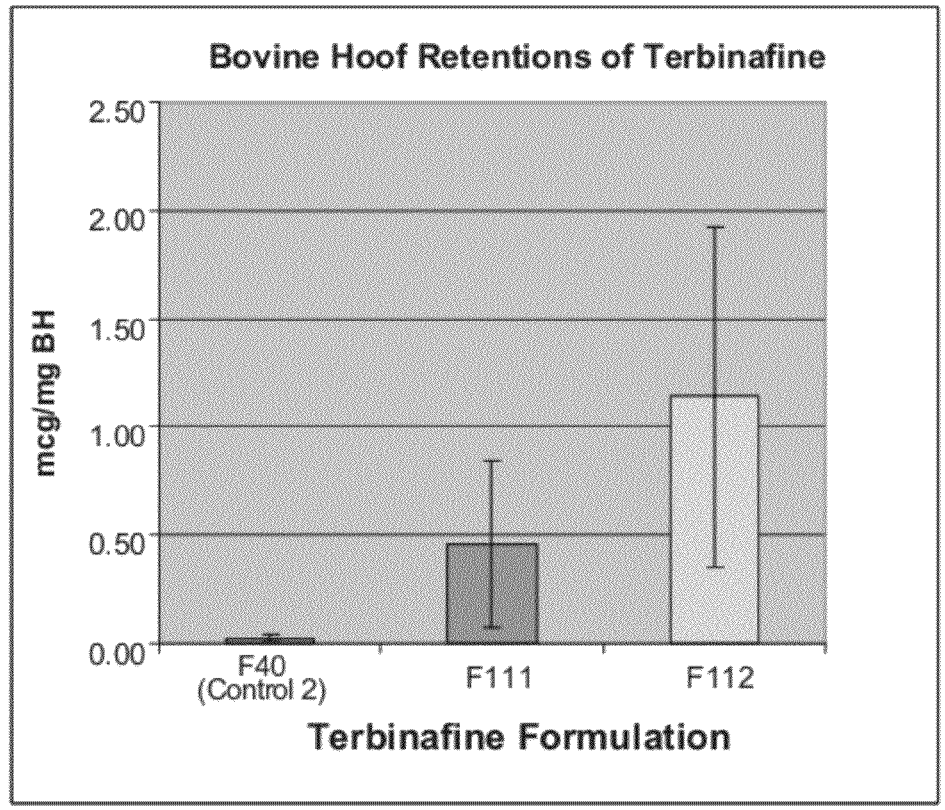

The results are shown in FIGS. 14A and 14B. A combination of DCAM based formulations with thickeners and ethyl acetate shows promising results. This experiment used finite dose application of 5 µl at every sampling time.

Example 15

Bovine Hoof Permeation of Terbinafine Formulations XV

TABLE 15

Bovine Hoof Permeation of Terbinafine Formulations XV

| Ingredients | Formulations | | |
|---|---|---|---|
| | F40 | F121 | F122 |
| Terbinafine hydrochloride | Control 2 | 10 | 10 |
| Ethanol | | 32.5 | 32.5 |
| Ethyl acetate | | 15 | 15 |
| Urea | | 10 | 10 |
| Disodium cocoamphodiacetate | | 10 | 10 |
| Menthol | | 3 | 3 |
| Lactic acid | | 5 | 5 |
| Eudragit L100 | | 2 | |
| HPC HY 117 | | | 2 |
| Water | | 12.5 | 12.5 |

Table 16 FXII = F121
Table 16 FXIII = F122

Figure 15A:
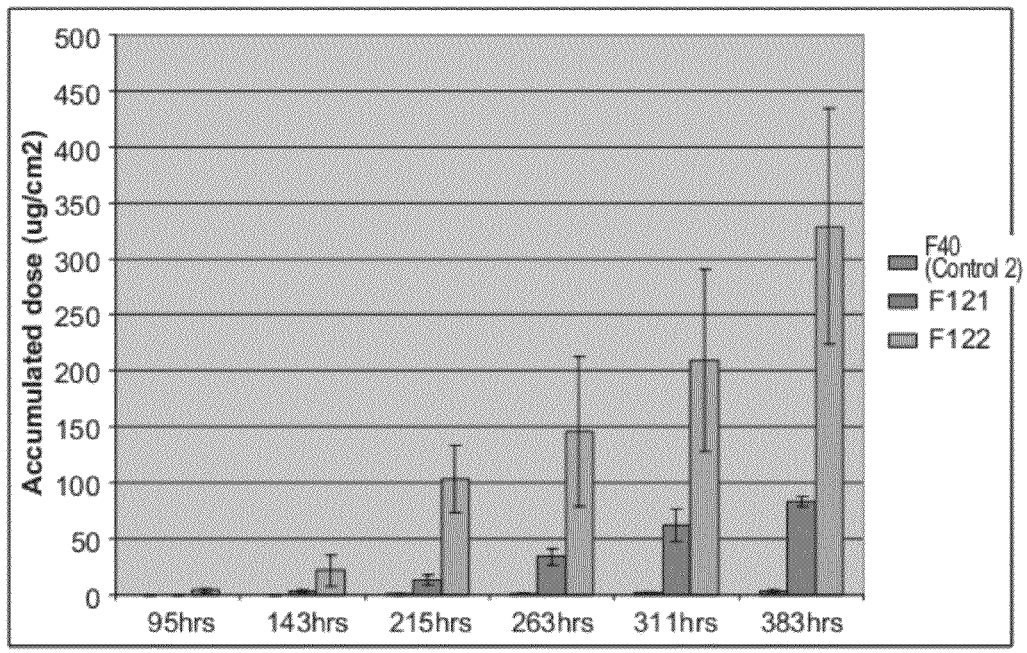
FIGS. 15A and 15B illustrate the results of bovine hoof studies on the formulations of Table 15.
Figure 15B:
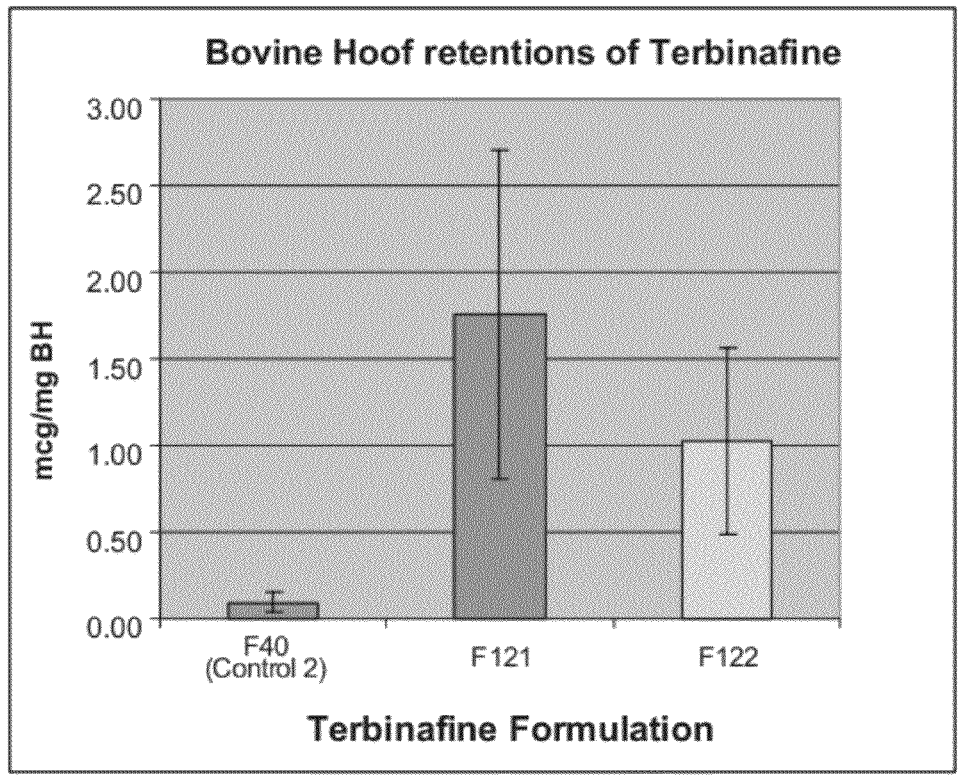

The results are shown in FIGS. 15A and 15B. A formulation with ethyl acetate showed higher delivery after addition of hydroxypropyl cellulose. Addition of Eudragit L 100 (2%) as a film-forming agent reduced the delivery compared to HPC.

Example 16

Terbinafine DCAM/Acid Chassis

TABLE 16

Terbinafine DCAM/Acid Chassis

| Ingredients | Formulations | | | | | | |
|---|---|---|---|---|---|---|---|
| | FI | FII | FIII | FIV | FV | FVI | FVII |
| Terbinafine hydrochloride | 16.7 | 10 | 10 | 10 | 10 | 10 | 10 |
| Ethanol | 41.7 | 45 | 39.5 | 50 | 30 | 25 | 22.5 |
| Water | 16.6 | 10 | 8 | 12.5 | 12.5 | 12.5 | 12.5 |
| Disodium cocoamphodiacetate | 16.7 | 15 | 15 | 20 | 20 | 20 | 20 |
| Urea | | 15 | 15 | | | 15 | 15 |
| Caprylic acid | 8.3 | | | | | | |
| Menthol | | 5 | 5 | | | 5 | 5 |
| D-Panthenol | | | 7.5 | | | | |
| Lactic acid | | | | 7.5 | 7.5 | 7.5 | 7.5 |
| Ethyl acetate | | | | | 20 | 5 | 7.5 |
| HPC HY117 | | | | | | | |
| Eudragit L100 | | | | | | | |

| Ingredients | Formulations | | | | | | |
|---|---|---|---|---|---|---|---|
| | FVIII | FIX | FX | FXI | FXII | FXIII | FXIV |
| Terbinafine hydrochloride | 10 | 10 | 10 | 10 | 10 | 10 | 10 |
| Ethanol | 30 | 32.5 | 35.5 | 35.5 | 32.5 | 32.5 | 35.5 |
| Water | 12.5 | 12.5 | 17.5 | 17.5 | 12.5 | 12.5 | 17.5 |
| Disodium cocoamphodiacetate | 10 | 10 | 10 | 10 | 10 | 10 | 10 |
| Urea | 10 | 10 | | | 10 | 10 | |
| Caprylic acid | | | | | | | |

TABLE 16-continued

Terbinafine DCAM/Acid Chassis

| Menthol | 5 | 5 | | | 3 | 3 | |
| --- | --- | --- | --- | --- | --- | --- | --- |
| D-Panthenol | | | | | | | |
| Lactic acid | 7.5 | 5 | 5 | 5 | 5 | 5 | 5 |
| Ethyl acetate | 15 | 15 | 20 | 20 | 15 | 15 | 20 |
| HPC HY117 | | | 2 | | | 2 | |
| Eudragit L100 | | | | 2 | 2 | | 2 |

All the formulations of Example 16 contain zwitterionic detergent, alpha-hydroxy acids (or short-chain acids), or both. In addition, these formulations may contain urea, menthol, or both as penetration agents. The formulations also contain alcohol mixtures, and some contain short-chain alkyl esters (ethyl acetate) as solvent.

D-Panthenol is optional. These formulations also may contain a thickener and/or film forming polymer.

Example 17

Solubility of Terbinafine Hydrochloride

Procedure

Buffer Preparation: Buffers were prepared at 50 mM concentration using ammonium acetate (pHs 4.0 and 10.0) or ammonium phosphate (pHs 6.0, 7.0, and 8.0).

Solubility Sample Preparation: 100 to 800 mg terbinafine HCL was transferred to separate 4-mL vials. To each vial, 2 mL of the solvent to be investigated was added. Samples were capped and then rotated for 24 hours at room temperature. The samples were allowed to settle overnight at room temperature. Approximately 0.4 mL of the supernatant was removed and transferred to a 0.45 µm Nylon microcentrifuge filter and clarified. Samples were diluted with 50% methanol to within the calibration range.

Sample Analysis: Samples were analyzed by HPLC with five-minute runs. Calibration standards at approximately 0.00, 0.02, 0.1, 0.25, 0.65, and 1.0 mg/mL were used to construct a calibration curve, from which sample concentrations were determined and corrected for dilution to achieve the final solubility result.

Results

The solubility of terbinafine hydrochloride in the solvents investigated is presented in Table 17.

TABLE 17

Summary of Terbinafine Solubility Results

| Solvent | Solubility (mg/mL) |
|---|---|
| Water | 5.9 |
| pH 4.0 | 4.8 |
| pH 6.0 | 5.0 |
| pH 7.0 | 0.02 |
| pH 8.0 | 0.002 |
| pH 10.0 | 1.5 |
| PBS pH 5.5 | 0.7 |
| 5% Ethanol | 6.7 |
| 10% Ethanol | 7.5 |
| 20% Ethanol | 11 |
| 40% Ethanol | 53 |
| 50% Ethanol | 119 |
| Ethanol | 172 |
| DMSO | 114 |
| Isopropanol | 26.3 |
| Ethyl acetate | 0.7 |
| Isopropyl myristate | 0.03 |
| F131 | 280 |
| F141 | 239 |

The solubility of terbinafine hydrochloride in various aqueous and organic solvents has been investigated. Terbinafine hydrochloride shows moderate solubility in aqueous solvents with pHs of 4 and 6 but shows substantially lower solubility at pHs 7, 8, and 10. Terbinafine hydrochloride shows high solubility in polar organic solvents such as ethanol and DMSO, but lower solubility in non-polar solvents such as ethyl acetate and isopropyl myristate. The solubility in inventive topical formulations (i.e., F131, F141) is high and ranges from 239 to 280 mg/mL (ca. 24 to 28% w/v).

Example 18

Cadaver Nail Permeation of Terbinafine Formulations XVI

TABLE 18

Terbinafine F131 and F131 Variant Formulations

| Ingredients | Formulations | | |
|---|---|---|---|
| | F131 % w/w | F132 % w/w | F133 % w/w |
| Terbinafine | 10 | 10 | 15 |
| Ethyl alcohol 200 proof USP | 32.5 | 32.5 | 27.5 |
| Disodium cocoamphodiacetate | 10 | 10 | 10 |
| Urea | 10 | 10 | 10 |
| L-Lactic acid | 5 | 5 | 5 |
| Ethyl acetate | 15 | 15 | 15 |
| Hydroxypropyl cellulose HY 117 NF | 2 | 2 | 2 |
| Purified Water (USP) | 12.5 | 12.5 | 12.5 |
| Hexanetriol | | 3 | 3 |
| Menthol | 3 | | |

TABLE 19

Terbinafine F131 Formulation Results I
Accumulated Dose (µg/cm$^2$)

| Formula | F40 (Control 2) | F131 |
|---|---|---|
| 96 h | 0.19 ± 0.1 | 0.77 ± 0.6 |
| 120 h | 0.14 ± 0.1 | 1.30 ± 0.9 |
| 168 h | 0.10 ± 0.01 | 2.25 ± 1.5 |
| 264 h | 0.44 ± 0.03 | 8.50 ± 4.7 |
| 312 h | 0.46 ± 0.1 | 9.07 ± 5.2 |
| 360 h | 0.72 ± 0.04 | 14.69 ± 7.4 |

Figure 16A:
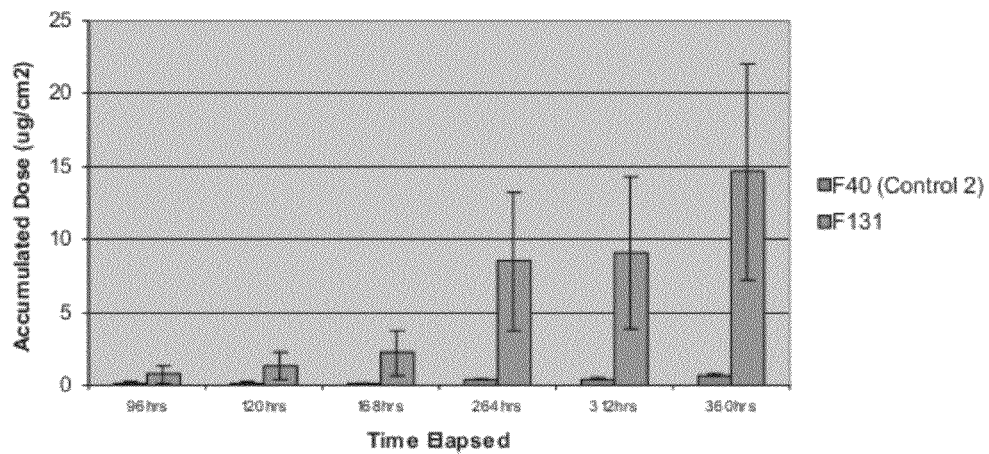
FIGS. 16A-B illustrate the results of permeation studies on F131 (Tables 18, 19, and 20).

These results are shown in FIG. 16A.

TABLE 20

Terbinafine F131 Formulation Results II
Accumulated Dose (µg/cm$^2$)

| Formula | F40 (Control 2) | F131 |
|---|---|---|
| 48 h | 0.60 ± 0.16 | 0.067 ± 0.03 |
| 96 h | 1.06 ± 0.50 | 0.10 ± 0.35 |
| 168 h | 1.83 ± 0.84 | 8.55 ± 3.45 |
| 216 h | 2.40 ± 1.13 | 12.60 ± 4.0 |
| 264 h | 2.28 ± 1.08 | 21.09 ± 5.95 |
| 336 h | 2.60 ± 1.11 | 39.66 ± 10.26 |

Figure 16B:
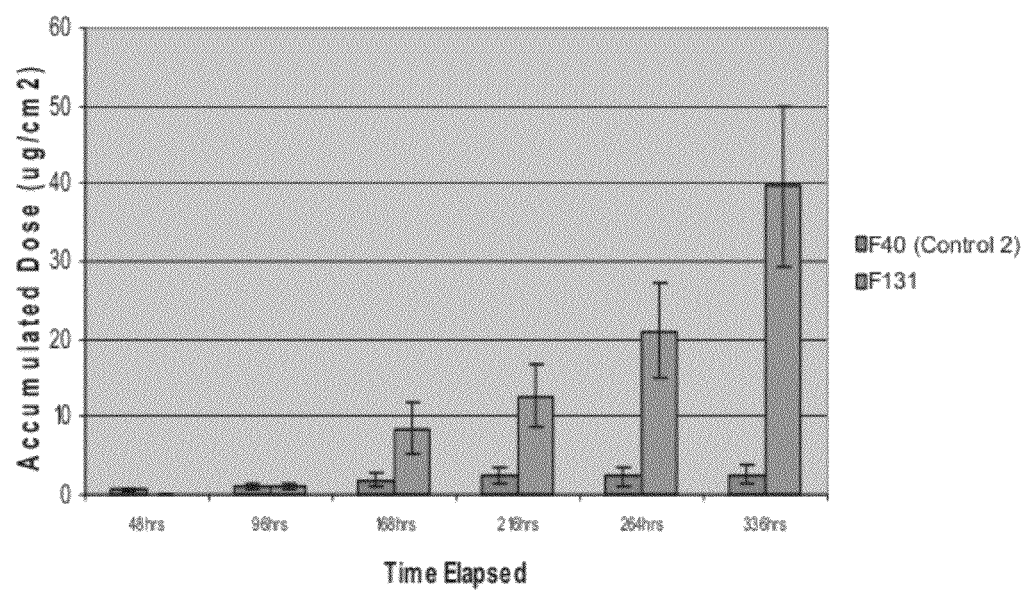

These results are shown in FIG. 16B.

TABLE 21

Comparison of F131 Variant Formulations
Accumulated Dose (µg/cm$^2$)

| Formula | F40 (Control 2) | F132 | F133 |
|---|---|---|---|
| 48 h | 0.33 ± 0.21 | 1.43 ± 0.84 | 2.54 ± 1.22 |
| 96 h | 0.63 ± 0.27 | 5.10 ± 2.58 | 5.80 ± 1.25 |
| 168 h | 2.50 ± 1.05 | 9.61 ± 4.43 | 12.71 ± 0.81 |
| 216 h | 2.8 ± 0.26 | 24.15 ± 11.05 | 50.91 ± 13.40 |
| 264 h | 3.93 ± 0.29 | 34.48 ± 16.10 | 53.64 ± 5.72 |
| 336 h | 4.83 ± 0.45 | 50.59 ± 27.60 | 74.94 ± 8.93 |

Figure 17A:
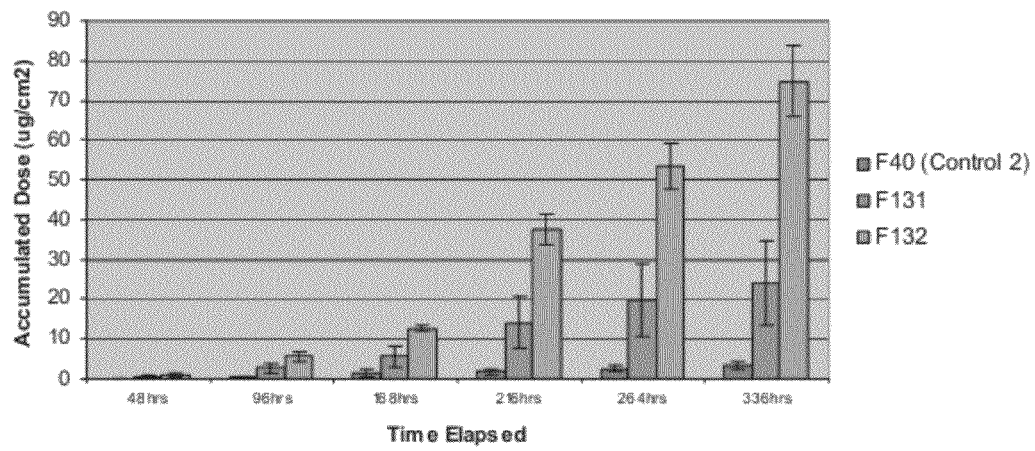
FIGS. 17A-B illustrate the results of permeation studies on F132, F133, and F141.

As shown in FIG. 17A, permeation increases with the concentration of terbinafine (10% vs 15%), but does not increase linearly.

TABLE 22

Terbinafine F141 and F141 Variant Formulation

| Ingredients | Formulations | |
|---|---|---|
| | F141 % w/w | F143 % w/w |
| Terbinafine | 10 | 20 |
| Ethyl alcohol 200 proof USP | 35.5 | 30.5 |
| Disodium cocoamphodiacetate | 10 | 10 |
| L-Lactic acid | 5 | 5 |
| Ethyl acetate | 20 | 15 |
| Hydroxypropyl cellulose HY 117 NF | 2 | 2 |
| Purified Water (USP) | 17.5 | 17.5 |

TABLE 23

Terbinafine F141 Formulation Results
Accumulated Dose (µg/cm$^2$)

| Formula | F40 (Control 2) | F141 |
|---|---|---|
| 48 h | 0.16 ± 0.11 | 0.15 ± 0.07 |
| 96 h | 0.62 ± 0.16 | 1.41 ± 0.74 |
| 168 h | 3.33 ± 1.40 | 3.86 ± 1.73 |
| 216 h | 2.58 ± 0.31 | 10.54 ± 3.16 |
| 264 h | 4.03 ± 0.39 | 17.83 ± 4.67 |
| 336 h | 7.17 ± 0.67 | 36.92 ± 6.71 |

Figure 17B:
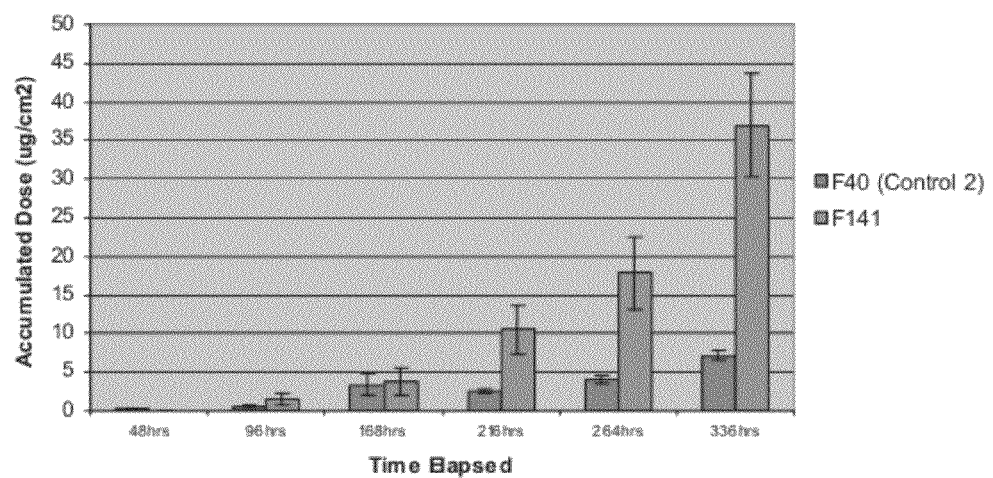

These results are shown in FIG. 17B.

TABLE 24

Terbinafine F141 Formulation Results (BID)
Accumulated Dose (µg/cm$^2$)

| Formula | F40 (Control 2) | F141 | F141 BID |
|---|---|---|---|
| 48 hrs | 0.13 ± 0.01 | 0.33 ± 0.08 | 0.27 ± 0.07 |
| 96 hrs | 0.29 ± 0.07 | 0.71 ± 0.23 | 3.68 ± 2.10 |
| 168 hrs | 0.35 ± 0.13 | 1.23 ± 0.68 | 12.58 ± 6.76 |
| 216 hrs | 0.63 ± 0.20 | 5.35 ± 2.78 | 24.09 ± 12.44 |
| 264 hrs | 2.06 ± 0.54 | 15.02 ± 7.49 | 55.22 ± 25.51 |
| 336 hrs | 1.76 ± 0.44 | 20.24 ± 9.02 | 75.50 ± 33.69 |

Figure 18A:
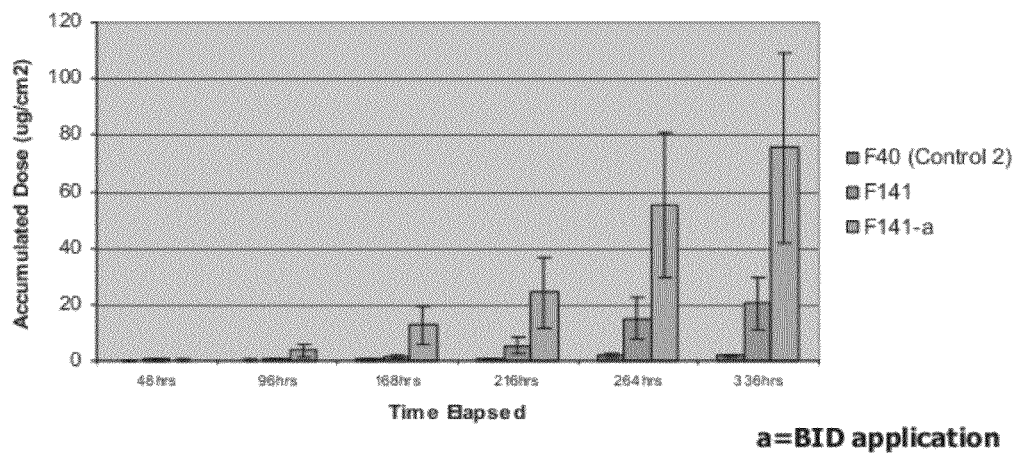
FIGS. 18A-B illustrate the results of permeation studies on F131 and F141.

As shown in FIG. 18A, dosing studies suggest Terbinafine permeation nearly doubles with twice daily (BID) dosing.

TABLE 25

Comparison of F131 and F141
Accumulated Dose (μg/cm²)

| Formula | F40 (Control 2) | F131 | F141 |
|---|---|---|---|
| 48 h | 0.04 ± 0.02 | 0.66 ± 0.19 | 0.10 ± 0.04 |
| 96 h | 0.34 ± 0.20 | 5.35 ± 1.69 | 1.08 ± 0.73 |
| 168 h | 0.44 ± 0.21 | 11.24 ± 4.88 | 5.85 ± 3.60 |
| 216 h | 0.70 ± 0.30 | 18.26 ± 6.38 | 10.00 ± 5.02 |
| 264 h | 0.99 ± 0.37 | 25.43 ± 7.30 | 18.18 ± 9.49 |
| 336 h | 1.46 ± 0.45 | 41.40 ± 9.06 | 28.17 ± 7.91 |

Figure 18B:
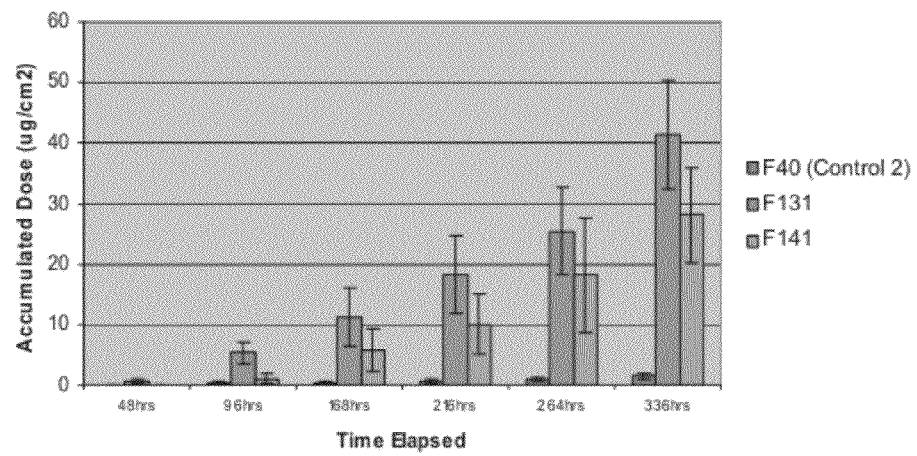

These results are shown in FIG. 18B.

TABLE 26

Cadaver Nail Permeation of F143
Accumulated Dose (μg/cm²)

| Formula | F40 (Control 2) | F143 |
|---|---|---|
| 48 h | 0.97 ± 0.57 | 3.63 ± 0.64 |
| 96 h | 2.04 ± 1.08 | 4.32 ± 0.69 |
| 168 h | 2.36 ± 0.96 | 7.84 ± 1.14 |
| 216 h | 2.44 ± 0.74 | 11.53 ± 1.74 |
| 264 h | 2.93 ± 0.79 | 16.87 ± 2.63 |
| 336 h | 4.06 ± 0.61 | 30.93 ± 4.64 |

Figure 19A:
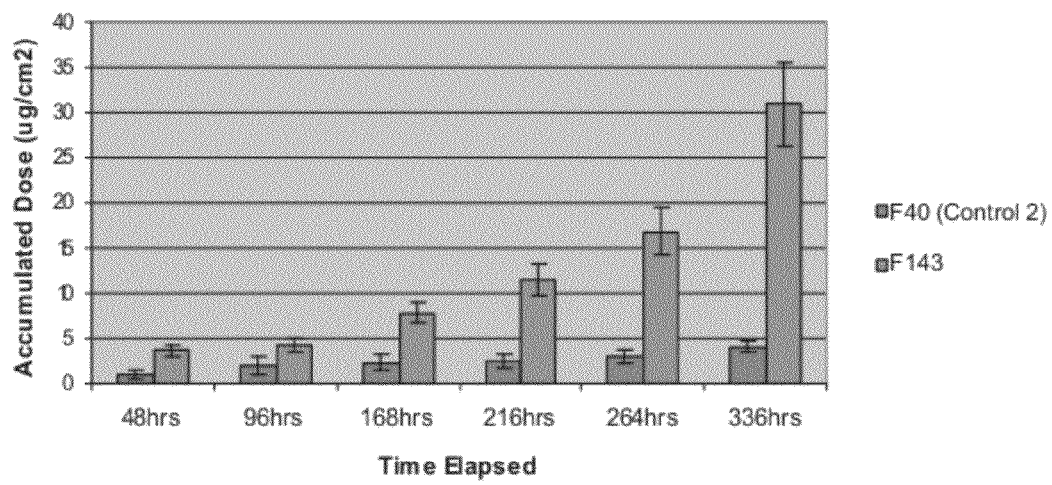
FIGS. 19A-B illustrate the results of permeation studies on F141 and F143.

These results are shown in FIG. 19A.

TABLE 27

Relative Enhancement of F141 and F141 Variant Formulations
Re. F40 (Control 2; Lamisil ®)

| Formula | F141 | F143 |
|---|---|---|
| 48 h | 0.53 | 3.76 |
| 96 h | 2.27 | 2.11 |
| 168 h | 1.16 | 3.32 |
| 216 h | 4.09 | 4.73 |
| 264 h | 4.43 | 5.76 |
| 336 h | 5.15 | 7.61 |

Figure 19B:
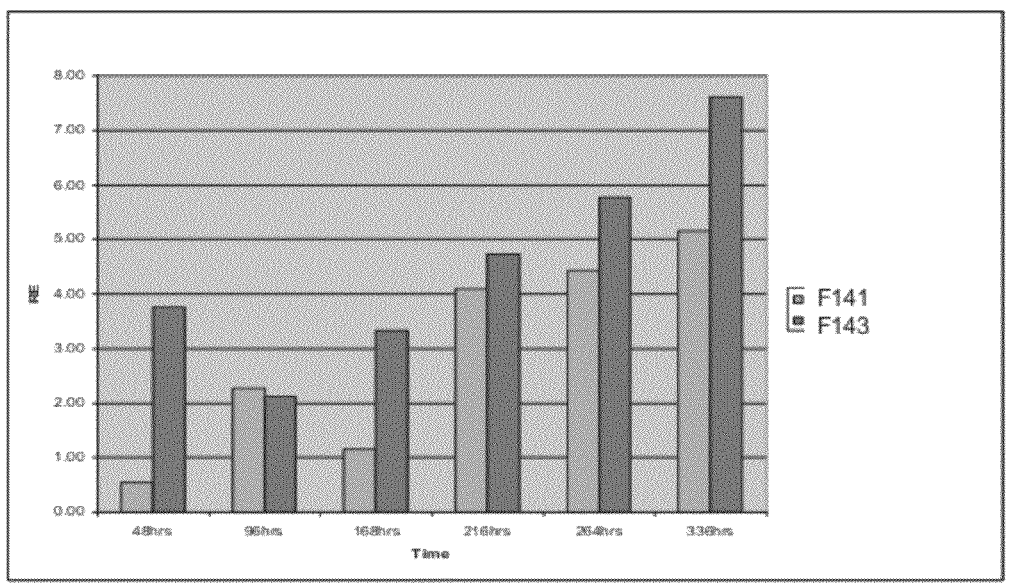

These results are shown in FIG. 19B.

Example 19

Terbinafine Formulation pH Stability Studies

In this experiment, the pH stability of F131, F141, and F142 was tested.

TABLE 28

Compositions of F131 and F141

| Ingredients | F131 % w/w | F141 % w/w | F142 % w/w |
|---|---|---|---|
| Terbinafine | 10 | 10 | 15 |
| Ethyl alcohol 200 proof USP | 32.5 | 35.5 | 30.5 |
| Disodium cocoamphodiacetate | 10 | 10 | 10 |
| Urea | 10 | | |
| Choline chloride | | | |
| L-Lactic acid | 5 | 5 | 5 |
| Ethyl acetate | 15 | 20 | 20 |
| Hydroxypropyl cellulose HY 117 NF | 2 | 2 | 2 |
| Purified Water (USP) | 12.5 | 17.5 | 17.5 |
| Menthol | 3 | | |

TABLE 29 pH of Test Formulations F131 and F141 (25° C.)

| | 25° C. | |
|---|---|---|
| Time | F131 | F141 |
| 0 h | 4.18 | 4.14 |
| 1 mon | 4.1 | 3.85 |
| 2 mon | 4.15 | 4.11 |
| 3 mon | 4.15 | 3.85 |

Figure 20:
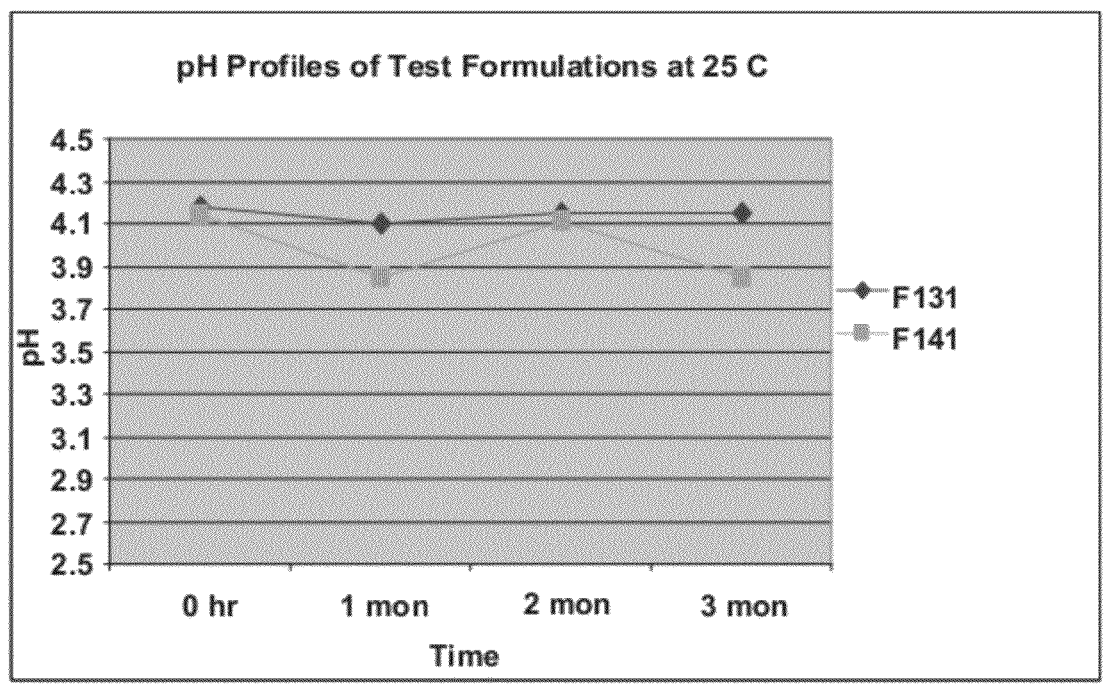
FIG. 20 illustrates a three-month pH stability profile for F131 and F141 at 25° C. (Table 29).

These results are shown in FIG. 20.

TABLE 30 pH of Test Formulation F142 (25° C.)

| Time | F142 |
|---|---|
| 0 h | 3.79 |
| 1 mon | 4.0 |
| 2 mon | 4.12 |
| 3 mon | 4.10 |

Figure 21:
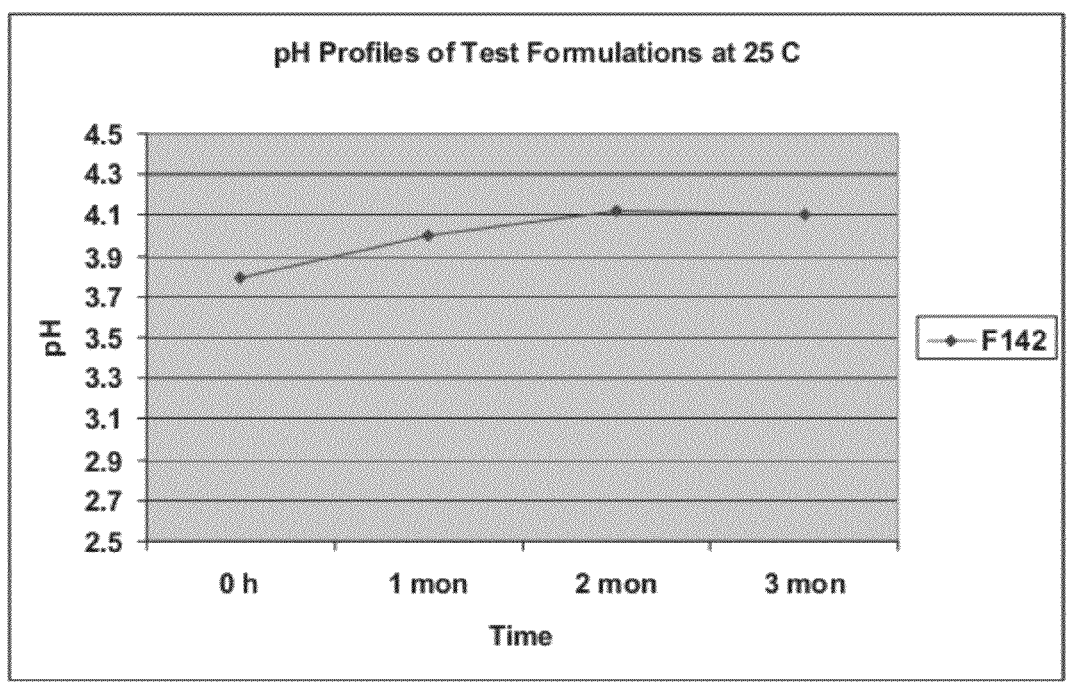
FIG. 21 illustrates a three-month pH stability profile for F142 at 25° C. (Table 30).

These results are shown in FIG. 21.

Example 20

Terbinafine Permeation Studies XVII

TABLE 31

F131 and F131 Variant Formulations

| | Formulations | | |
|---|---|---|---|
| Ingredients | F131 % w/w | F132 % w/w | F133 % w/w |
| Terbinafine | 10 | 10 | 15 |
| Ethyl alcohol 200 proof USP | 32.5 | 32.5 | 27.5 |
| Disodium cocoamphodiacetate | 10 | 10 | 10 |
| Urea | 10 | 10 | 10 |
| L-Lactic acid | 5 | 5 | 5 |
| Ethyl acetate | 15 | 15 | 15 |
| Hydroxypropyl cellulose HY 117 NF | 2 | 2 | 2 |
| Purified Water (USP) | 12.5 | 12.5 | 12.5 |
| Hexanetriol | | 3 | 3 |
| Menthol | 3 | | |

A 20% terbinafine variant of this formulation was not prepared due to physical stability issues.

TABLE 32

F141 and F141 Variant Formulations

| | Formulations | | |
|---|---|---|---|
| Ingredients | F141 % w/w | F142 % w/w | F143 % w/w |
| Terbinafine | 10 | 15 | 20 |
| Ethyl alcohol 200 proof USP | 35.5 | 30.5 | 30.5 |
| Disodium cocoamphodiacetate | 10 | 10 | 10 |
| L-Lactic acid | 5 | 5 | 5 |
| Ethyl acetate | 20 | 20 | 15 |
| Hydroxypropyl cellulose HY 117 NF | 2 | 2 | 2 |
| Purified Water (USP) | 17.5 | 17.5 | 17.5 |

TABLE 33

Cadaver Nail Penetration of F141 and F141 Variant Formulations
Accumulated Dose (µg/cm$^2$)

| Formula | F40 (Control 2) | F141 | F142 | F143 | F142-a | F142-b |
|---|---|---|---|---|---|---|
| 24 hrs | 0.11 ± 0.03 | 0.15 ± 0.07 | 0.01 ± 0.01 | 0.04 ± 0.03 | 0.13 ± 0.03 | 0.02 ± 0.01 |
| 96 hrs | 0.40 ± 0.10 | 3.80 ± 1.79 | 1.29 ± 0.35 | 3.95 ± 1.23 | 1.77 ± 0.29 | 0.22 ± 0.14 |
| 144 hrs | 0.73 ± 0.23 | 9.51 ± 4.37 | 3.65 ± 0.71 | 11.02 ± 1.64 | 17.38 ± 10.10 | 0.44 ± 0.29 |
| 192 hrs | 1.23 ± 0.42 | 15.48 ± 6.58 | 8.52 ± 0.97 | 22.67 ± 0.82 | 15.88 ± 6.70 | 1.31 ± 1.09 |
| 264 hrs | 2.85 ± 1.02 | 34.91 ± 12.79 | 24.47 ± 4.04 | 52.15 ± 8.77 | 54.16 ± 17.13 | 0.81 ± 0.42 |
| 312 hrs | 3.69 ± 1.43 | 51.81 ± 16.96 | 37.55 ± 6.36 | 78.62 ± 16.64 | 77.87 ± 19.33 | 1.29 ± 0.59 |
| 360 hrs | 4.98 ± 1.81 | 82.07 ± 25.66 | 60.24 ± 10.62 | 116.34 ± 24.44 | 116.07 ± 24.19 | 2.08 ± 0.96 |
| 432 hrs | 6.51 ± 2.45 | 115.26 ± 31.04 | 90.80 ± 18.47 | 177.41 ± 51.54 | 178.57 ± 39.75 | 4.30 ± 2.83 | a = BID application;
b = once weekly application

Figure 22A:
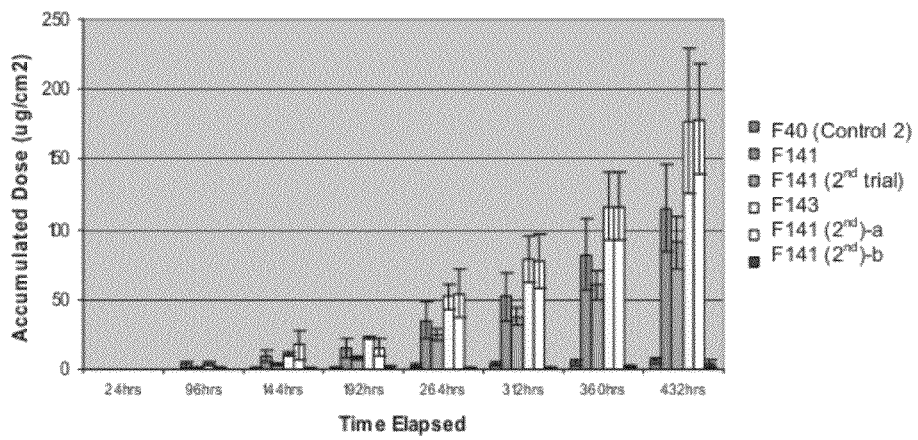
FIGS. 22A-B illustrate the results of permeation studies on F141, F142, and F143.

The results of this experiment are shown on FIG. 22A.

TABLE 34

Shed Snakeskin Penetration of F141 and F141 Variant Formulations
Accumulated Dose (µg/cm$^2$)

| Formula | F40 (Control 2) | F141 | F142 | F143 | F143-a |
|---|---|---|---|---|---|
| 4 hrs | 0.48 ± 0.03 | 0.48 ± 0.20 | 0.02 ± 0.01 | 0.13 ± 0.06 | 0.47 ± 0.41 |
| 21 hrs | 2.87 ± 0.12 | 209.23 ± 46.31 | 141.04 ± 53.96 | 139.27 ± 40.48 | 130.71 ± 53.44 |
| 24 hrs | 2.91 ± 0.16 | 342.01 ± 40.21 | 253.26 ± 52.36 | 253.64 ± 36.50 | 243.56 ± 38.08 | a = BID application

Figure 22B:
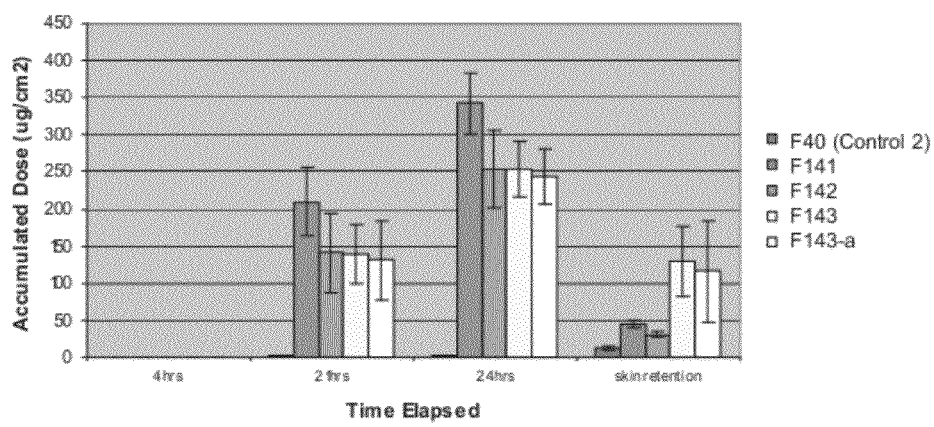

The results of this experiment are shown on FIG. 22B.

TABLE 35

Shed Snakeskin Penetration of F131 and F131 Variant Formulations
Accumulated Dose (µg/cm$^2$)

| Formula | F40 (Control 2) | F131 | F131-a | F132 | F133 | F131-b |
|---|---|---|---|---|---|---|
| 4 hrs | 0.86 ± 0.07 | 3.91 ± 1.47 | 1.47 ± 0.50 | 0.96 ± 0.27 | 1.30 ± 0.77 | 0.71 ± 0.30 |
| 21 hrs | 4.37 ± 0.32 | 614.76 ± 143.47 | 721.60 ± 91.70 | 364.73 ± 84.97 | 380.82 ± 85.60 | 457.98 ± 96.46 |
| 24 hrs | 4.03 ± 0.26 | 682.88 ± 126.63 | 829.34 ± 113.35 | 386.56 ± 103.09 | 413.62 ± 102.14 | 495.82 ± 113.43 | a = F131 stability samples 25° C. 3 months;
b = freshly prepared F131 formulation.

Figure 23A:
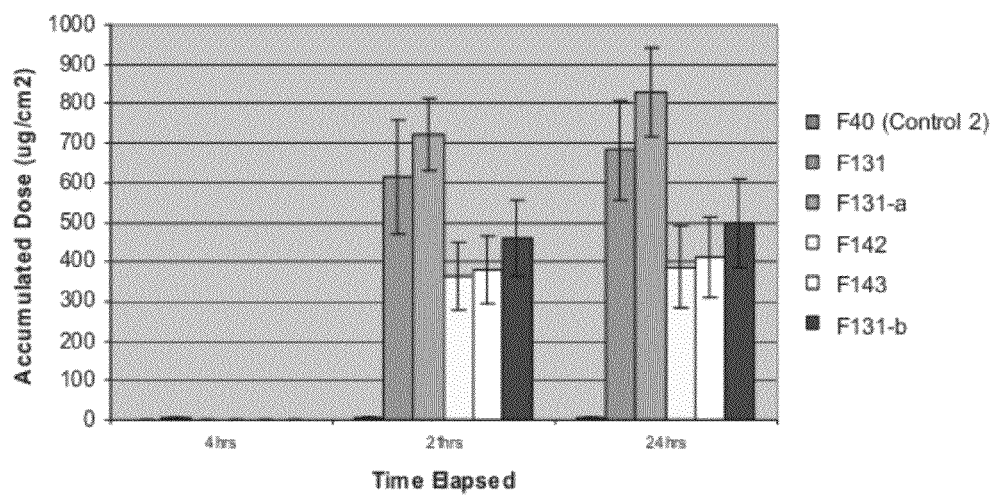
FIGS. 23A-B illustrate the results of permeation studies on F131-F133 and F141-F143.

The results of this experiment are shown on FIG. 23A.

TABLE 36

Cadaver Nail Penetration of F141 and F141 Variant Formulations
Accumulated Dose (µg/cm$^2$)

| Formula | F40 (Control 2) | F141 | F142 | F143 |
|---|---|---|---|---|
| 48 hrs | 0.0 ± 0.00 | 0.00 ± 0.00 | 0.12 ± 0.12 | 0.05 ± 0.05 |
| 120 hrs | 0.20 ± 0.04 | 1.07 ± 0.65 | 2.88 ± 1.78 | 1.33 ± 0.88 |
| 168 hrs | 0.37 ± 0.14 | 2.53 ± 1.45 | 6.40 ± 3.12 | 3.84 ± 2.11 |
| 216 hrs | 0.88 ± 0.22 | 4.97 ± 2.22 | 12.49 ± 5.70 | 16.20 ± 8.84 |
| 288 hrs | 1.47 ± 0.41 | 11.71 ± 3.75 | 25.20 ± 11.07 | 16.66 ± 7.80 |
| 336 hrs | 2.14 ± 0.55 | 18.91 ± 5.82 | 37.94 ± 16.17 | 26.16 ± 11.68 |

Figure 23B:
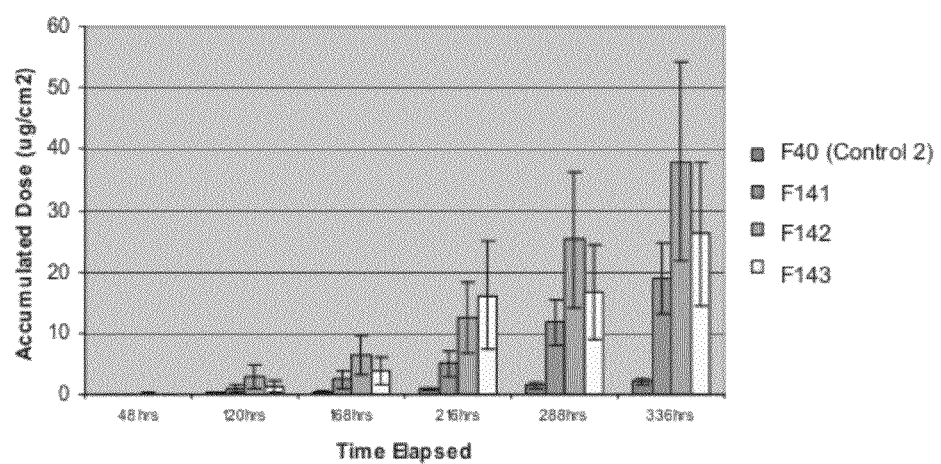

The results of this experiment are shown on FIG. 23B.

Example 21

Terbinafine Permeation Studies XVIII

The target of the current studies is to evaluate the flux behavior of F131 and F141 formulations after 6 months of storage at uncontrolled room temperature, in a 25° C. stability chamber, and in a 40° C. stability chamber. The formulations were kept in capped ~60 mL amber colored bottles with Teflon liners. Shed snake skin was used as model membrane, and F40 (Control 2) was the control.

TABLE 37

F131 Stability
Accumulated Dose (µg/cm$^2$)

| Formula | F40 (Control 2) | F131-RT-6 mon | F131-25-6 mon | F131-40-6 mon |
|---|---|---|---|---|
| 4 hrs | 1.13 ± 0.30 | 2.49 ± 1.44 | 7.91 ± 6.31 | 0.46 ± 0.22 |
| 21 hrs | 3.88 ± 0.39 | 299.83 ± 57.55 | 379.47 ± 49.18 | 432.02 ± 62.12 |
| 24 hrs | 2.63 ± 0.31 | 339.56 ± 69.67 | 418.78 ± 59.87 | 456.67 ± 70.60 |

Figure 24A:
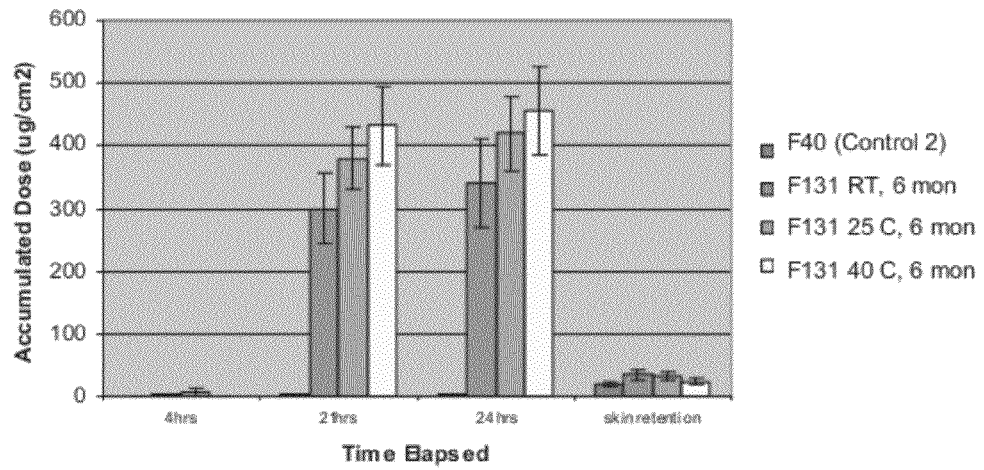
FIGS. 24A-B illustrate the results of permeation studies on F131 and F141 after stability tests.

The results for F131 are shown in FIG. 24A along with the permeation behavior of the F131 stability samples. No significant permeation difference was observed between F131 at every time point. The control exhibited a much lower permeation profile. Skin retentions of all formulations were similar (including placebos).

TABLE 38

| | F141 Stability Accumulated Dose (µg/cm²) | | | |
|---|---|---|---|---|
| Formula | F40 (Control 2) | F141-RT-6 mon | F141-25-6 mon | F141-40-6 mon |
| 4 hrs | 1.01 ± 0.13 | 2.27 ± 1.86 | 0.18 ± 0.05 | 0.72 ± 0.55 |
| 21 hrs | 3.43 ± 0.44 | 452.38 ± 115.75 | 350.53 ± 64.41 | 721.24 ± 25.16 |
| 24 hrs | 3.96 ± 0.37 | 629.23 ± 120.87 | 544.89 ± 68.12 | 875.50 ± 37.99 |

Figure 24B:
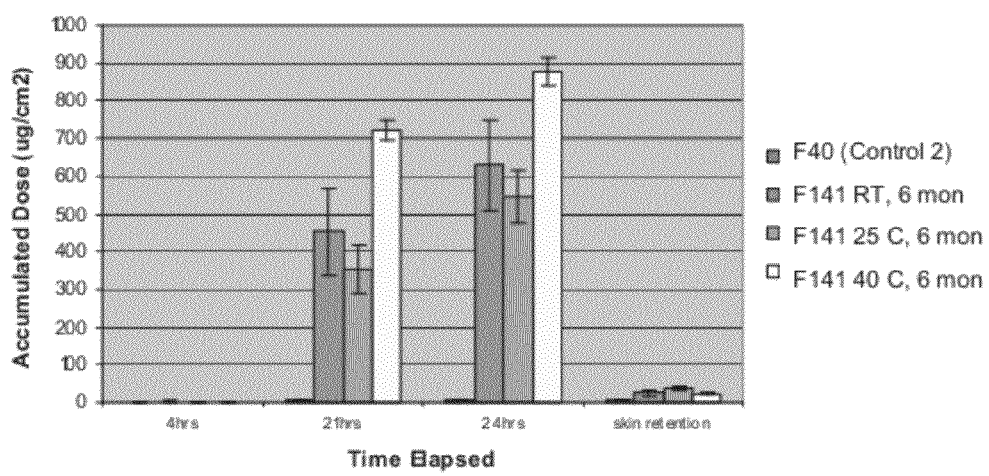

The results for F141 are shown in FIG. 24B. The permeation profiles of samples kept for 6 months at uncontrolled room temperature and 25° C. at stability chamber conditions were similar. At 40° C., the permeation appears to be more pronounced; however, it is highly possible there may be some evaporation of some volatile ingredients and therefore increased drug concentration in the formulation. The control exhibited a much lower permeation profile. Skin retentions of all formulations were similar (including placebos).

Example 22

Analysis of Terbinafine Stability Data from F131 and F141

This example describes the short-term physical and chemical stability of terbinafine formulations for a period of up to three months under long-term (i.e., 25±2° C., 40%±5% relative humidity (RH)) conditions.

General Methods:

Terbinafine formulations as provided in Tables 31 and 32 were placed in stability chambers at appropriate temperatures in a horizontal orientation.

Test Methods:

High-performance liquid chromatography (HPLC) was used for the assay of terbinafine in raw materials and in formulations.

Results:

The results of the stability studies for certain preferred embodiments are presented in Tables 39 to 42.

TABLE 39

| Six-Month Stability of F131: 25° C., Ambient Humidity | | | | | | | |
|---|---|---|---|---|---|---|---|
| Attribute | Method | Limits | Initial | 1 month | 2 months | 3 months | 6 months |
| Description | Visual | Clear, colorless to light yellow liquid or gel with a faint odor, essentially free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. |
| Terbinafine Assay | HPLC | 9.0 to 11.0% w/w | 10.0, 10.1 | 10.0 | 10.0 | 10.2 | 10.5 |

TABLE 40

| Six-Month Stability of F131: 40° C., Ambient Humidity | | | | | | | |
|---|---|---|---|---|---|---|---|
| Attribute | Method | Limits | Initial | 1 month | 2 months | 3 months | 6 months |
| Description | Visual | Clear, colorless to light yellow liquid or gel with a faint odor, essentially free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, light yellow liquid with faint odor. Free of visible foreign matter and crystallized particles. | Clear, light yellow liquid with faint odor. Free of visible foreign matter and crystallized particles. | Clear, light yellow liquid with faint odor. Free of visible foreign matter and crystallized particles. |
| Terbinafine Assay | HPLC | 9.0 to 11.0% w/w | 10.1, 10.1 | 10.0 | 10.0 | 10.1 | 10.6 |

TABLE 41

Six-Month Stability of F141: 25° C., Ambient Humidity

| Attribute | Method | Limits | Initial | 1 month | 2 months | 3 months | 6 months |
|---|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. |
| Terbinafine Assay | HPLC | 9.0 to 11.0% w/w | 9.9, 9.8 | 9.9 | 10.0 | 10.0 | 9.9 |

TABLE 42

Six-Month Stability of F141: 40° C., Ambient Humidity

| Attribute | Method | Limits | Initial | 1 month | 2 months | 3 months | 6 months |
|---|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, light yellow liquid with faint odor. Free of visible foreign matter and crystallized particles. | Clear, light yellow liquid with faint odor. Free of visible foreign matter and crystallized particles. | Clear, light yellow liquid with faint odor. Free of visible foreign matter and crystallized particles. |
| Terbinafine Assay | HPLC | 9.0 to 11.0% w/w | 9.9, 9.8 | 10.0 | 9.9 | 10.0 | 9.6 |

Example 23

Analysis of Terbinafine Stability Data from F132, F133, F142 and F143

The stability tests were conducted according to the method of Example 22.

| Attribute | Method | Limits | Initial | 1 month | 2 months | 3 months | 6 months |
|---|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible foreign matter and crystallized particles. | Clear, very light yellow liquid with faint odor. Free of visible foreign matter and crystallized particles. | Clear, light yellow liquid with faint odor. Free of visible foreign matter and crystallized particles. | Clear, light yellow liquid with faint odor. Free of visible foreign matter and crystallized particles. | Clear, light yellow liquid with faint odor. Free of visible foreign matter and crystallized particles. |
| Terbinafine Assay | HPLC | 9.0 to 11.0% w/w | 9.9, 9.8 | 10.0 | 9.9 | 10.0 | 9.6 |

TABLE 43

Three-Month Stability of F132: 25° C., Ambient Humidity

| Attribute | Method | Limits | Initial | 1 month | 2 months | 3 months |
|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. |
| Terbinafine Assay | HPLC | 9.0 to 11.0% w/w | 9.8, 9.9 | 10.0 | 10.4 | 9.9 |

TABLE 44

Three-Month Stability of F132: 40° C., Ambient Humidity

| Attribute | Method | Limits | Initial | 1 month | 2 months | 3 months |
|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. |
| Terbinafine Assay | HPLC | 9.0 to 11.0% w/w | 9.8, 9.9 | 10.3 | 10.1 | 9.9 |

TABLE 45

Three-Month Stability of F133: 25° C., Ambient Humidity

| Attribute | Method | Limits | Initial | 1 month | 2 months | 3 months |
|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. |
| Terbinafine Assay | HPLC | 14.0 to 16.0% w/w | 14.9, 14.8 | 15.4 | 15.5 | 15.3 |

TABLE 46

Three-Month Stability of F133: 40° C., Ambient Humidity

| Attribute | Method | Limits | Initial | 1 month | 2 months | 3 months |
|---|---|---|---|---|---|---|
| Description | Visual | Clear, colorless to light yellow liquid or gel with a faint odor, essentially free | Clear, very light yellow liquid with faint odor. Free of visible particles or foreign matter | Clear, very light yellow liquid with strong odor. Free of visible particles or foreign | Clear, very light yellow liquid with strong odor. Free of visible particles or | Clear, very light yellow liquid with strong odor. Free of visible particles or |

TABLE 46-continued

Three-Month Stability of F133: 40° C., Ambient Humidity

| Attribute | Method | Limits | Initial | 1 month | 2 months | 3 months |
|---|---|---|---|---|---|---|
| | | of visible foreign matter and crystallized particles. | or crystallized particles. | matter or crystallized particles. | foreign matter or crystallized particles. | foreign matter or crystallized particles. |
| Terbinafine Assay | HPLC | 14.0 to 16.0% w/w | 14.9, 14.8 | 15.2 | 15.2 | 14.9 |

TABLE 47

Three-Month Stability of F142: 25° C., Ambient Humidity

| Attribute | Method | Limits | Initial | 1 month | 2 months | 3 months |
|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. |
| Terbinafine Assay | HPLC | 14.0 to 16.0% w/w | 15.7 | 14.7 | 15.3 | 15.3 |

TABLE 48

Three-Month Stability of F142: 40° C., Ambient Humidity

| Attribute | Method | Limits | Initial | 1 month | 2 months | 3 months |
|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible particles or foreign matter or crystallized particles. | Clear, very light yellow liquid with strong odor. Free of visible particles or foreign matter or crystallized particles. | Clear, very light yellow liquid with strong odor. Free of visible particles or foreign matter or crystallized particles. | Clear, very light yellow liquid with strong odor. Free of visible particles or foreign matter or crystallized particles. |
| Terbinafine Assay | HPLC | 14.0 to 16.0% w/w | 15.7 | 15.0 | 15.2 | 15.2 |

Figure 25:
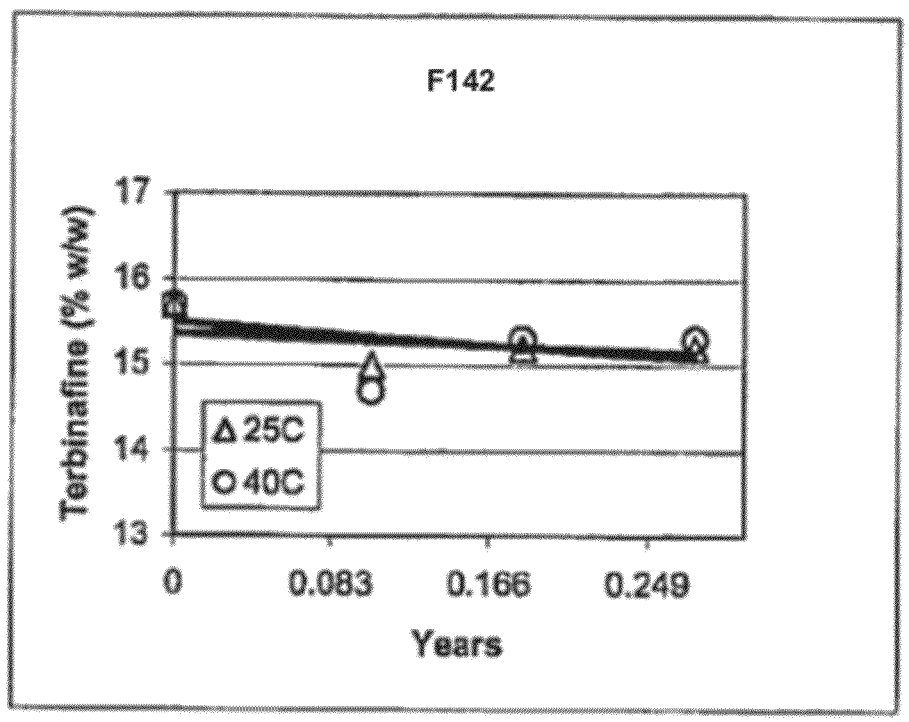
FIG. 25 illustrates the measured terbinafine content for F142 over time (Tables 47 and 48).

FIG. 25 shows the change in the measured terbinafine content of F142 at 25° C. and 40° C.

TABLE 49

Three-Month Stability of F143: 25° C., Ambient Humidity

| Attribute | Method | Limits | Initial | 1 month | 2 months | 3 months |
|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. |
| Terbinafine Assay | HPLC | 18.0 to 22.0% w/w | 20.0, 20.3 | 20.7 | 21.1 | 20.5 |

TABLE 50

Three-Month Stability of F143: 40° C., Ambient Humidity

| Attribute | Method | Limits | Initial | 1 month | 2 months | 3 months |
|---|---|---|---|---|---|---|
| Description | Visual | Clear, colorless to light yellow liquid or gel with a faint odor, essentially free of visible foreign matter and crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. | Clear, very light yellow liquid with faint odor. Free of visible particles or foreign matter or crystallized particles. |
| Terbinafine Assay | HPLC | 18.0 to 22.0% w/w | 20.0, 20.3 | 20.9 | 21.3 | 20.6 |

Example 24

Terbinafine Formulations I-B

TABLE 51

Terbinafine Formulations I-B

| Ingredients | F1-B | F2-B | F3-B | F4-B | F5-B | F6-B | F7-B | F8-B | F9-B |
|---|---|---|---|---|---|---|---|---|---|
| Terbinafine HCl | 10 | 10 | 10 | 10 | 10 | 10 | 10 | 10 | 10 |
| Disodium cocoamphodiacetate (DCAM) | 15 | | 15 | 15 | 15 | | | | |
| Ethanol | 30 | 45 | 45 | 45 | 35 | 55 | 42 | 50 | 40 |
| Urea | 15 | 15 | | 15 | 15 | | 15 | 20 | 20 |
| Water | 10 | 10 | 10 | 10 | 10 | 10 | 8 | 10 | 10 |
| Acetylcarnitine | 7.5 | 7.5 | 7.5 | | 7.5 | 7.5 | 7.5 | | |
| Carnitine | 7.5 | 7.5 | 7.5 | | 7.5 | 7.5 | 7.5 | | |
| Menthol | 5 | 5 | 5 | 5 | | | | | |
| Betaine | | | | | | | | 10 | 10 |
| Ammonium thioglycolate (60% aqueous solution) | | | | | | 10 | 10 | | 10 |

Table 75 FI-B = F6-B
Table 75 FII-B = F7-B

Figure 26A:
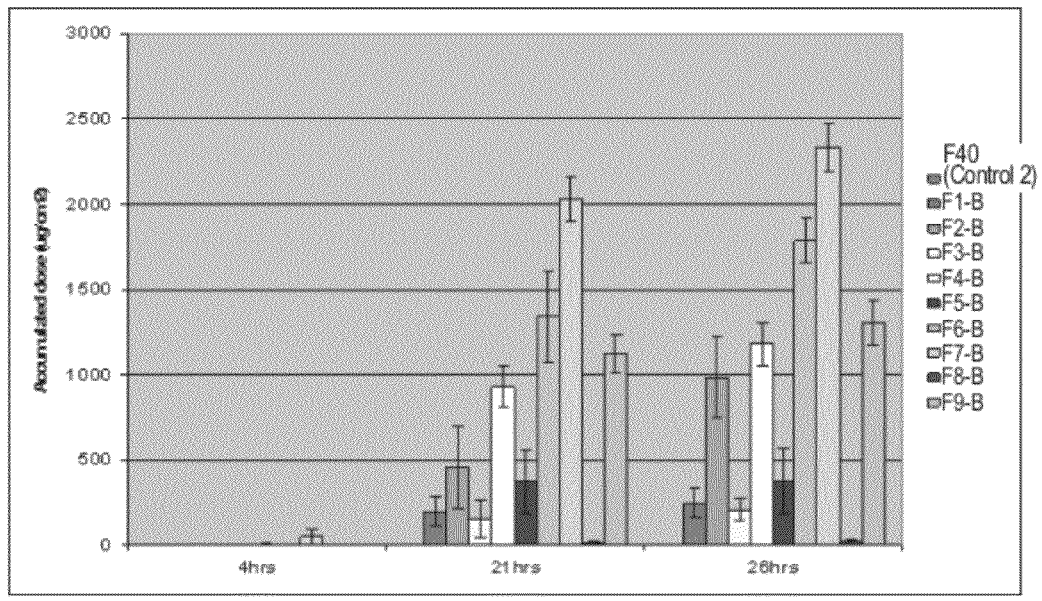
FIGS. 26A-B illustrate the results of shed snakeskin permeation studies on Formulations I-B (Table 51).
Figure 26B:
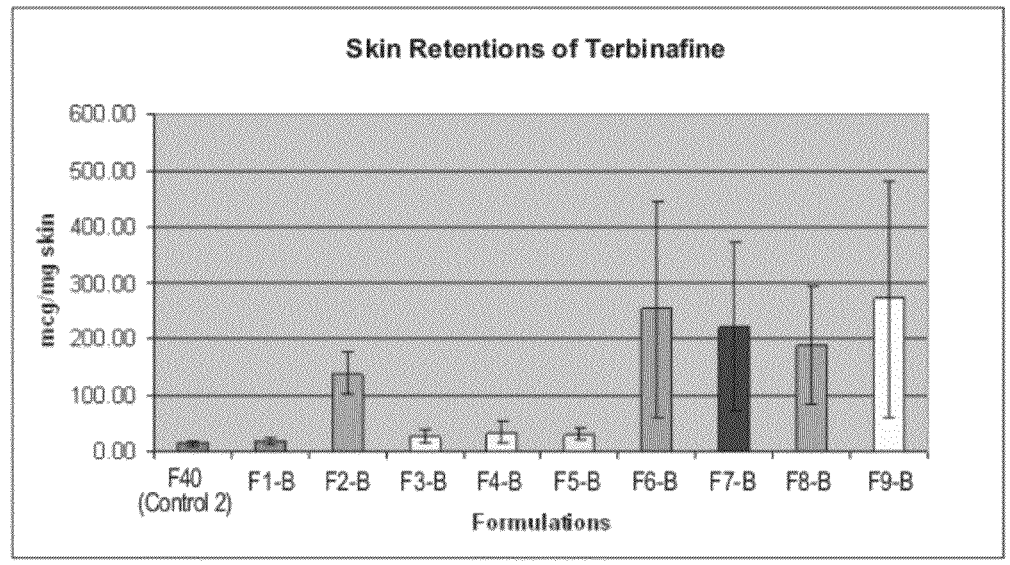

FIGS. 26A and 26B illustrate the results of transdermal studies on Formulations I-B.

FIG. 26A shows the permeation of active ingredient over time. FIG. 26B shows the total amount of active ingredient as a skin retention value.

Formulations F6-B and F7-B with carnitines and thioglycolates exhibited higher permeation enhancements.

Example 25

Terbinafine Formulations II-B

TABLE 52

Terbinafine Formulations II-B

| Ingredients | F11-B | F12-B | F13-B | F14-B | F15-B | F16-B | F17-B | F18-B | F19-B |
|---|---|---|---|---|---|---|---|---|---|
| Terbinafine HCl | 10 | 10 | 10 | 10 | 10 | 10 | 10 | 10 | 10 |
| Isethionate | | 10 | 10 | 10 | | | | 10 | 10 |
| Ethanol | 55 | 42.5 | 32.5 | 32.5 | 42.5 | 42.5 | 35 | 34 | 50 |
| Urea | | | | | 15 | 15 | 15 | 15 | |
| Water | 10 | 10 | 12.5 | 12.5 | 12.5 | 12.5 | 10 | 11 | 10 |
| Betaine | | | 10 | | | | | | |
| Carnitine | 7.5 | 7.5 | 7.5 | 7.5 | | | | | 7.5 |
| Acetyl carnitine | 7.5 | 7.5 | 7.5 | 7.5 | | | | | 7.5 |

TABLE 52-continued

Terbinafine Formulations II-B

| Ingredients | F11-B | F12-B | F13-B | F14-B | F15-B | F16-B | F17-B | F18-B | F19-B |
|---|---|---|---|---|---|---|---|---|---|
| Sulfobetaine | | | | 10 | | 10 | | 10 | |
| Menthol | | | | | | | | | 5 |
| Ammonium thioglycolate (60% aqueous solution) | 10 | 10 | 10 | 10 | 10 | 10 | 10 | 10 | 10 |

Sulfobetaine based formulations as replacement of carnitines, F16-B and F18-B, did not change active delivery comparable to carnitine/isethionate formulation (F12-B).

Figure 27A:
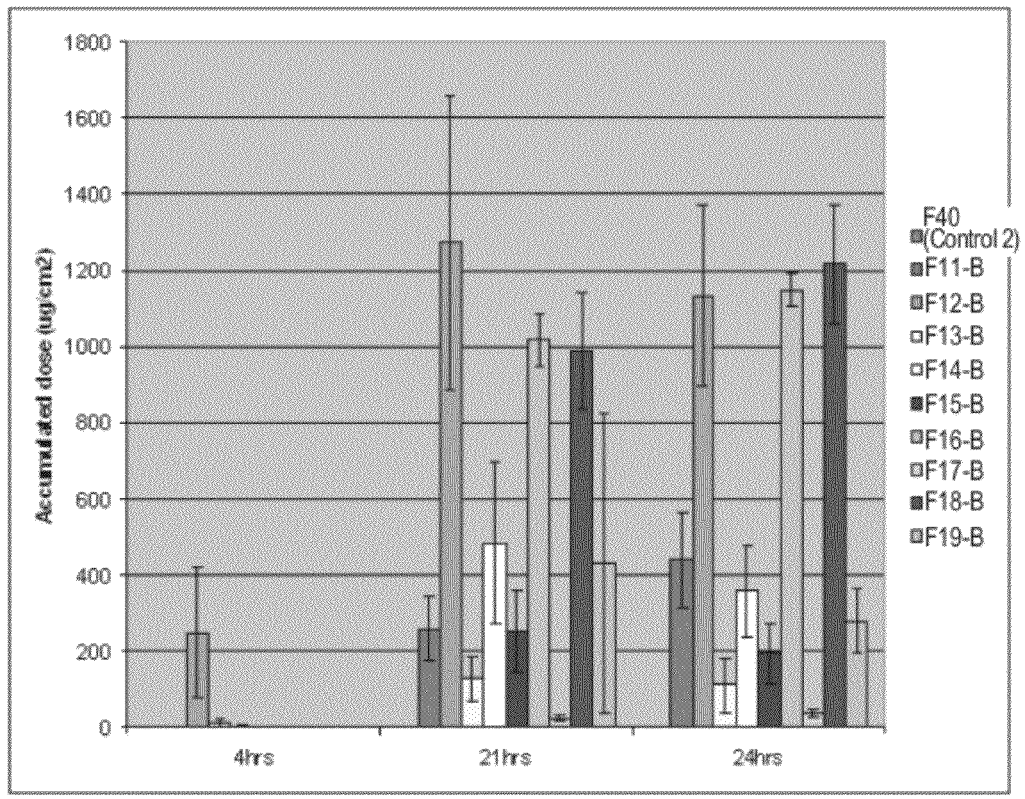
FIGS. 27A-B illustrate the results of shed snakeskin permeation studies on Formulations II-B (Table 52).
Figure 27B:
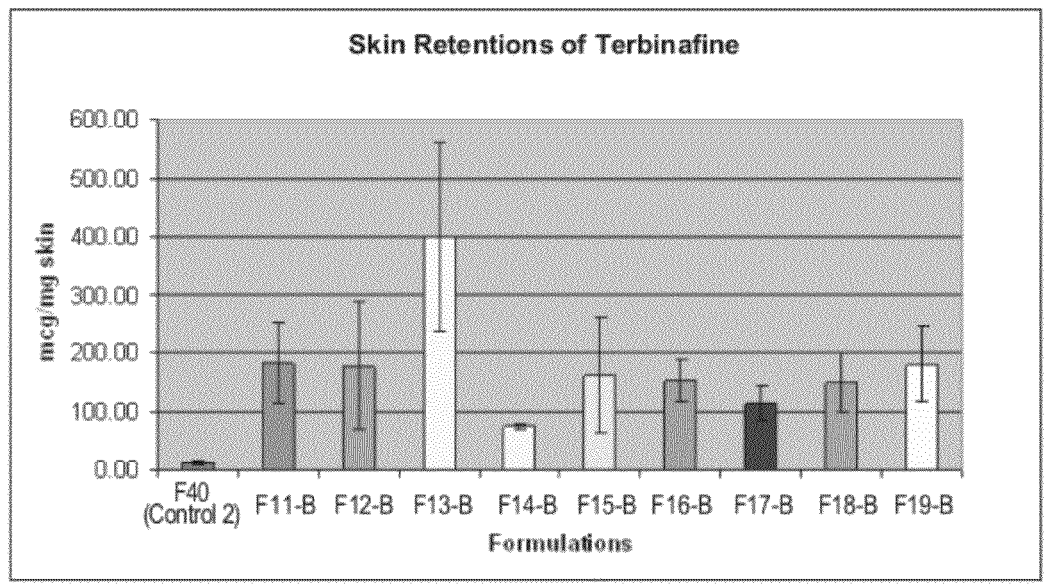

FIGS. 27A and 27B illustrate the results of transdermal studies on Formulations-II-B. FIG. 27A shows the permeation of active ingredient over time. FIG. 27B shows the total amount of active ingredient as a skin retention value.

Example 26

Terbinafine Formulations III-B

TABLE 53

Terbinafine Formulations III-B

| Ingredients | F21-B | F22-B | F23-B | F24-B | F25-B | F26-B | F27-B | F28-B | F29-B |
|---|---|---|---|---|---|---|---|---|---|
| Terbinafine HCl | 10 | 10 | 10 | 10 | 10 | 10 | 10 | 10 | 10 |
| Isethionate | | 10 | | | | | | | |
| Ethanol | 55 | 42.5 | 57.5 | 62.5 | 47.5 | 50 | 45 | 45 | 60 |
| Urea | | | | | | | | | |
| Water | 12.5 | 12.5 | 12.5 | 12.5 | 12.5 | 10 | 10 | 10 | 10 |
| Menthol | | | | | | 5 | 5 | 5 | 5 |
| Carnitine | 7.5 | 7.5 | | 7.5 | 7.5 | 7.5 | 7.5 | 7.5 | |
| Acetylcarnitine | 7.5 | 7.5 | | 7.5 | 7.5 | 7.5 | 7.5 | 7.5 | |
| Lactic acid | | | | | 5 | | 5 | | 5 |
| Acetic acid | | | | | | 5 | | 5 | |
| Ammonium thioglycolate (60% aqueous solution) | 10 | 10 | 10 | | 10 | 10 | 10 | 10 | 10 |

Table 75 FIII-B = F27-B
Table 75 FIV-B = F28-B

Formulations F27-B and F28-B were effective. They incorporated carnitines, ATG, a low molecular-weight acid, and menthol.

Figure 28A:
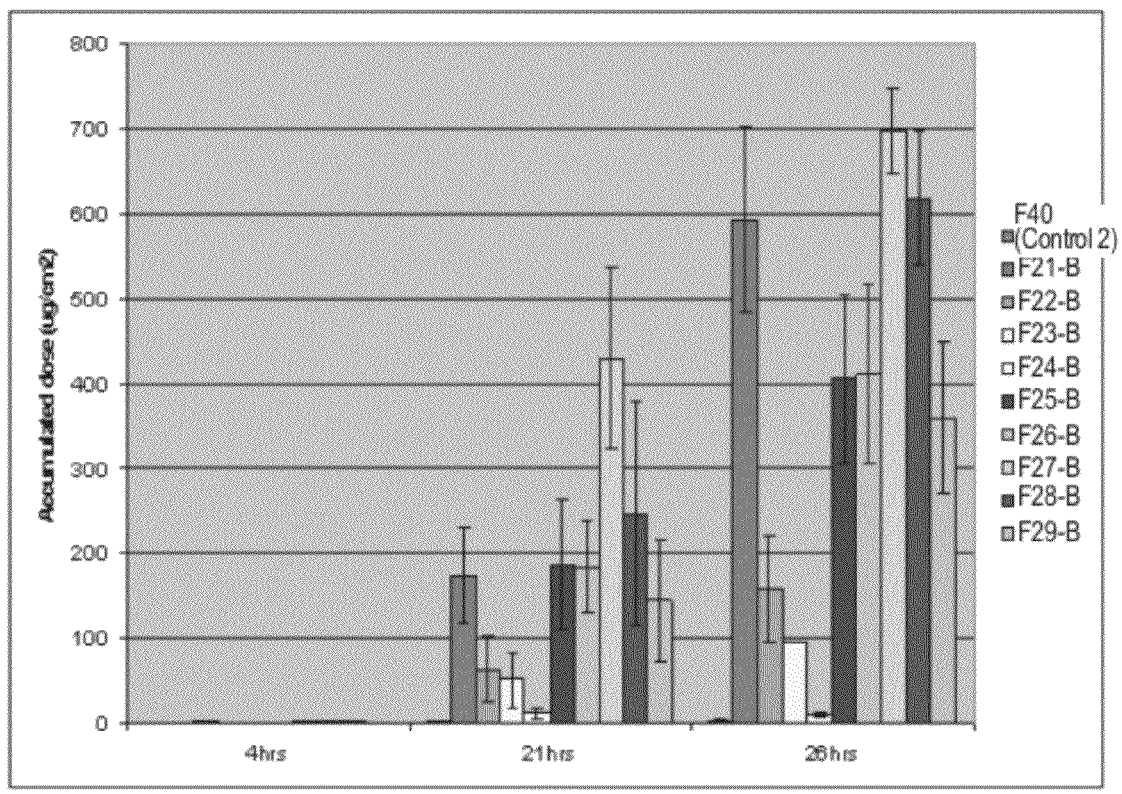
FIGS. 28A-B illustrate the results of shed snakeskin permeation studies on Formulations III-B (Table 53).
Figure 28B:
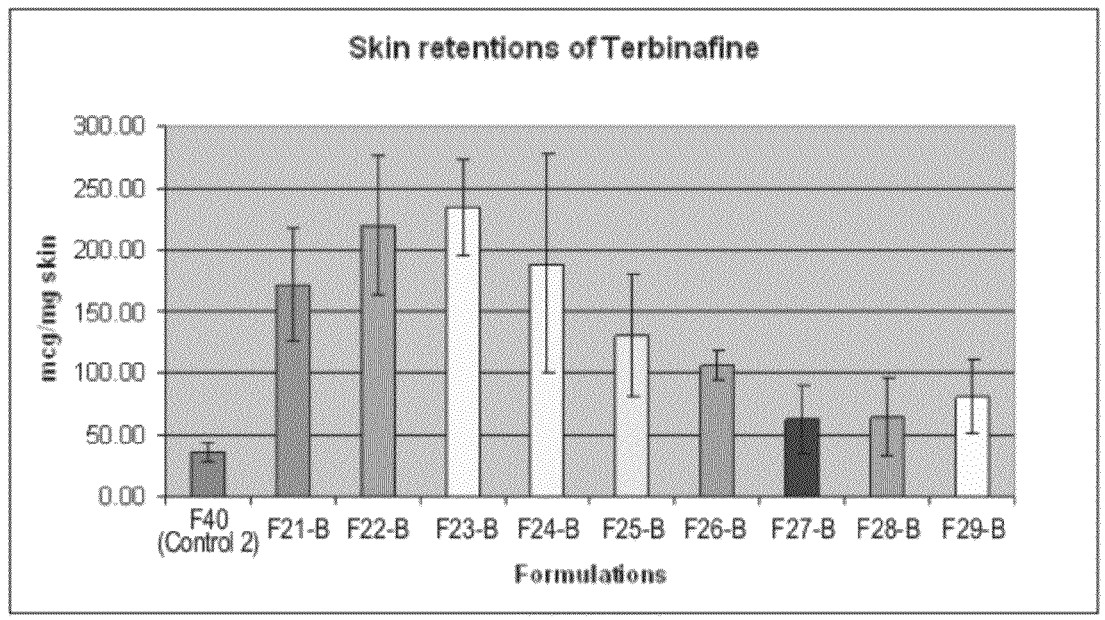

FIGS. 28A and 28B illustrate the results of transdermal studies on Formulations III-B. FIG. 28A shows the permeation of active ingredient over time. FIG. 28B shows the total amount of active ingredient as a skin retention value.

Example 27

Terbinafine Formulations IV-B

TABLE 54

Terbinafine Formulations IV-B

| Ingredients | F31-B | F32-B | F33-B | F34-B | F35-B |
|---|---|---|---|---|---|
| Terbinafine HCl | 10 | 10 | 10 | 10 | 10 |
| Ethanol | 45 | 40 | 45 | 43 | 43 |
| Carnitine | 7.5 | 7.5 | 7.5 | 7.5 | 7.5 |
| Acetylcarnitine | 7.5 | 7.5 | 7.5 | 7.5 | 7.5 |

TABLE 54-continued

Terbinafine Formulations IV-B

| Ingredients | F31-B | F32-B | F33-B | F34-B | F35-B |
|---|---|---|---|---|---|
| Ammonium thioglycolate (60% aqueous solution) | 10 | 10 | 10 | 10 | 10 |
| Lactic acid | 5 | 5 | 5 | 5 | 5 |
| Water | 10 | 10 | 10 | 10 | 10 |
| Polyvinylyrrolidone-30 | | | | | 5 |
| Hydroxypropylcellulose (HY117) | | | | 2 | |
| Phenol | | 5 | 5 | | |
| Menthol | 5 | 5 | | 5 | 5 |

Table 75 FV-B = F33-B
Table 75 FVI-B = F34-B
Table 75 FVII-B = F35-B

Carnitine formulation with menthol shows similar behavior to a phenol containing formulation. The addition of thickeners to carnitine/menthol formulations does not change permeation (F34-B).

Figure 29:
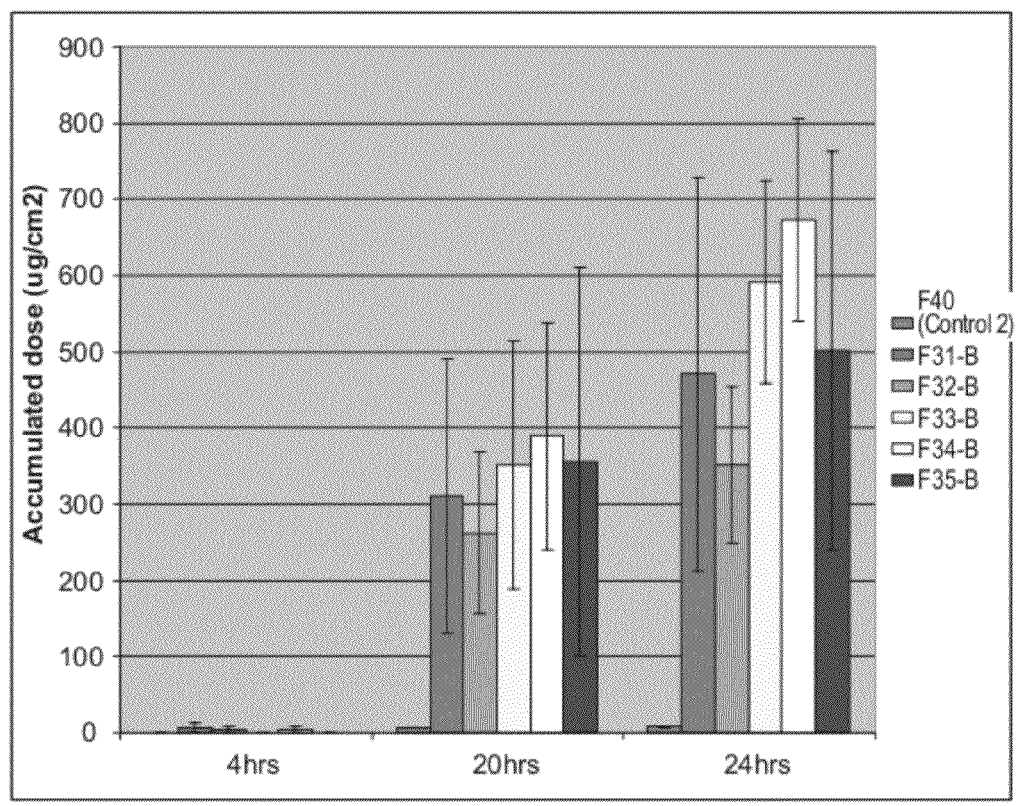
FIG. 29 illustrates the results of shed snakeskin permeation studies on Formulations IV-B (Table 54).

FIG. 29 illustrates the results of transdermal studies on Formulations IV-B. FIG. 29 shows the permeation of active ingredient over time.

Example 28

Terbinafine-Bovine Hoof Permeation V-B

TABLE 55

Terbinafine-Bovine Hoof Permeation V-B

| | Formulations V-B | | |
|---|---|---|---|
| Ingredients | F40 (Control) | F41-B | F42-B |
| Terbinafine HCl | Control 2 | 10 | 10 |
| Ethanol | | 43 | 43 |
| Water | | 10 | 10 |
| Lactic acid | | 5 | 5 |
| Ammonium thioglycolate (60% aqueous solution) | | 10 | 10 |
| Carnitine | | 7.5 | 7.5 |
| Acetyl carnitine | | 7.5 | 7.5 |
| menthol | | 5 | 5 |
| HPC HY 117 | | 2 | |
| Eudragit L100 | | | 2 |

Application at every sampling time = 5 μl
Table 75 FVI-B = F41-B
Table 75 FVIII-B = F42-B The carnitine formulation with thioglycolate and HPC HY117 exhibited a higher permeation profile than a similar formulation in which the HPC HY117 is replaced with Eudagrit L100. However, retention of terbinafine within the bovine hoof was much higher with the Eudagrit L100 formulation (F42-B).

Figure 30A:
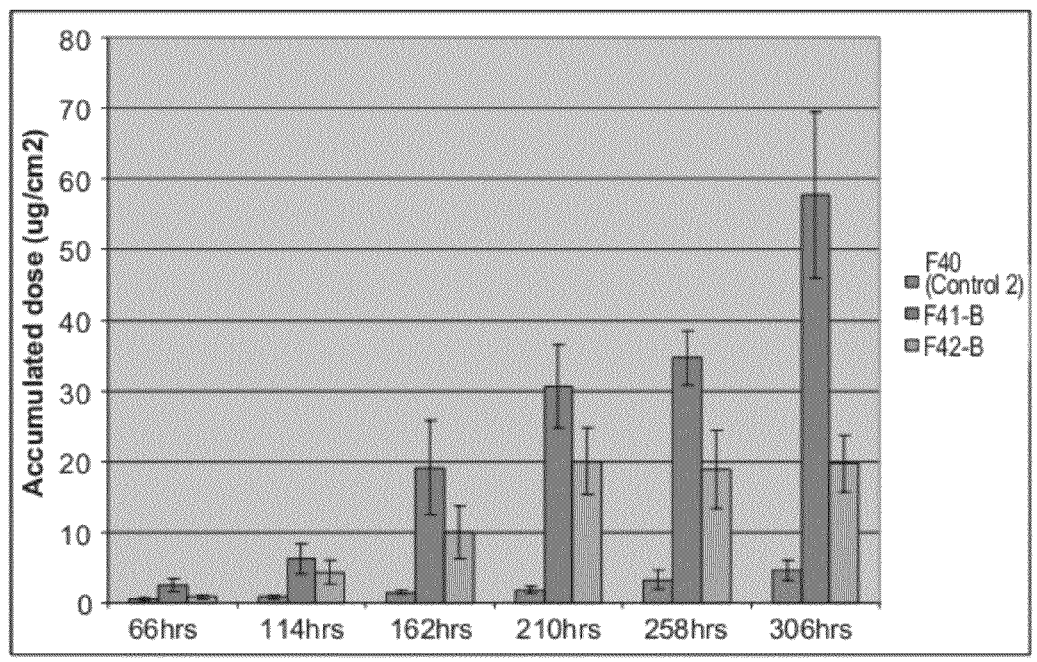
FIGS. 30A-B illustrate the results of bovine hoof permeation studies on Formulations V-B (Table 55).
Figure 30B:
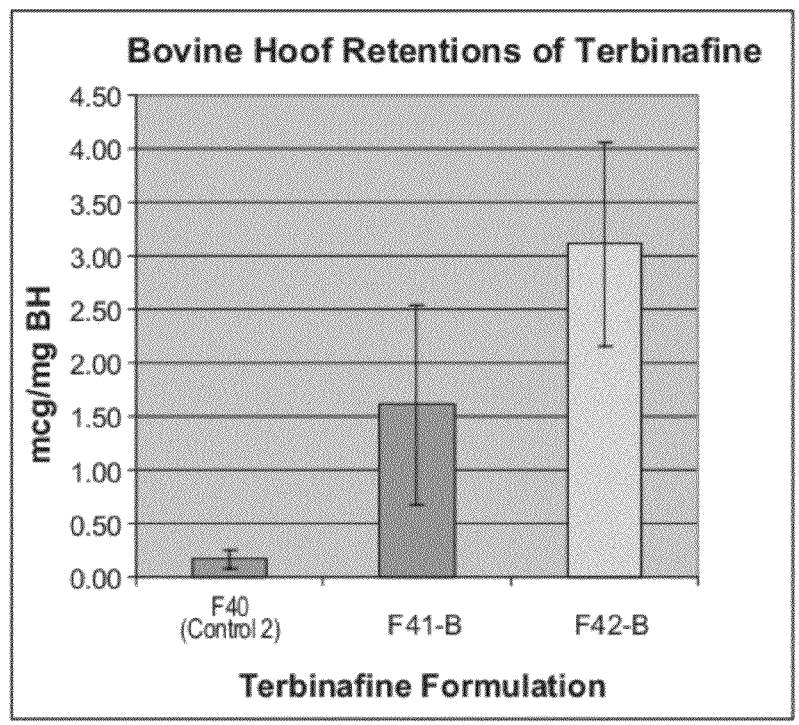

FIGS. 30A and 30B illustrate the results of transdermal studies on Formulations V-B. FIG. 30A shows the permeation of active ingredient over time. FIG. 30B shows the total amount of active ingredient as a skin retention value.

Example 29

Terbinafine-Bovine Hoof Permeation VI-B

TABLE 56

Terbinafine-Bovine Hoof Permeation VI-B

| | Formulations VI-B | | |
|---|---|---|---|
| Ingredients | F40 (Control) | F51-B | F52-B |
| Terbinafine HCl | Control 2 | 10 | |
| Ethanol | | 42 | |
| Water | | 7 | 10 |
| Lactic acid | | 4 | 1 |
| Carnitine | | 5 | |
| Acetylcarnitine | | 5 | |
| Menthol | | 3 | |
| Eudragit L-100 | | 2 | |
| Ammonium thioglycolate (60% aqueous solution) | | | 1 |
| Xanthan gum | | | 0.025 |

Table 75 FIX-B = F51-B, F52-B
T1 = F52-B + F51-B = 2 + 4 μl
T2 = F52-B + F51-B = 2 + 8 μl To enhance the stability, thioglycolate based formulations were divided into two components: (a) with active and (b) with thioglycolate gel and xanthan gum. Formulations with double the amount of drug-containing components exhibited good permeation.

Figure 31A:
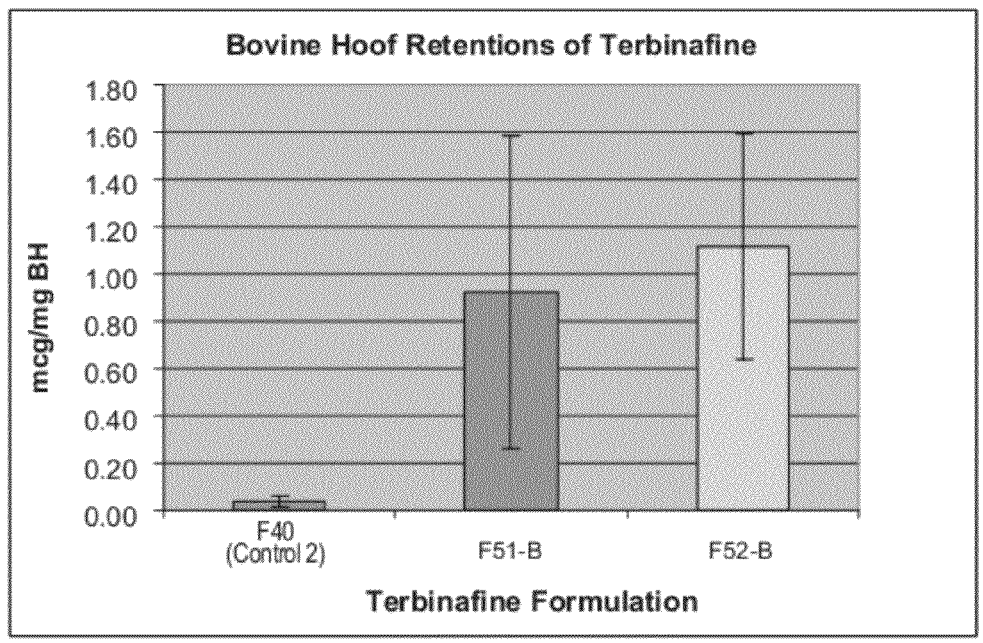
FIGS. 31A-B illustrate the results of bovine hoof permeation studies on Formulations VI-B (Table 56).
Figure 31B:
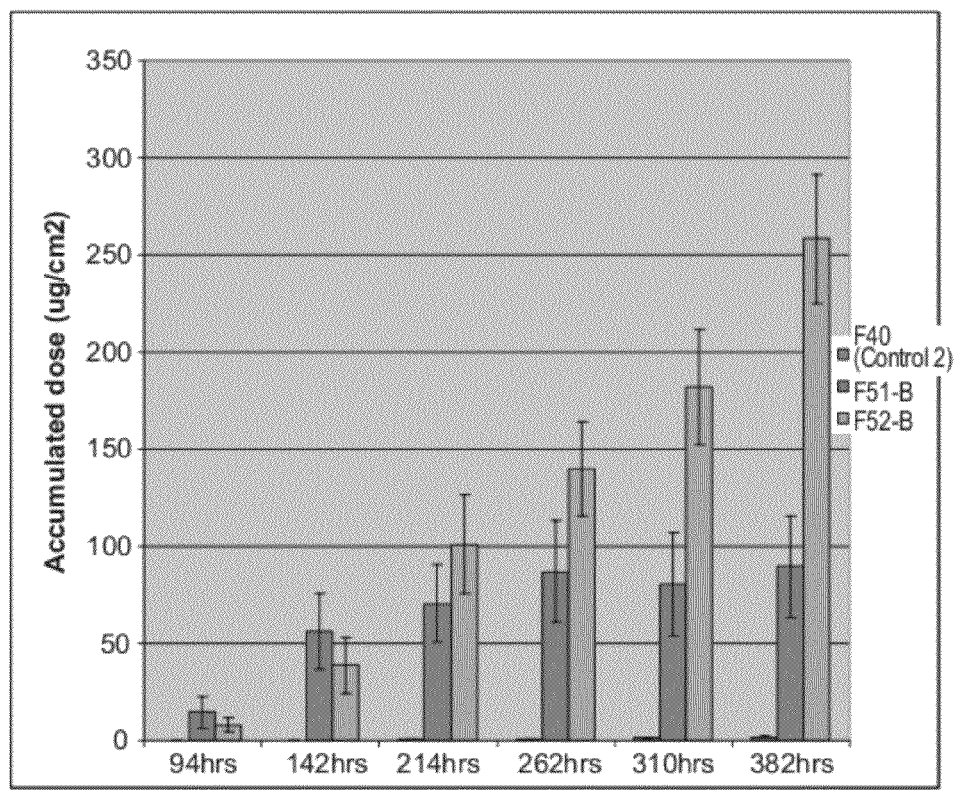

FIGS. 31A and 31B illustrate the results of transdermal studies on Formulations VI-B. FIG. 31A shows the total amount of active ingredient as a skin retention value; FIG. 31B shows the permeation of active ingredient over time.

Example 30

Terbinafine Permeation VII-B

TABLE 57

Terbinafine Permeation VII-B

| | Formulations-VII-B | | | | |
|---|---|---|---|---|---|
| Ingredients | F61-B | F62-B | F63-B | F64-B | F40 |
| | Part A | Part A | | | |
| Terbinafine HCl | 10 | 10 | 10 | 10 | Control 2 |
| Isethionate | 10 | | 10 | | |
| Ethanol | 40 | 42 | 41 | 45 | |
| Lactic acid | 4 | 4 | 5 | 5 | |
| Menthol | | 3 | | 3 | |
| Urea | 10 | 10 | 12 | 15 | |
| Water | 10 | 7 | | | |
| Eudragit L-100 | 2 | 2 | 2 | 2 | |
| Carnitine | | 5 | | 5 | |
| Acetyl carnitine | | 5 | | 5 | |
| | Part B | Part B | | | |
| Ammonium thio-glycolate (60% aqueous solution) | 10 | 10 | 10 | 10 | |
| Water | 7 | 7 | | | |
| Lactic acid | 1 | 1 | | | |
| Xanthan gum | 0.5 | 0.5 | | | |

Table 75 FX-B = F62-B

To enhance the stability, thioglycolate-based formulations were divided into two components: (a) with active and (b) with thioglycolate gel and xanthan gum. When compared to undivided formulations they exhibited similar permeation behaviors; however, no color change was observed.

Figure 32A:
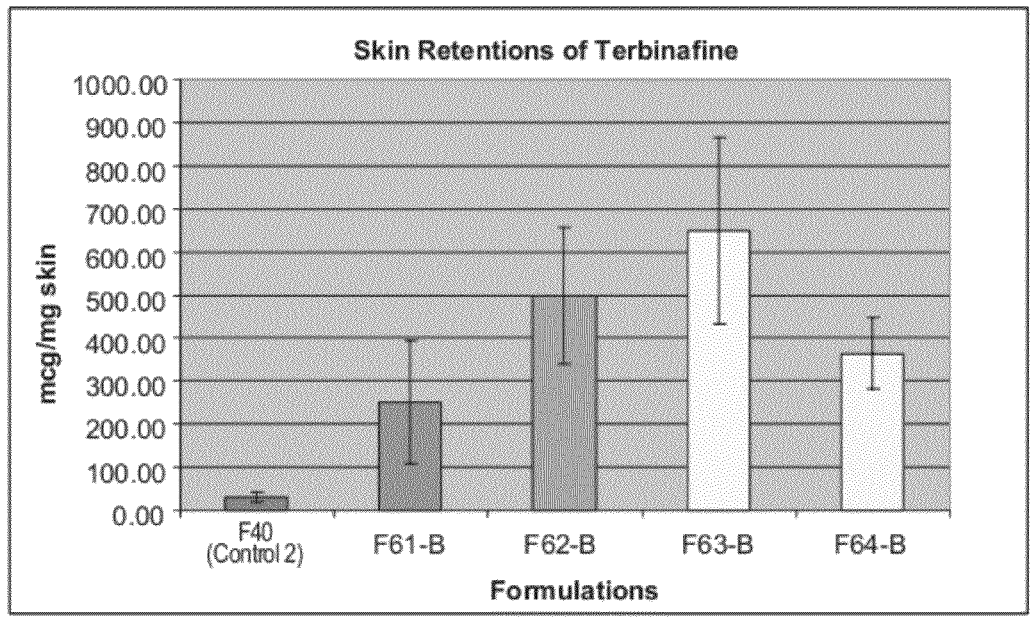
FIGS. 32A-B illustrate the results of shed snakeskin permeation studies on Formulations VII-B (Table 57).
Figure 32B:
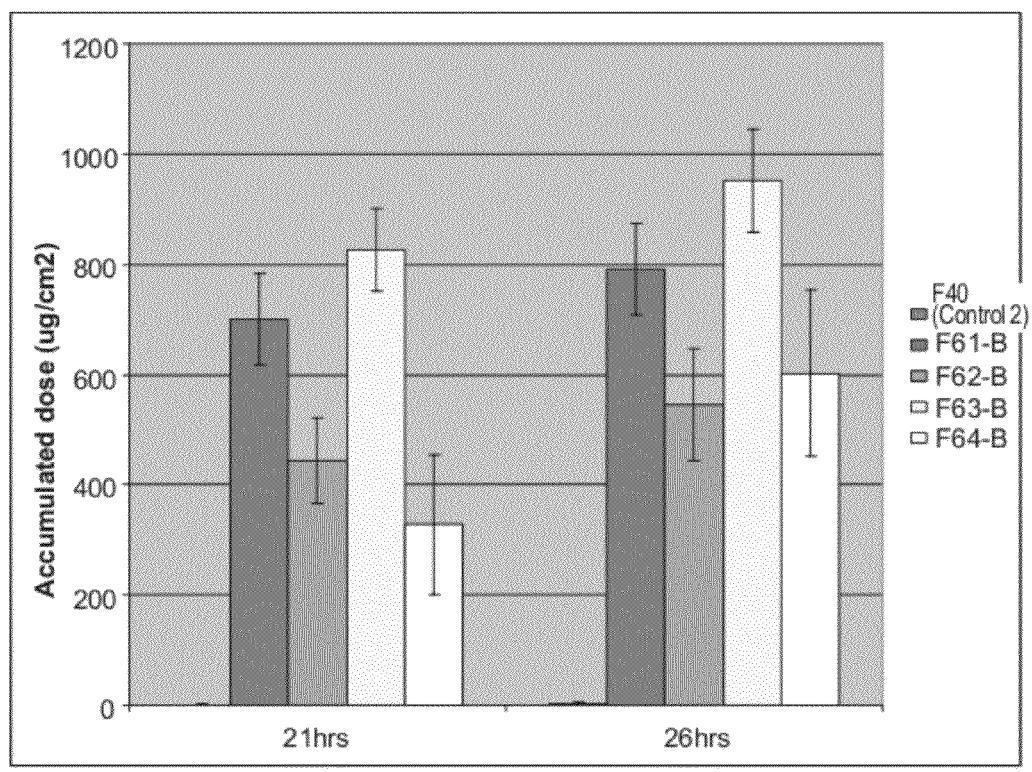

FIGS. 32A and 32B illustrate the results of transdermal studies on Formulations VII-B. FIG. 32A shows the total amount of active ingredient as a skin retention value; FIG. 32B shows the permeation of active ingredient over time.

Example 31

Terbinafine-Bovine Hoof Permeation VIII-B

TABLE 58

Terbinafine-Bovine Hoof Permeation VIII-B

| | Formulations-VIII-B | | | |
|---|---|---|---|---|
| Ingredients | F40 | F71-B | F72-B | F73-B |
| Terbinafine HCl | Control 2 | 10 | | |
| Ethanol | | 42 | | |
| Water | | 7 | 10 | 10 |
| Lactic acid | | 5 | | |
| Carnitine | | 5 | | |
| Acetylcarnitine | | 5 | | |
| Menthol | | 3 | | |
| Eudragit L-100 | | 2 | | |

TABLE 58-continued

Terbinafine-Bovine Hoof Permeation VIII-B

| | Formulations-VIII-B | | | |
|---|---|---|---|---|
| Ingredients | F40 | F71-B | F72-B | F73-B |
| Ammonium thio-glycolate (60% aqueous solution) | | | 10 | 10 |
| Xanthan gum | | | 0.025 | 0.025 |
| Bisulfite | | | | 0.003 |

F71-B + (F72-B or F73-B) = 2 + 4 µl
F71-B + (F72-B or F73-B) = 2 + 8 µl
Table 75 FX-B = F71-B To enhance the stability, thioglycolate-based formulations were divided into two components: (a) with active and (b) with thioglycolate gel and xanthan gum with or without bisulfate.

Figure 33A:
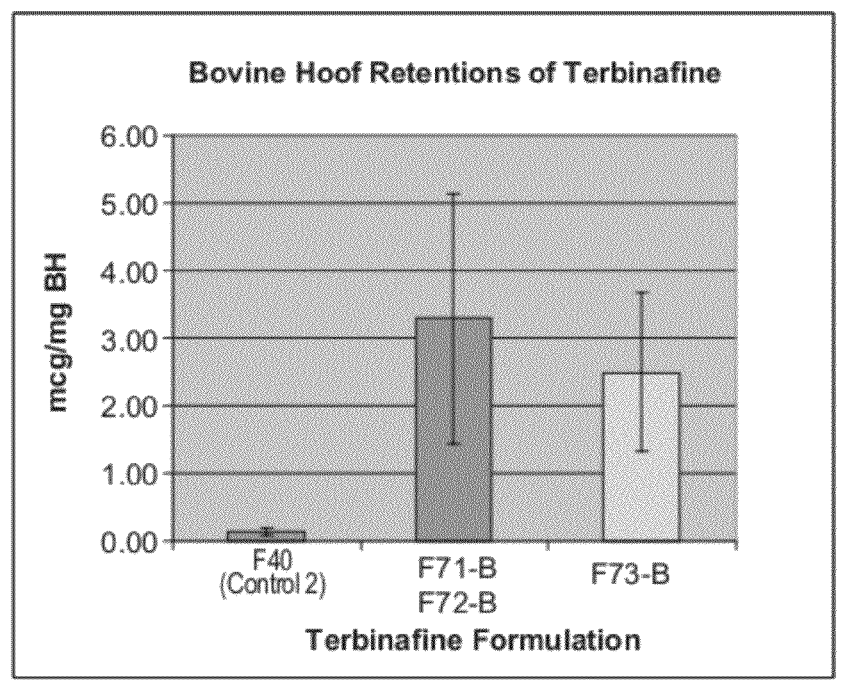
FIGS. 33A-B illustrate the results of bovine hoof permeation studies on Formulations VIII-B (Table 58).
Figure 33B:
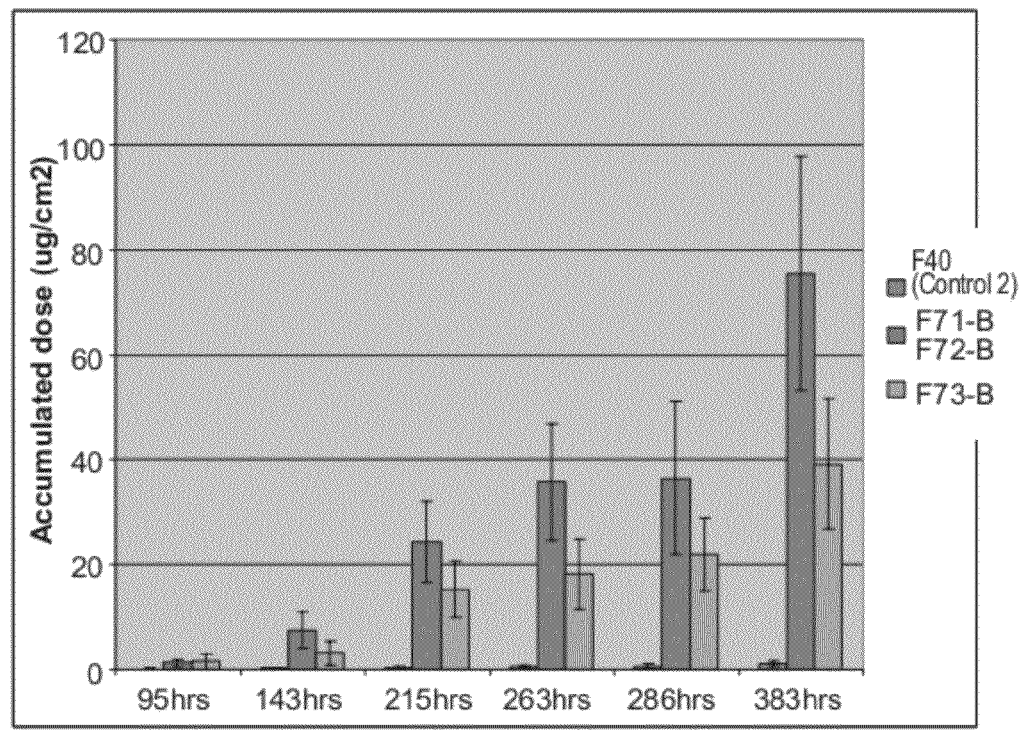

FIGS. 33A and 33B illustrate the results of transdermal studies on Formulations VIII-B. FIG. B 33A shows the total amount of active ingredient as a skin retention value; FIG. B 33B shows the permeation of active ingredient over time.

Example 32

Terbinafine Formulations IX-B

TABLE 59

Terbinafine Formulations IX-B

| | Formulations IX-B | | | | | | | | |
|---|---|---|---|---|---|---|---|---|---|
| Ingredients | F81-B | F82-B | F83-B | F84-B | F85-B | F86-B | F87-B | F88-B | F89-B |
| Terbinafine HCl | 10 | 10 | 10 | 10 | 10 | 10 | 10 | 10 | 10 |
| Ethanol | 60 | 55 | 62 | 52 | 65 | 62 | 57 | 52 | 49 |
| Water | 15 | 15 | 15 | 15 | 15 | 15 | 15 | 15 | 15 |
| Urea | | 5 | | 5 | | | | 5 | 5 |
| Carnitine | 5 | 5 | 5 | 5 | 5 | 5 | 5 | 5 | 5 |
| Acetyl carnitine | 5 | 5 | 5 | 5 | 5 | 5 | 5 | 5 | 5 |
| Lactic acid | 5 | 5 | | 5 | | | 5 | 5 | 5 |
| Menthol | | | 3 | 3 | | 3 | | | 3 |
| Glycerin mono laurate (GML) | | | | | | | 3 | 3 | 3 |

Table 75 FXI-B = F81-B
Table 75 FXII-B = F82-B
Table 75 FXIII-B = F87-B

Carnitine formulations with lactic acid show better permeation than their menthol containing versions (F81-B vs. F83-B and F82-B vs. F84-B). Addition of GML as replacement of menthol increases the permeation (F87-B).

Figure 34:
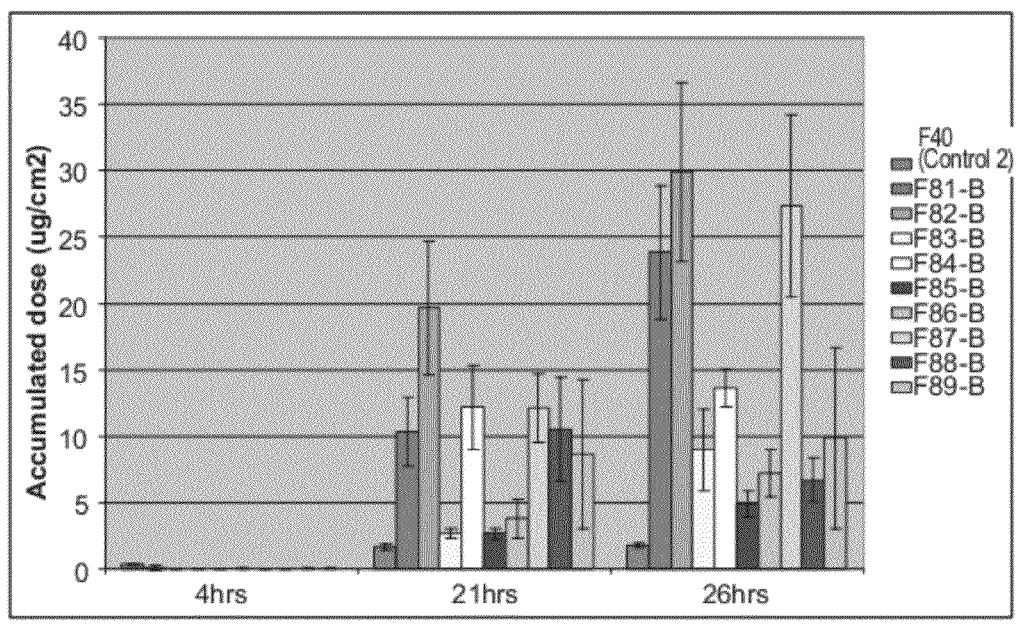
FIG. 34 illustrates the results of shed snakeskin permeation studies on Formulations IX-B (Table 59).

FIG. 34 illustrates the results of transdermal studies on Formulations IX-B. FIG. 34 shows the permeation of active ingredient over time.

Example 33

Terbinafine Formulations I-C

TABLE 60

Terbinafine Formulations I-C

| | Formulations | | | | |
|---|---|---|---|---|---|
| Ingredients | F40 | F91-B | F92-B | F93-B | F24 |
| Terbinafine hydrochloride | Control 2 | 10 | 10 | 10 | Control 1 |
| Disodium cocoamphodiacetate | | 15 | 15 | 15 | |
| Ethanol | | 40 | 39.5 | 40 | |
| Urea | | 15 | 15 | 15 | |
| Water | | 14 | 8 | 14 | |
| Menthol | | | 5 | | |
| Panthenol | | | 7.5 | | |
| Potassium thio-glycolate | | 6 | | | |
| Ammonium thio-glycolate (60% aqueous solution) | | | | 6 | |

Table 76 FI-C = F91-B
Table 76 FII-C = F93-B

Two salts of thioglycolic acid were examined (F91-B vs. F93-B). Although potassium salt of thioglycolic acid exhibited higher permeation, later studies were performed with the ammonium salt, which gave better formulation characteristics with even higher permeation.

Figure 35A:
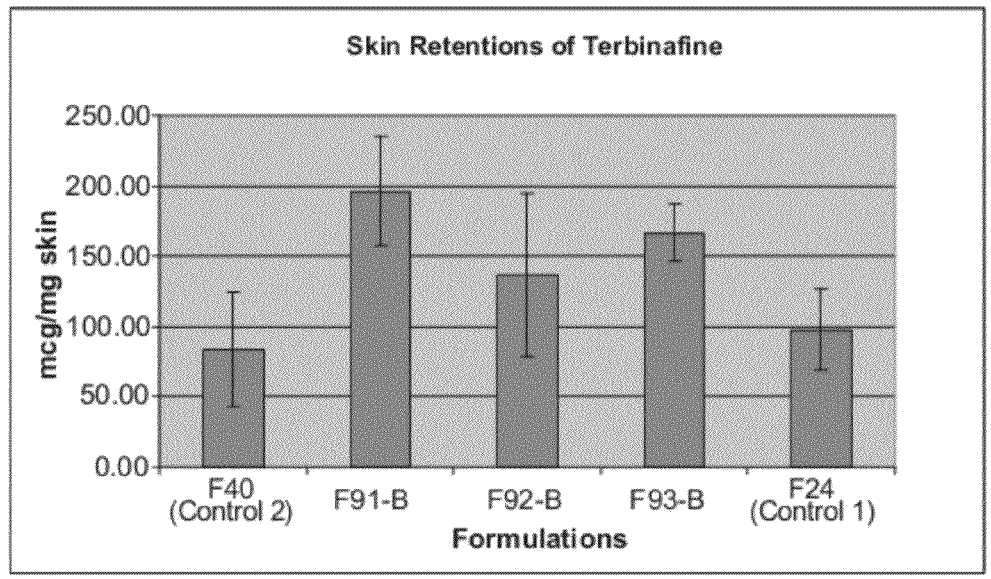
FIGS. 35A-B illustrate the results of shed snakeskin permeation studies on Formulations I-C (Table 60).
Figure 35B:
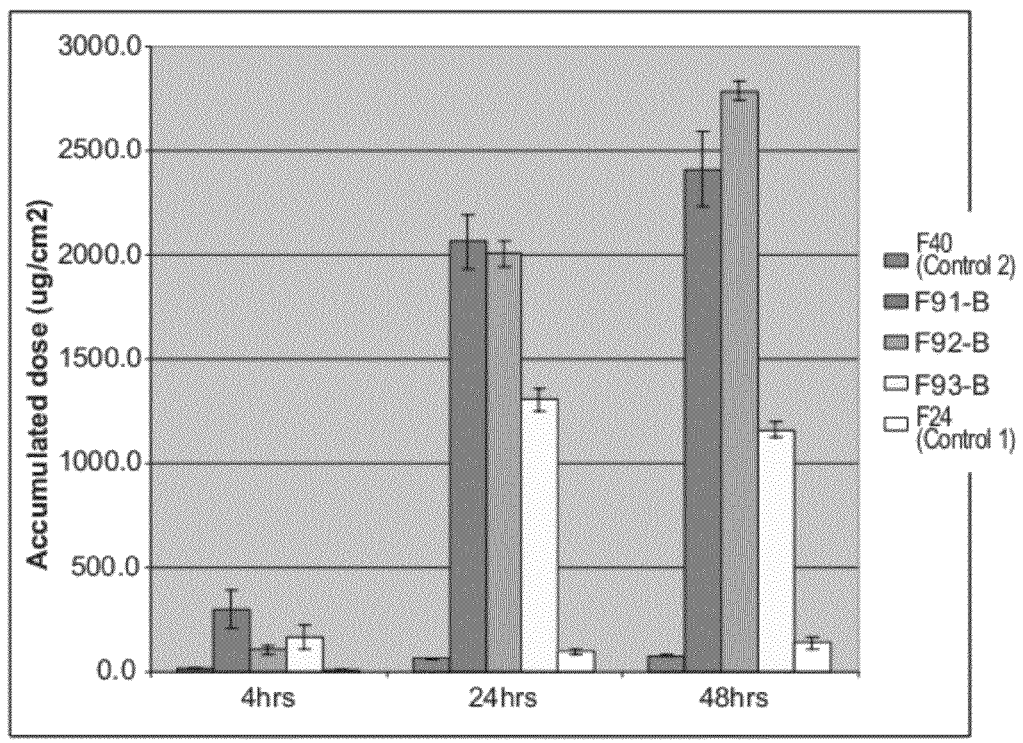

FIGS. 35A and 35B illustrate the results of transdermal studies on Formulations I-C. FIG. 35A shows the total amount of active ingredient as a skin retention value; FIG. 35B shows the permeation of active ingredient over time.

Example 34

Terbinafine Formulations II-C

TABLE 61

Terbinafine Formulations II-C

| Ingredients | Formulations II-C | | | | | | | | |
|---|---|---|---|---|---|---|---|---|---|
| | F101-B | F102-B | F103-B | F104-B | F105-B | F106-B | F107-B | F108-B | F109-B |
| Terbinafine hydrochloride | 10 | 10 | 10 | 10 | 10 | 10 | 10 | 10 | 10 |
| Disodium cocoamphodiacetate | 15 | | 15 | | 15 | | | | |
| Ethanol | 44 | 57 | 57 | 64 | 41 | 45 | 58 | 50 | 39 |
| Isethionate | | | | | | 10 | 10 | 10 | 10 |
| Urea | 15 | 15 | | | 15 | 15 | | | |
| Water | 10 | 12 | 12 | 20 | 8 | 20 | 22 | 22 | 20 |
| Menthol | | | | | 5 | | | | |
| Sodium thioglycolate | 6 | 6 | 6 | 6 | 6 | | | 6 | 6 |

Table 76 FIII-C = F109-B

A combination of sodium isethionate and thioglycolate gave better permeation than the DCAM/thioglycolate formulations (F109-B vs. F101-B).

Figure 36A:
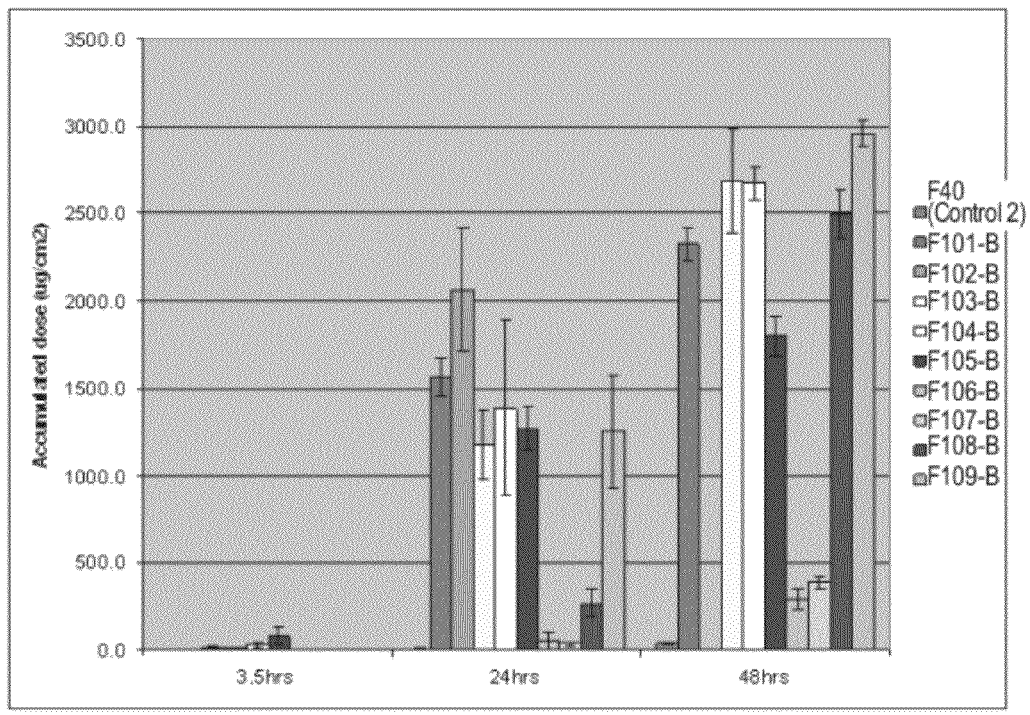
FIGS. 36A-B illustrate the results of shed snakeskin permeation studies on Formulations II-C (Table 61).
Figure 36B:
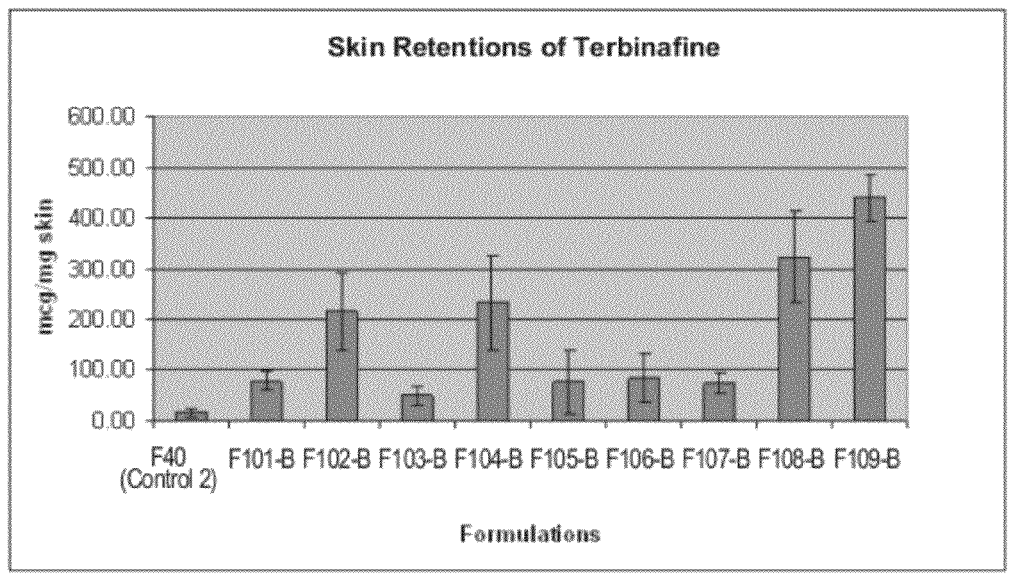

FIGS. 36A and 36B illustrate the results of transdermal studies on Formulations II-C. FIG. 36A shows the permeation of active ingredient over time; FIG. 36B shows the total amount of active ingredient as a skin retention value.

Example 35

Formulations Developments: Terbinafine Formulations III-C

TABLE 62

Formulations Developments: Terbinafine Formulations III-C

| Ingredients | Formulations III-C | | | | | | | | |
|---|---|---|---|---|---|---|---|---|---|
| | F111-B | F112-B | F113-B | F114-B | F115-B | F116-B | F117-B | F118-B | F119-B |
| Terbinafine HCl | 10 | 10 | 10 | 10 | 10 | 10 | 10 | 10 | 10 |
| Isethionate | | 10 | 10 | 10 | 10 | 10 | 8 | | 10 |
| Ethanol | 51 | 42 | 54 | 55 | 39 | 45 | 42 | 44 | 37 |
| Urea | 15 | 15 | | | 15 | 5 | 15 | 15 | 15 |
| Water | 14 | 13 | 16 | 20 | 6 | 20 | 13 | 16 | 13 |
| Na-laurylsulfate | | | | | | | 2 | 5 | |
| Tween 80 | | | | | | | | | 5 |
| Ammonium thioglycolate (60% aqueous solution) | 10 | 10 | 10 | | 20 | 10 | 10 | 10 | 10 |

TABLE 76 FIV-C = F112-B
TABLE 76 FV-C = F119-B

The effect of the amount of thioglycolate on the delivery (F111-B vs. F115-B) was examined.

Figure 37A:
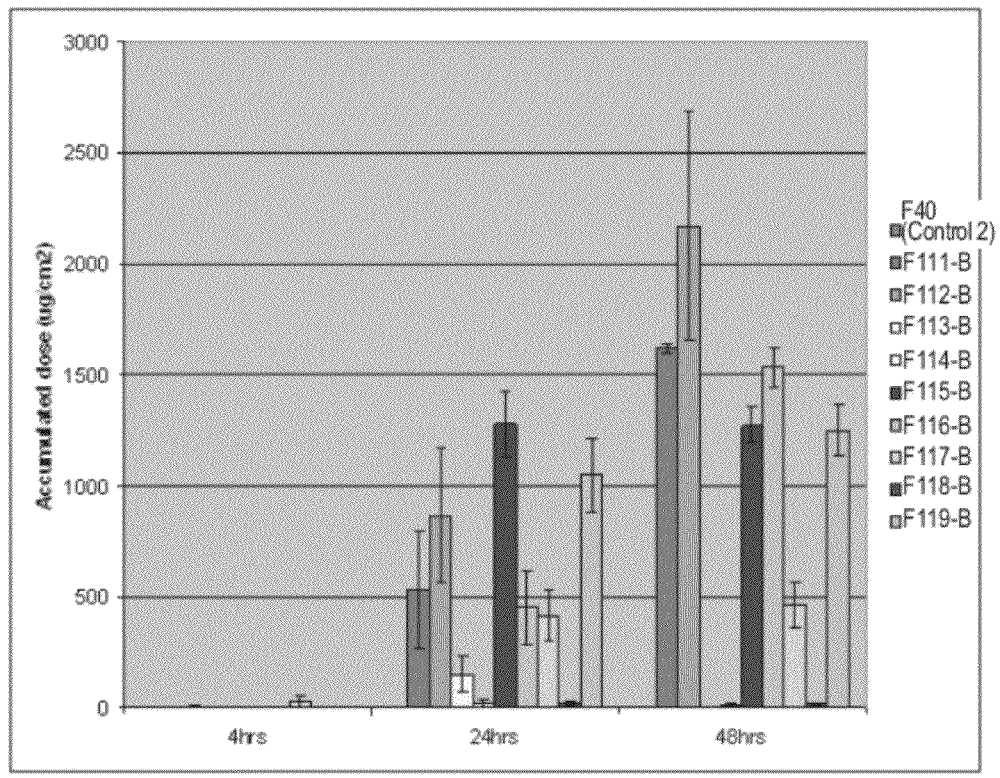
FIGS. 37A-B illustrate the results of shed snakeskin permeation studies on Formulations III-C (Table 62).
Figure 37B:
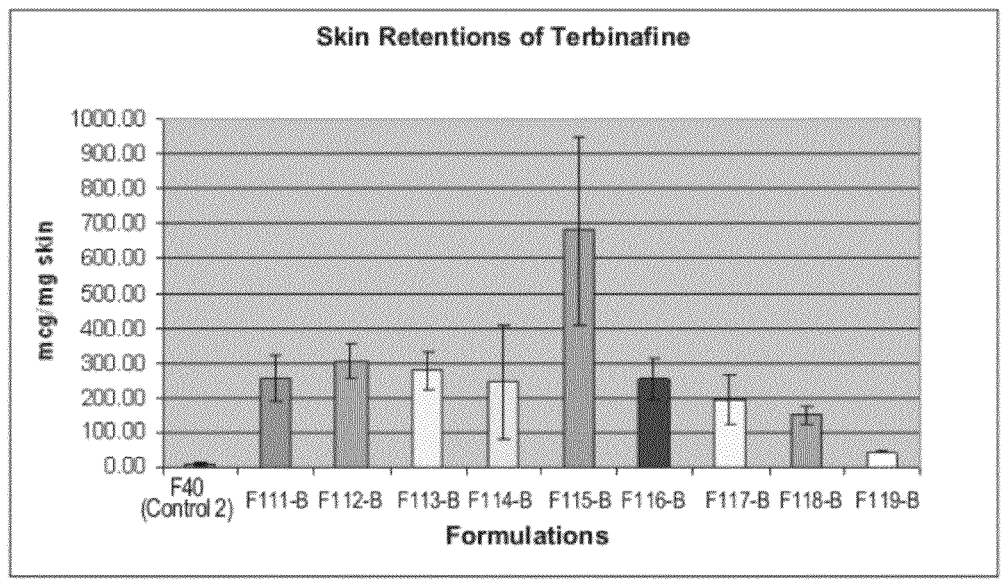

FIGS. 37A and 37B illustrate the results of transdermal studies on Formulations III-C. FIG. 37A shows the permeation of active ingredient over time; FIG. 37B shows the total amount of active ingredient as a skin retention value.

Example 36

Terbinafine Formulations IV-C

TABLE 63

Terbinafine Formulations IV-C

| Ingredients | F121-B | F122-B | F123-B | F124-B | F125-B | F126-B | F127-B | F128-B | F129-B |
|---|---|---|---|---|---|---|---|---|---|
| Terbinafine HCl | 10 | 10 | 10 | 10 | 10 | 10 | 10 | 10 | 10 |
| Isethionate | 10 | 10 | 10 | 10 |  | 10 | 10 |  |  |
| Ethanol | 45 | 50 | 45 | 39 | 50 | 40 | 40 | 50 | 45 |
| Urea | 15 | 15 | 15 | 15 | 15 | 15 | 15 | 15 | 15 |
| Water | 10 | 10 | 10 | 11 | 10 | 10 | 10 | 10 | 10 |
| Octyl trimethyl-ammonium bromide |  |  |  | 5 |  |  |  |  |  |
| Tween 80 |  |  | 5 |  |  |  |  |  |  |
| Chloroacetic acid |  | 5 | 5 |  |  |  |  |  | 5 |
| Lauric diethanolamine |  |  |  |  | 5 |  |  |  |  |
| Panthenol |  |  |  |  |  | 15 |  |  | 15 |
| Stearyl lactylate |  |  |  |  |  |  | 5 | 5 |  |
| Ammonium thioglycolate (60% aqueous solution) | 10 |  |  | 10 | 10 |  | 10 | 10 |  |

Table 76 FVI-C = F124-B

Formulation F1-B with a cationic detergent (F124-B) appears to enhance the delivery further.

Figure 38A:
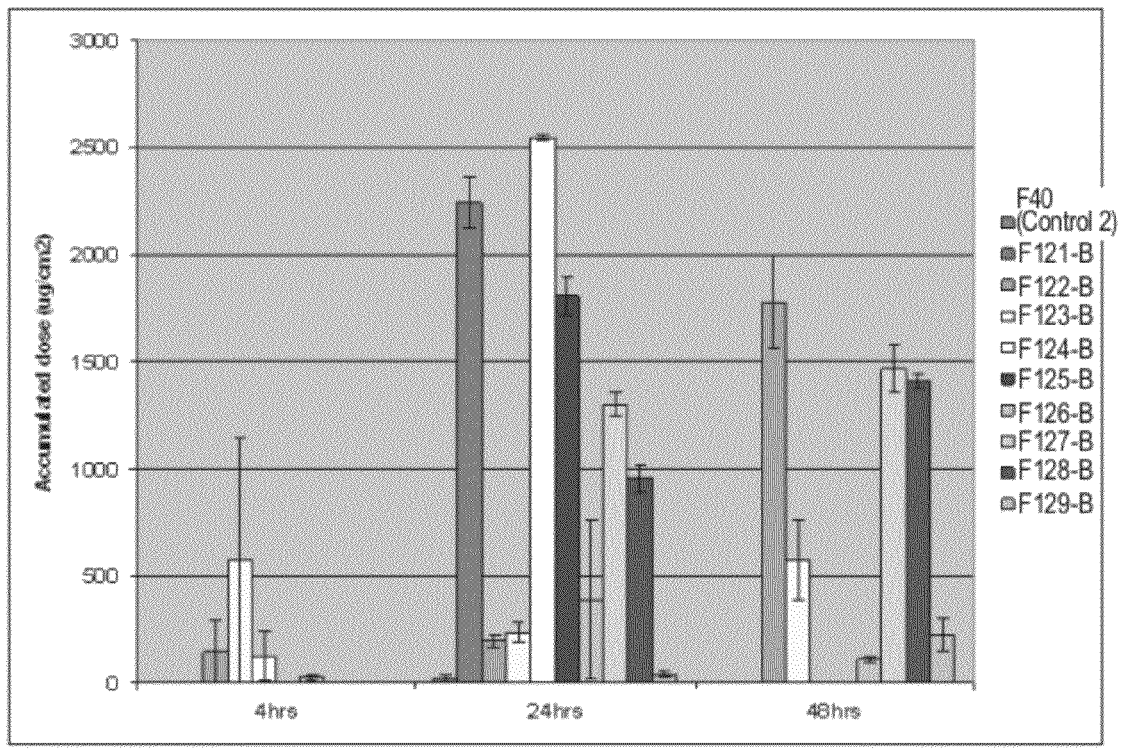
FIGS. 38A-B illustrate the results of shed snakeskin permeation studies on Formulations IV-C (Table 63).
Figure 38B:
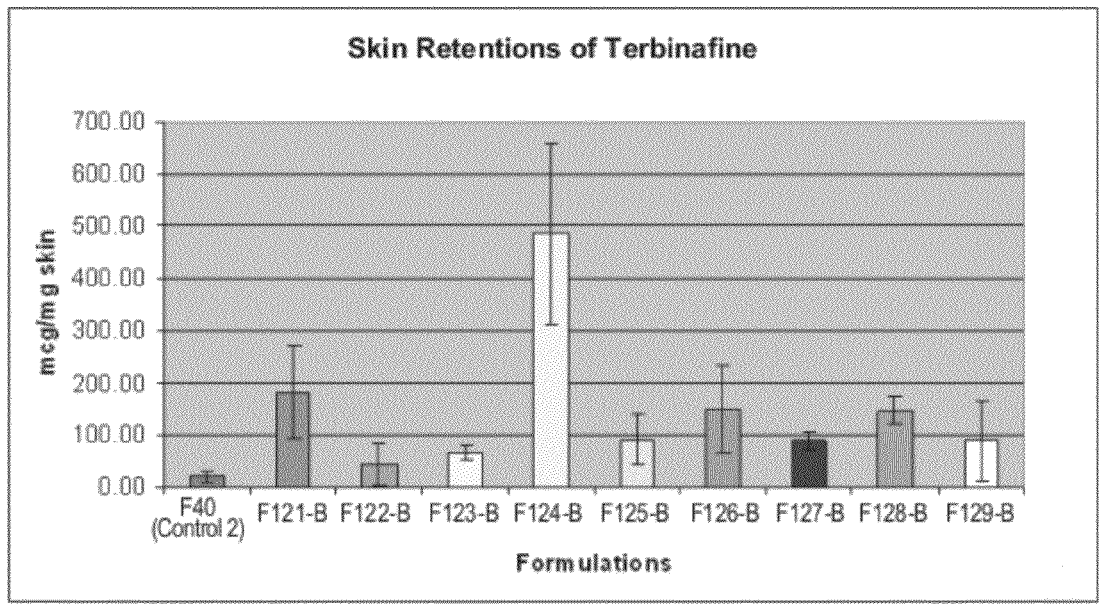

FIGS. 38A and 38B illustrate the results of transdermal studies on Formulations IV-C. FIG. 38A shows the permeation of active ingredient over time; FIG. 38B shows the total amount of active ingredient as a skin retention value.

Example 37

Terbinafine Formulations V-C

TABLE 64

Terbinafine Formulations V-C

| Ingredients | F131-B | F132-B | F133-B | F134-B | F135-B | F136-B | F137-B | F138-B | F139-B |
|---|---|---|---|---|---|---|---|---|---|
| Terbinafine HCl | 10 | 10 | 10 | 10 | 10 | 10 | 10 | 10 | 10 |
| Isethionate | 10 | 10 |  | 10 | 10 | 10 | 10 | 10 | 15 |
| Ethanol | 39 | 44 | 49 | 49 | 37 | 39 | 39 | 44 | 39 |
| Urea | 15 | 15 | 15 | 15 | 15 | 15 | 15 | 15 | 15 |
| Water | 11 | 11 | 11 | 11 | 13 | 11 | 10 | 15 | 11 |
| Octyl trimethyl-ammonium bromide | 5 |  | 5 | 5 |  |  |  |  |  |
| Tween 80 |  |  |  |  | 5 |  |  |  |  |
| Cetyl trimethyl-ammonium bromide |  |  |  |  |  | 5 |  |  |  |
| Sodium nitrite |  |  |  |  |  |  | 6 | 6 |  |
| Ammonium thioglycolate (60% aqueous solution) | 10 | 10 | 10 |  | 10 | 10 | 10 |  | 10 |

Table 76 FVII-C = F136-B

Addition of non-ionic detergent to F1-B (F135-B) and cationic detergent (F136-B) enhances the permeation further. Increasing the sodium isethionate level also enhances the delivery (F132-B vs. F139-B).

Figure 39A:
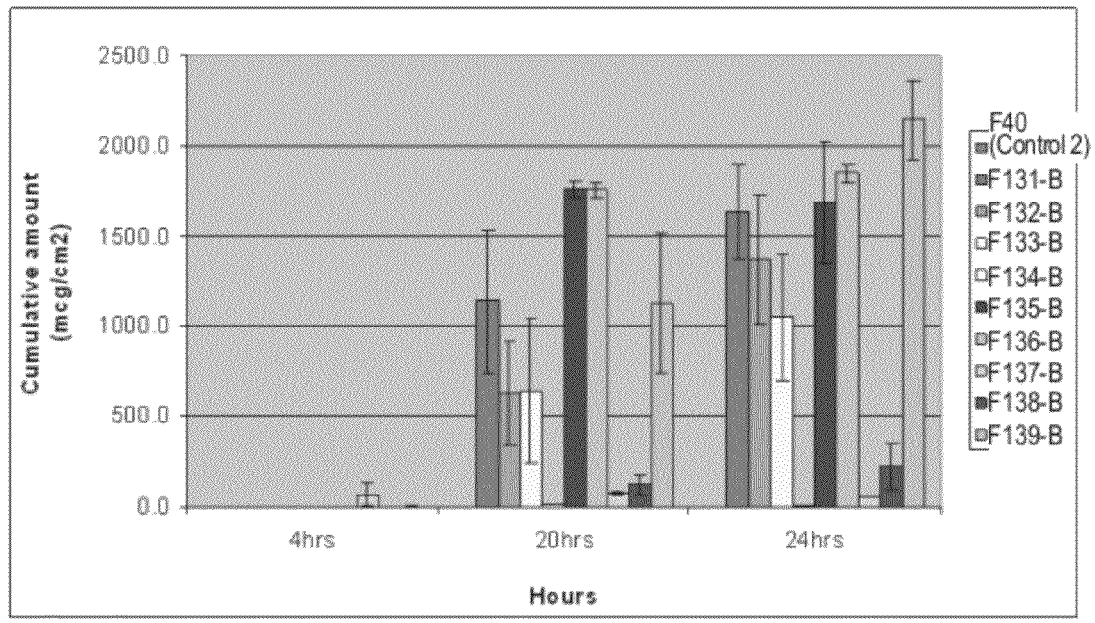
FIGS. 39A-B illustrate the results of shed snakeskin permeation studies on Formulations V-C (Table 64).
Figure 39B:
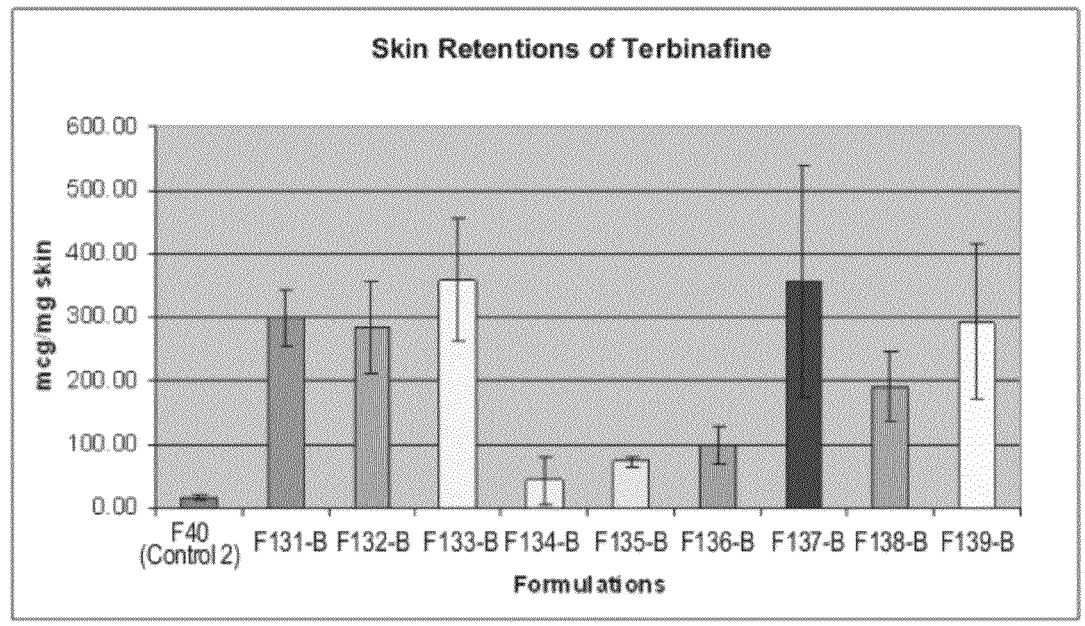

FIGS. 39A and 39B illustrate the results of transdermal studies on Formulations V-C. FIG. 39A shows the permeation of active ingredient over time; FIG. 39B shows the total amount of active ingredient as a skin retention value.

Example 38

Terbinafine Formulations VI-C

TABLE 65

Terbinafine Formulations VI-C

| Ingredients | Formulations VI-C | | | | | | | | |
|---|---|---|---|---|---|---|---|---|---|
| | F141-B | F142-B | F143-B | F144-B | F145-B | F146-B | F147-B | F148-B | F149-B |
| Terbinafine HCl | 10 | 10 | 10 | 10 | 10 | 10 | 10 | 10 | 10 |
| Isethionate | 15 | 10 | 15 | 10 | 15 | 15 | 15 | 10 | 10 |
| Ethanol | 34 | 39 | 39 | 39 | 34 | 35 | 30 | 38 | 37 |
| Urea | 15 | 15 | 15 | 15 | 15 | 15 | 15 | 15 | 15 |
| Water | 11 | 11 | 11 | 11 | 11 | 10 | 10 | 10 | 11 |
| Octyl trimethyl-ammonium bromide | 5 | 5 | | | | | | 5 | 5 |
| Tween 80 | | | | 5 | 5 | | 5 | | 5 |
| Tween 20 | | | | | | 5 | | | |
| HPC HY117 | | | | | | | | 2 | |
| PVP 30 | | | | | | | | | 2 |
| Ammonium thioglycolate (60% aqueous solution) | 10 | 10 | 10 | 10 | 10 | 10 | 10 | 10 | 10 |

Table 76 FVIII-C = F147-B
Table 76 FIX-C = F149-B

The data confirms the results of previous studies on behaviors of cationic and non-ionic detergents in ATG/isethionate formulations.

Figure 40A:
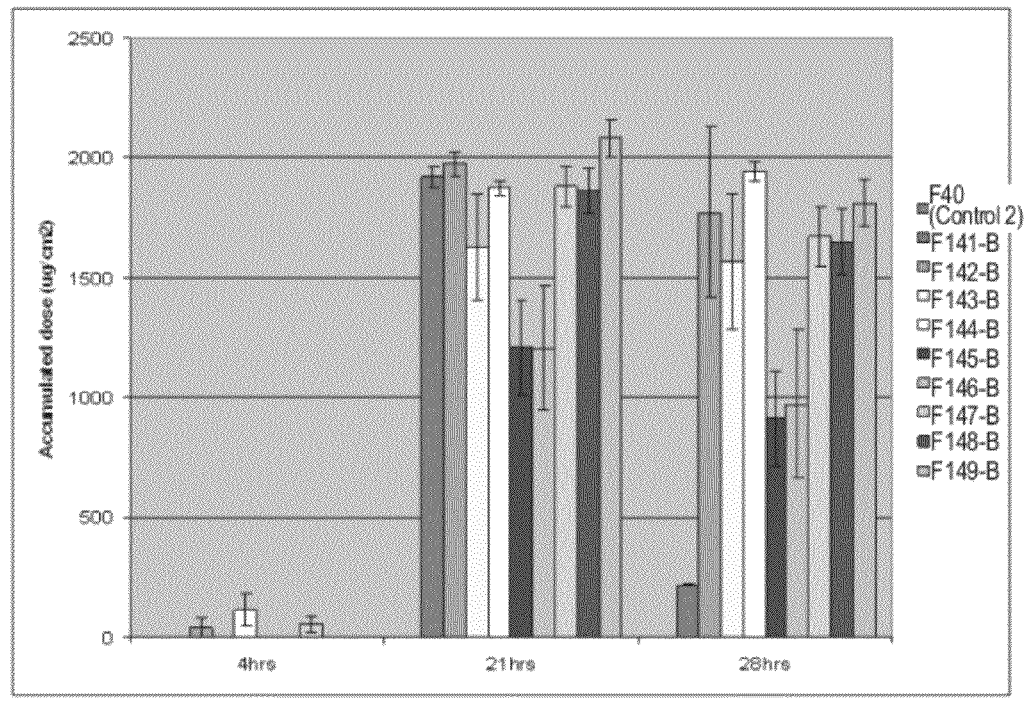
FIGS. 40A-B illustrate the results of shed snakeskin permeation studies on Formulations VI-C (Table 65).
Figure 40B:
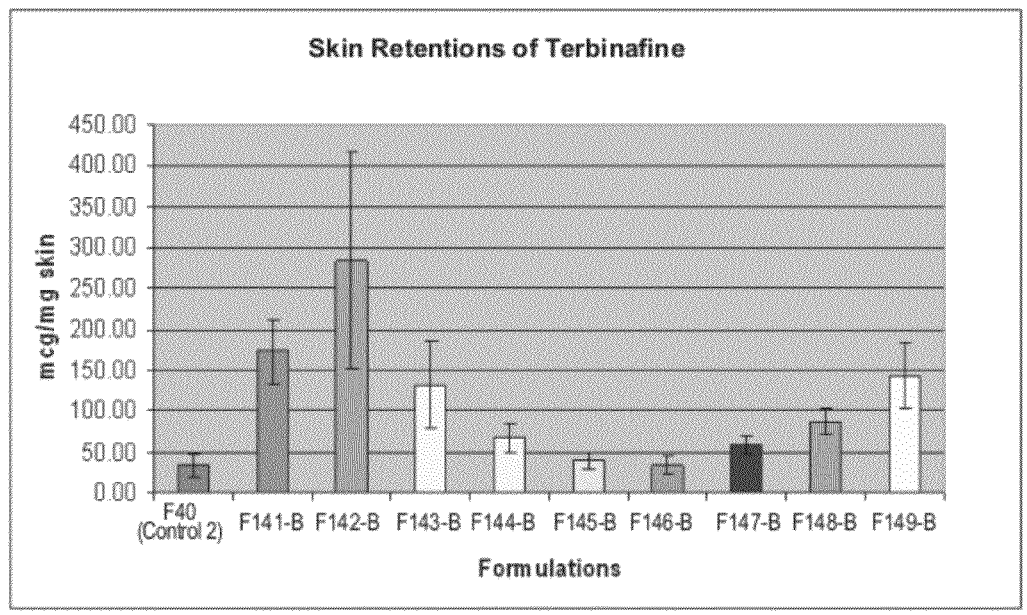

FIGS. 40A and 40B illustrate the results of transdermal studies on Formulations VI-C. FIG. 40A shows the permeation of active ingredient over time; FIG. 40B shows the total amount of active ingredient as a skin retention value.

Example 39

Terbinafine Formulations VII-C

TABLE 66

Terbinafine Formulations VII-C

| Ingredients | Formulations VII-C | | | | | | | | |
|---|---|---|---|---|---|---|---|---|---|
| | F151-B | F152-B | F153-B | F154-B | F155-B | F156-B | F157-B | F158-B | F159-B |
| Terbinafine HCl | 10 | 10 | 10 | 10 | 10 | 10 | 10 | 10 | 10 |
| Isethionate | | | | | | 10 | 10 | 10 | |
| Ethanol | 15 | 15 | 40 | 32.5 | 40 | 42.5 | 45 | 20 | 31 |
| Urea | | 15 | 15 | 15 | 15 | 15 | 15 | 15 | 15 |
| Water | 20 | 20 | 20 | 10 | 10 | 7.5 | 10 | 10 | 10 |
| DMSO | 55 | 40 | 15 | 32.5 | 15 | 5 | | 15 | 15 |
| Propylene glycol | | | | | | | | 20 | 20 |
| Ammonium thioglycolate (60% aqueous solution) | | | | | 10 | 10 | 10 | | |

Formulations with DMSO, urea, and additional solvents do not increase the permeation of terbinafine (F158-B, F159-B) versus a thioglycolate based formulation (F157-B). A DMSO/thioglycolate formulation had lower permeation (F156-B vs. F157-B).

Figure 41A:
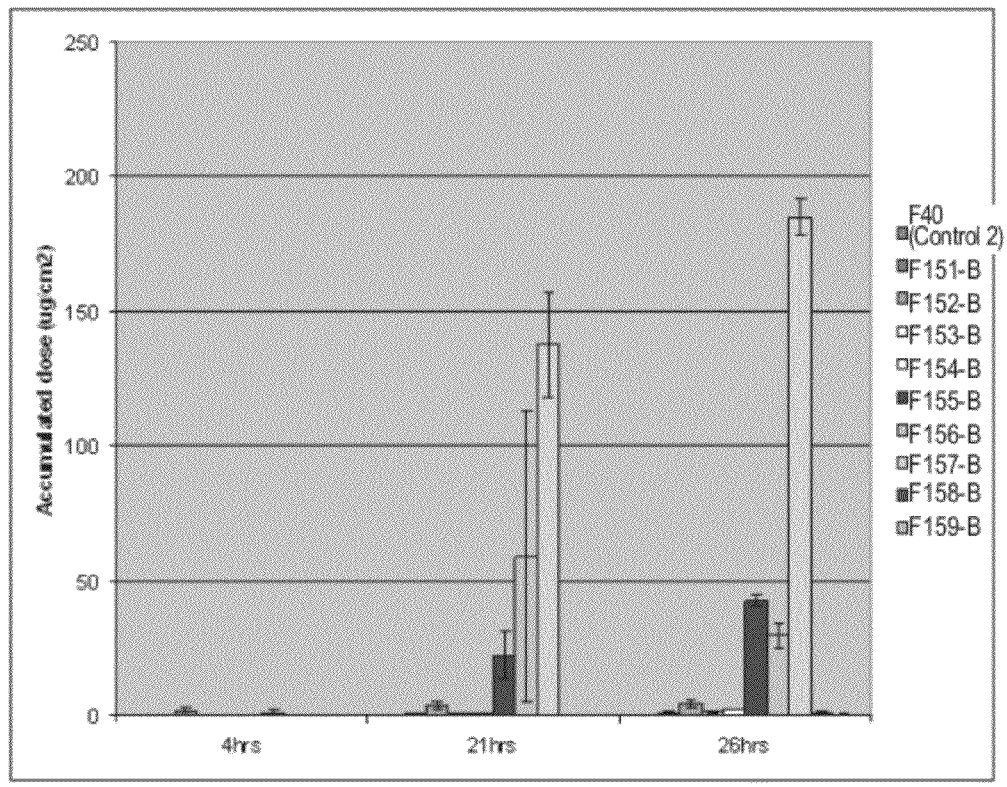
FIGS. 41A-B illustrate the results of shed snakeskin permeation studies on Formulations VII-C (Table 66).
Figure 41B:
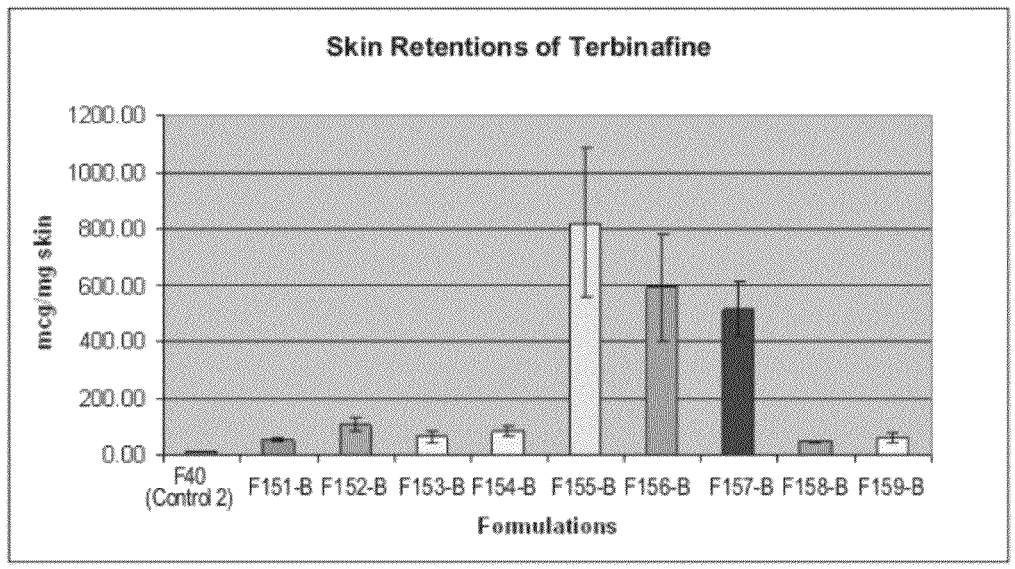

FIGS. 41A and 41B illustrate the results of transdermal studies on Formulations VII-C. FIG. 41A shows the permeation of active ingredient over time; FIG. 41B shows the total amount of active ingredient as a skin retention value.

Example 40

Terbinafine Formulations VIII-C

TABLE 67

Terbinafine Formulations VIII-C

| Ingredients | F161-B | F162-B | F163-B | F164-B | F165-B | F166-B | F167-B | F168-B | F169-B |
|---|---|---|---|---|---|---|---|---|---|
| Terbinafine HCl | 10 | 10 | 10 | 10 | 10 | 10 | 10 | 10 | 10 |
| Na isethionate | 10 | 5 | 10 | 5 | 10 | 10 | 5 | 10 | 10 |
| Ethanol | 48 | 53 | 45 | 50 | 45 | 39 | 44 | 43 | 43 |
| Urea | 10 | 10 | 10 | 10 | 10 | 10 | 10 | 10 | 10 |
| Water | 12 | 12 | 12 | 12 | 12 | 12 | 12 | 12 | 12 |
| Ammonium-thioglycolate (60% aqueous solution) | 10 | 10 | 10 | 10 | 10 | 10 | 10 | 10 | 10 |
| Tween 20 | | | 3 | 3 | | 9 | 9 | 3 | 3 |
| Tween 80 | | | | | 3 | | | | |
| HPC HY117 | | | | | | | | 2 | |
| Eudragit L100 | | | | | | | | | 2 |

Table 76 FX-C = F163-B
Table 76 FXI-C = F164-B
Table 76 FXII-C = F165-B
Table 76 FXIII-C = F168-B The reduction of isethionate levels reduces the permeation (F162-B vs. F161-B). However, addition of non-ionic surfactants restores the permeation (F162-B vs. F164-B). The results suggest that in Tween-containing formulations, the isethionate amount can be reduced. Thickeners can also be incorporated without a loss of activity.

Figure 42A:
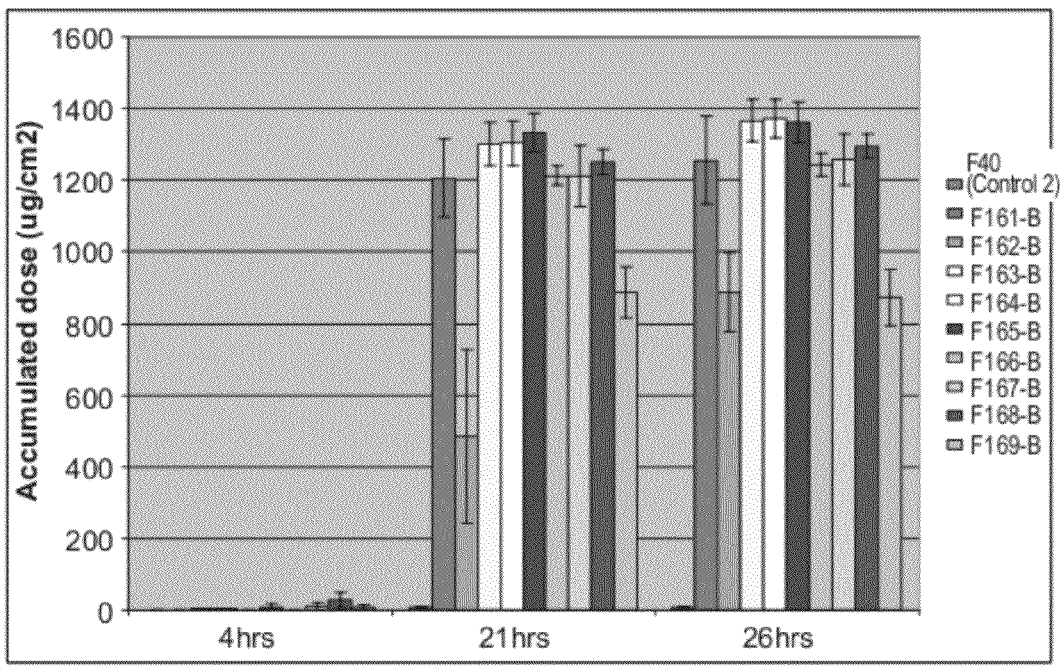
FIGS. 42A-B illustrate the results of shed snakeskin permeation studies on Formulations VIII-C (Table 67).
Figure 42B:
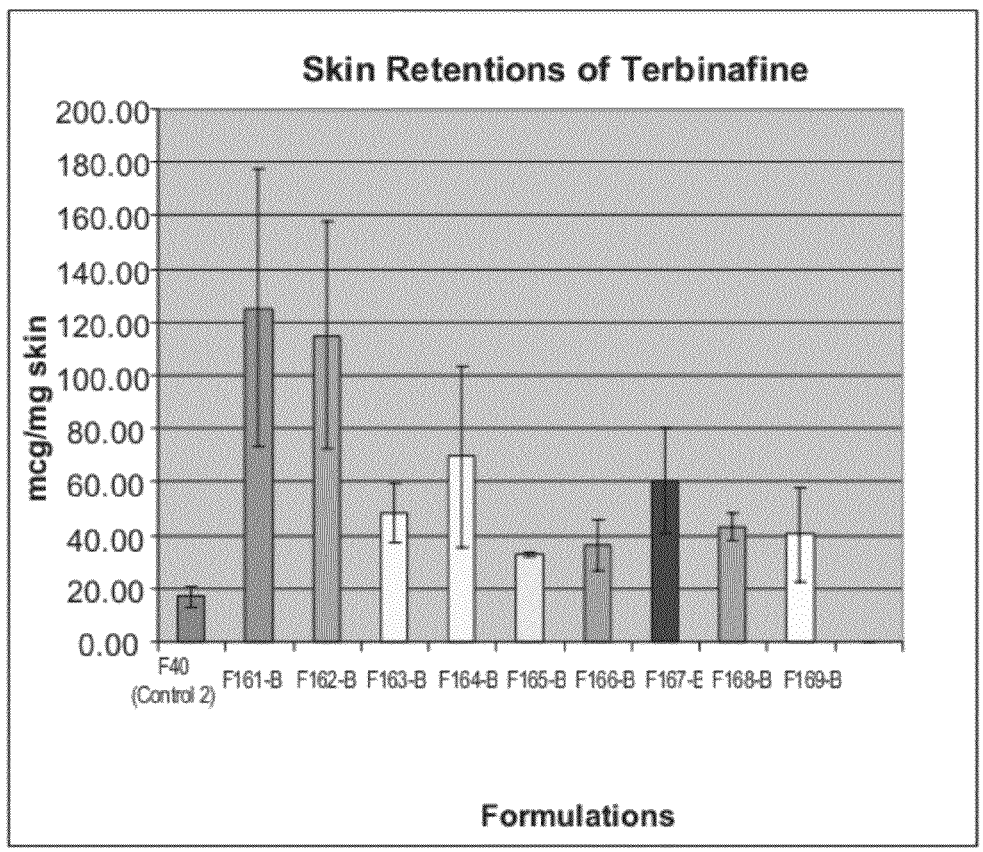

FIGS. 42A and 42B illustrate the results of transdermal studies on Formulations VIII-C. FIG. 42A shows the permeation of active ingredient over time; FIG. 42B shows the total amount of active ingredient as a skin retention value.

Example 41

Terbinafine Formulations IX-C

TABLE 68

Terbinafine Formulations IX-C

| Ingredients | F171-B | F172-B | F173-B | F174-B | F175-B | F176-B | F177-B | F178-B | F179-B |
|---|---|---|---|---|---|---|---|---|---|
| Terbinafine HCl | 10 | 10 | 10 | 10 | 10 | 10 | 10 | 10 | 10 |
| Ethanol | 47 | 39 | 42 | 38 | 53 | 45 | 48 | 44 | 39 |
| Water | 16 | 20 | 16 | 16 | 16 | 20 | 16 | 16 | 20 |
| Na isethionate | 5 | 5 | 10 | 10 | 5 | 5 | 10 | 10 | 5 |
| Urea | 10 | 10 | 10 | 10 | 10 | 10 | 10 | 10 | 10 |
| Tween 20 | 9 | 9 | 9 | 9 | 3 | 3 | 3 | 3 | |
| Lactic acid | | 4 | | 4 | | 4 | | 4 | 4 |
| Tween 80 | | | | | | | | | 9 |
| Glycerin mono laurate | 3 | 3 | 3 | 3 | 3 | 3 | 3 | 3 | 3 |

Table 76 FXIV-C = F176-B

The formulations without thioglycolate, but with isethionate and other ingredients show some permeation (F176-B).

Figure 43:
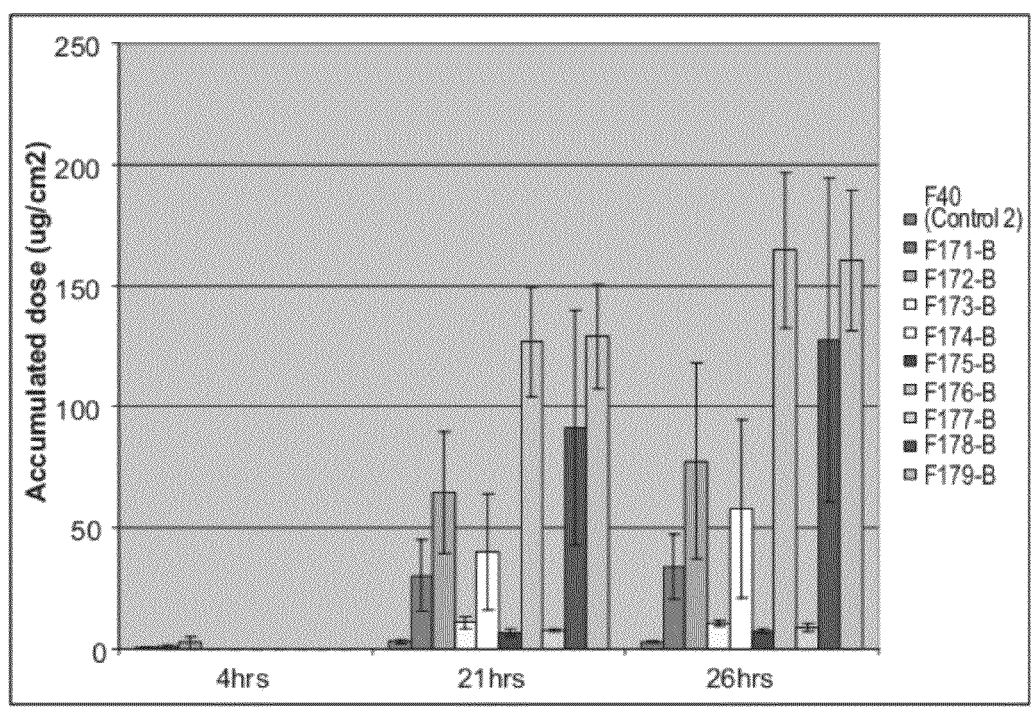
FIG. 43 illustrates the results of shed snakeskin permeation studies on Formulations IX-C (Table 68).

FIG. 43 illustrate the results of transdermal studies on Formulations IX-C. FIG. 43 shows the permeation of active ingredient over time.

Example 42

Terbinafine Formulations X-C

TABLE 69

Terbinafine Formulations X-C

| Ingredients | Formulations X-C | | | | |
|---|---|---|---|---|---|
| | F181-B | F182-B | F183-B | F184-B | F40 |
| | Part A | Part A | | | |
| Terbinafine HCl | 10 | 10 | 10 | 10 | Control 2 |
| Isethionate | 10 | | 10 | | |
| Ethanol | 40 | 42 | 41 | 45 | |
| Lactic acid | 4 | 4 | 5 | 5 | |
| Menthol | | 3 | | 3 | |
| Urea | 10 | 10 | 12 | 15 | |
| Water | 10 | 7 | | | |
| Eudragit L-100 | 2 | 2 | 2 | 2 | |
| Carnitine | | 5 | | 5 | |
| Acetyl carnitine | | 5 | | 5 | |
| | Part B | Part B | | | |
| Ammonium thio-glycolate (60% aqueous solution) | 10 | 10 | 10 | 10 | |
| Water | 7 | 7 | | | |
| Lactic acid | 1 | 1 | | | |
| Xanthan gum | 0.5 | 0.5 | | | |

Table 76 FXV-C = F181-B
Table 76 FXVI-C = F183-B

To enhance the stability of ammonium thioglycolate (reducing the color formation), thioglycolate based formulations were divided into two components: (a) with active and (b) with thioglycolate gel and xanthan gum. When compared to undivided formulations, they exhibited similarity; no color change, however, was observed.

Figure 44A:
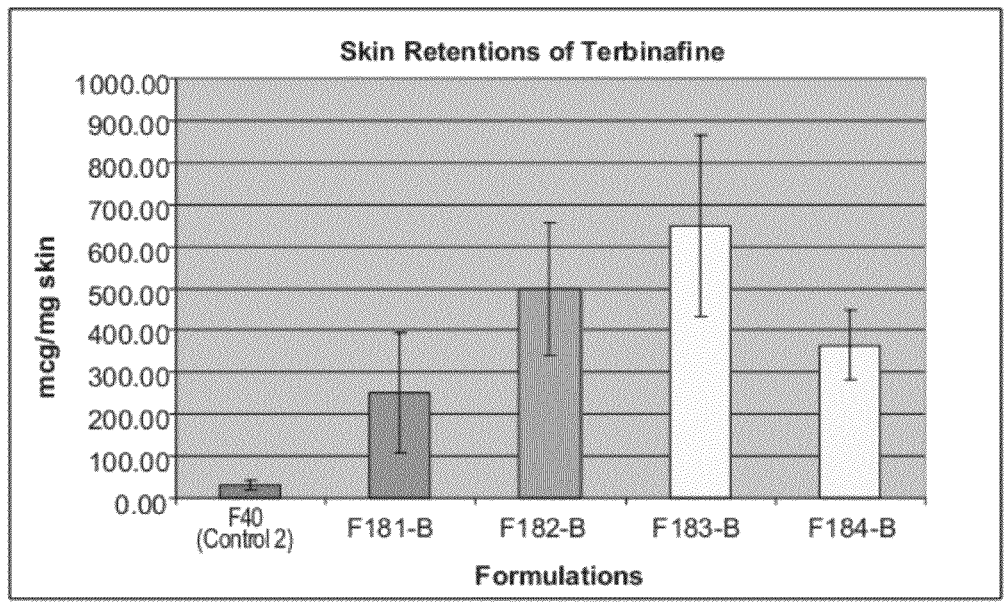
FIGS. 44A-B illustrate the results of shed snakeskin permeation studies on Formulations X-C (Table 69).
Figure 44B:
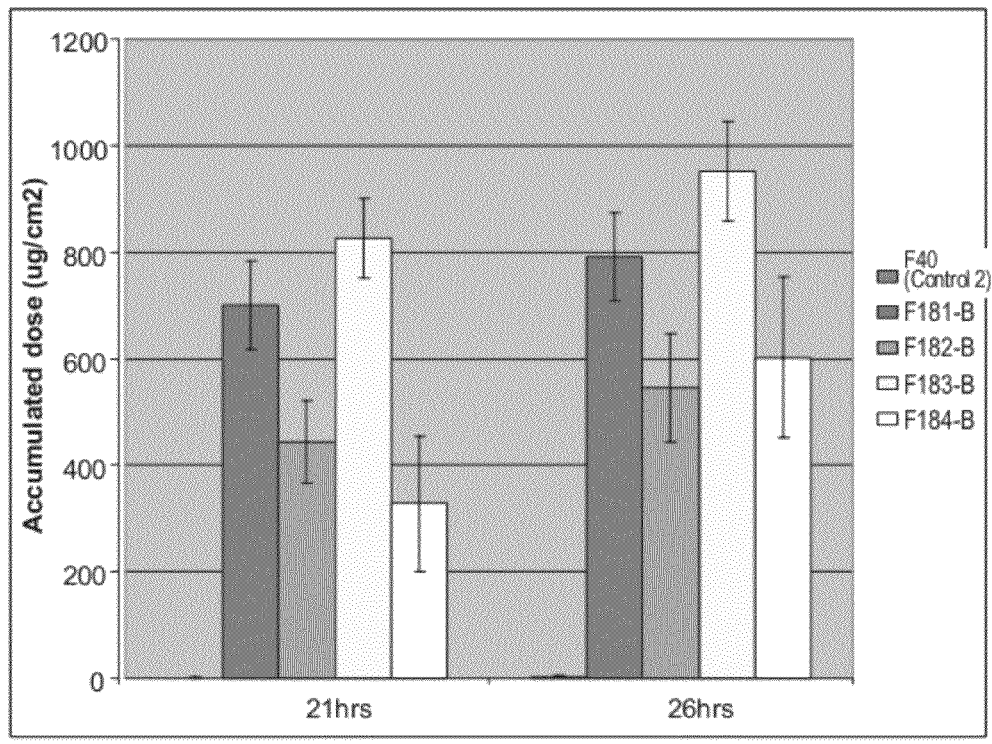

FIGS. 44A and 44B illustrate the results of transdermal studies on Formulations X-C. FIG. 44A shows the total amount of active ingredient as a skin retention value; FIG. 44B shows the permeation of active ingredient over time.

Example 43

Permeation of Terbinafine Through Bovine Hoof XI-C

TABLE 70

Permeation of Terbinafine Through Bovine Hoof XI-C

| Ingredients | Formulations XI-C | | | |
|---|---|---|---|---|
| | F191-B | F192-B | F24 | F40 |
| Terbinafine HCl | 10 | 10 | Control 1 | Control 2 |
| Isethionate | 10 | 10 | | |
| Ethanol | 42 | 40 | | |
| Urea | 15 | 15 | | |
| Water | 13 | 13 | | |
| Ammonium thio-glycolate (60% aqueous solution) | 10 | 10 | | |
| HPC (HY117) | | 2 | | |

Table 76 FIV-C = F191-B
Table 76 FIV-C w/thickener = F192-B

Incorporation of thickener into the thioglycolate formulation slightly enhances the delivery of terbinafine through bovine hoof.

Figure 45:
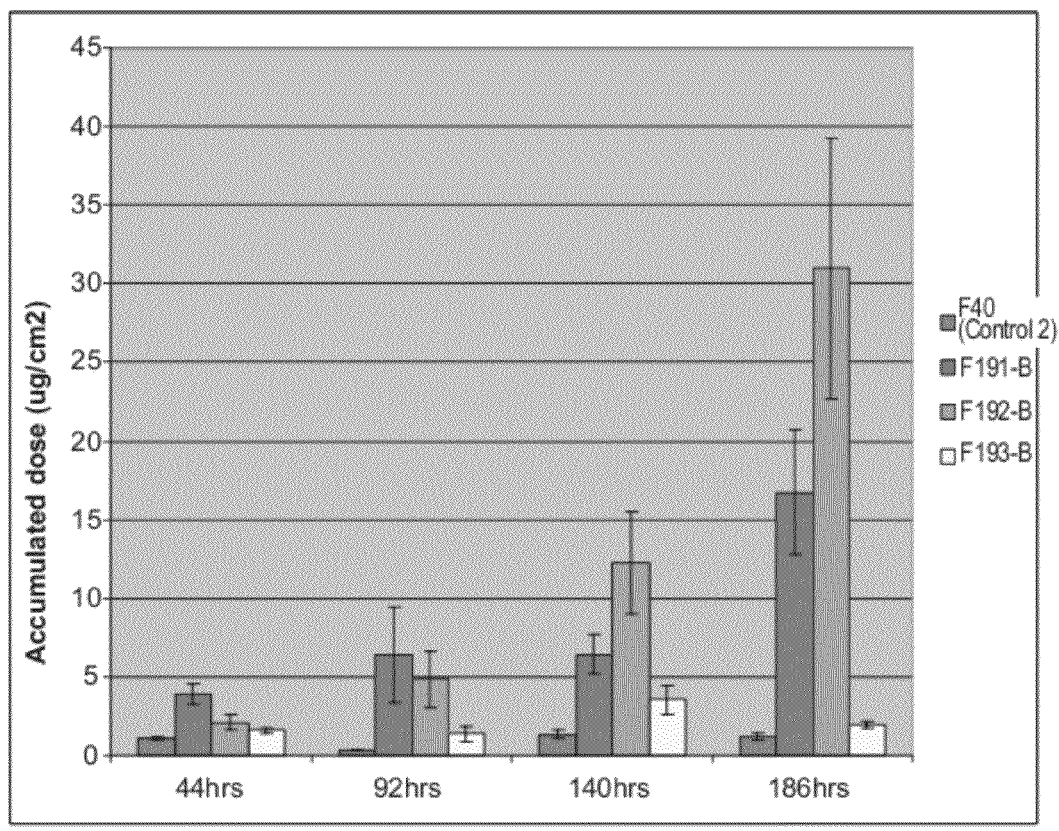
FIG. 45 illustrates the results of shed snakeskin permeation studies on Formulations XI-C (Table 70).

FIG. 45 illustrate the results of transdermal studies on Formulations XI-C. FIG. 45 shows the permeation of active ingredient over time.

Example 44

Terbinafine Nail Clipping Absorption Studies XII-C

TABLE 71

Terbinafine Nail Clipping Absorption Studies XII-C

| Ingredients | Formulations XII-C | | |
|---|---|---|---|
| | F201-B | F202-B | F24 |
| Terbinafine HCl | 10 | 10 | Control 1 |
| Sodium isethionate | 10 | 10 | |
| Ethanol | 40 | 46 | |
| Urea | 15 | 10 | |
| Water | 13 | 12 | |
| Ammonium thio-glycolate (60% aqueous solution) | 10 | 10 | |
| HPC (HY117) | 2 | 2 | |

Table 76 FIV w/thickener = F201-B
Table 75 FXVII-C w/thickener = F202-B

Time-dependent nail retentions from thickener containing thioglycolate formulations is much higher than the control formulation even after 2-4 hours.

Figure 46A:
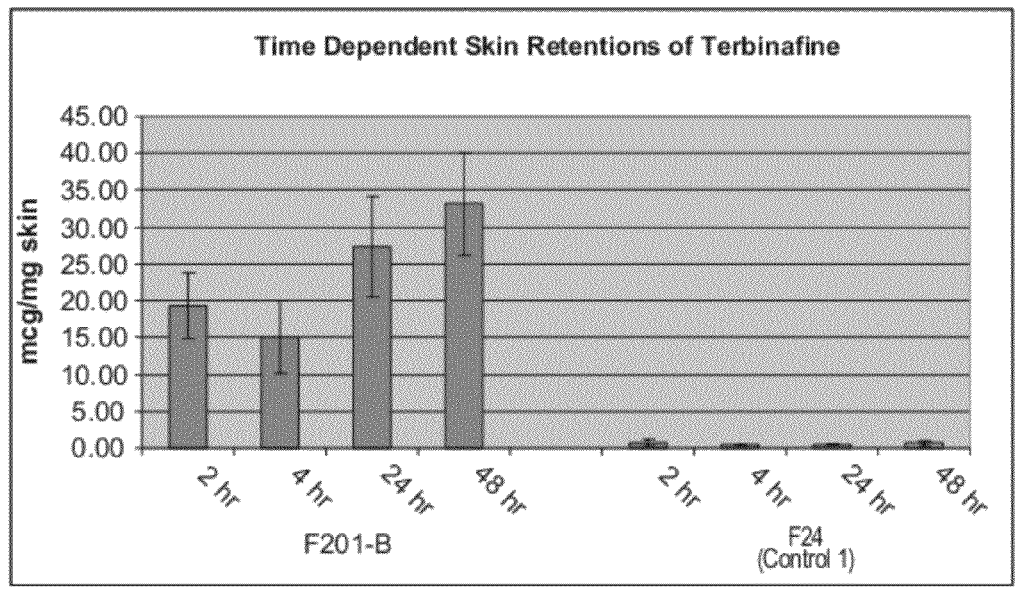
FIGS. 46A-B illustrate the results of shed snakeskin permeation studies on Formulations XII-C (Table 71).
Figure 46B:
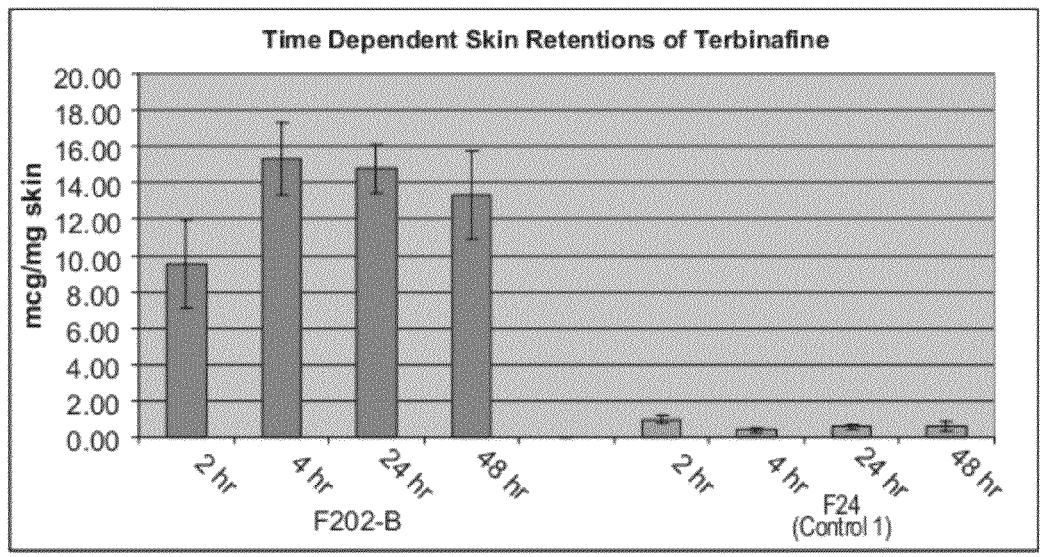

FIGS. 46A and 46B illustrate the results of transdermal studies on Formulations XII-C. FIGS. 46A-B show the permeation of active ingredient over time versus commercial formulations.

Example 45

Terbinafine Permeation Through Human Cadaver Nail XIII-C

TABLE 72

Terbinafine Permeation Through Human Cadaver Nail XIII-C

| Ingredients | Formulations XIII-C | |
|---|---|---|
| | F211-B | F24 |
| Terbinafine HCl | 10 | Control 1 |
| Na isethionate | 10 | |
| Ethanol | 40 | |
| Urea | 15 | |
| Water | 13 | |
| Ammonium thio-glycolate (60% aqueous solution) | 10 | |
| HPC (HY117) | 2 | |

Table 76 FXVII-C = F211-B

Thickener-containing thioglycolate formulation shows higher permeation and retentions than the control formulation.

Figure 47A:
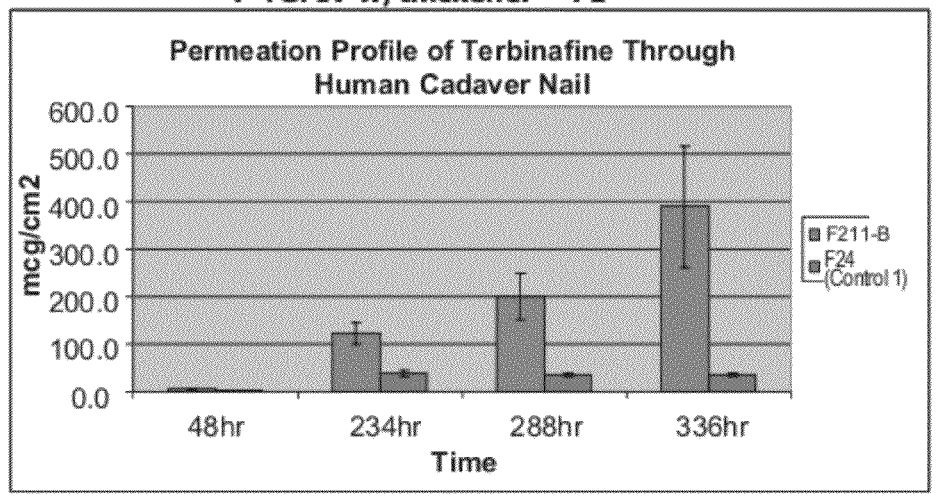
FIGS. 47A-D illustrate the results of human cadaver nail permeation studies on Formulations XIII-C (Table 72).
Figure 47B:
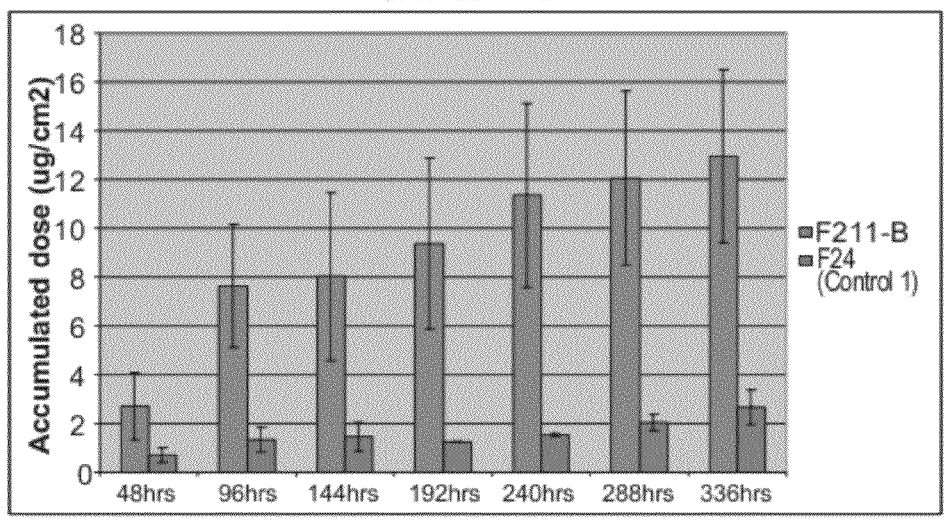
Figure 47C:
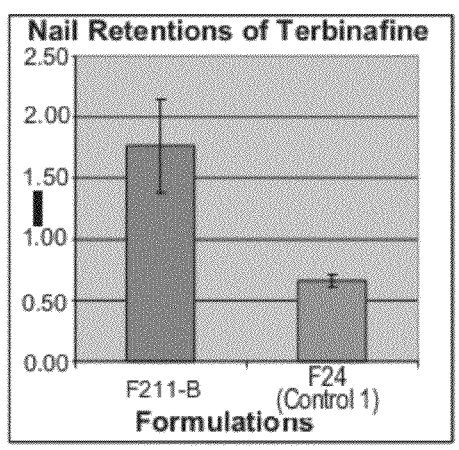
Figure 47D:
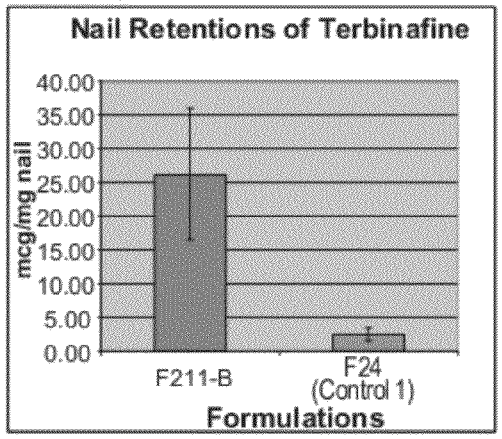

FIGS. 47A-D illustrate the results of transdermal studies on Formulations XIII-C. FIG. 47A shows the permeation of active ingredient over time with finite dose; FIG. 47C shows the total amount of active ingredient as a skin retention value. FIG. 47B shows the permeation of active ingredient over time with infinite dose; FIG. 47D shows the total amount of active ingredient as a skin retention value.

Example 46

Terbinafine Permeation Through Human Cadaver Nail XIV-C

TABLE 73

Terbinafine Permeation Through Human Cadaver Nail XIV-C

| Ingredients | Formulations-XIV-C | |
|---|---|---|
| | F221-B | F40 |
| Terbinafine HCl | 10 | Control 2 |
| Na isethionate | 10 | |
| Ethanol | 46 | |
| Urea | 10 | |
| Water | 12 | |
| Ammonium thio-glycolate (60% aqueous solution) | 10 | |
| HPC (HY117) | 2 | |

Table 76 FXVII-C = F221-B

At finite dosing, human nail retention and permeation from a thickener- and thioglycolate-containing formulation is also higher than Control 2.

Figure 48A:
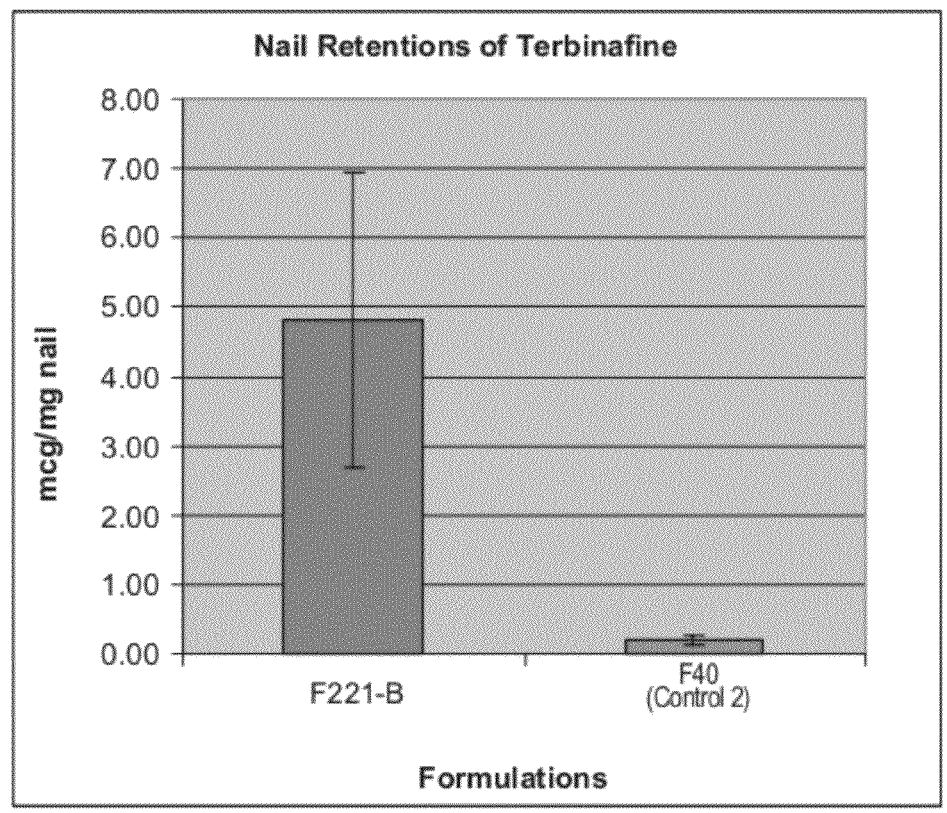
FIGS. 48A-B illustrate the results of human cadaver nail permeation studies on Formulations XIV-C (Table 73).
Figure 48B:
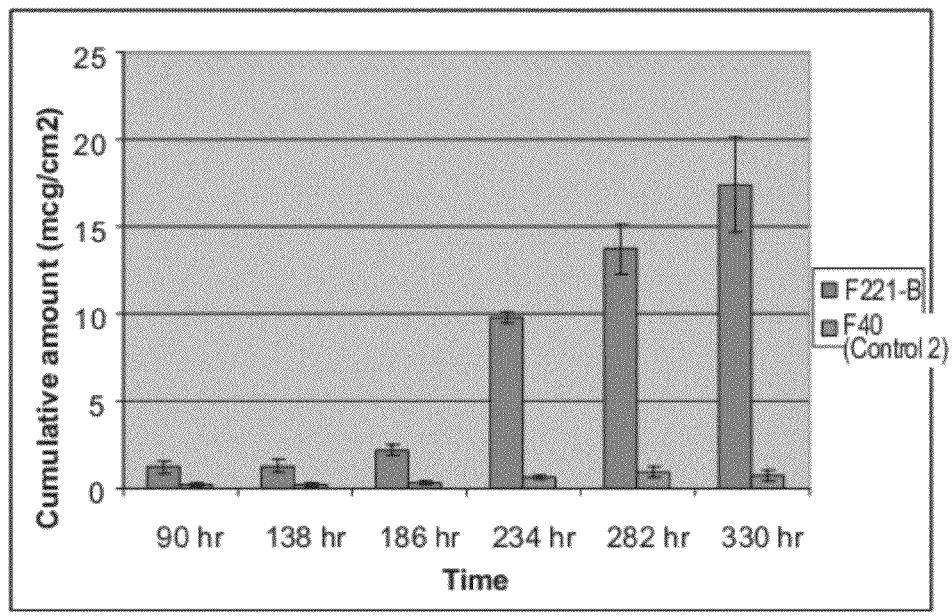

FIGS. 48A and 48B illustrate the results of transdermal studies on Formulations XIV-C. FIG. 48A shows the total amount of active ingredient as a skin retention value; FIG. 48B shows the permeation of active ingredient over time.

Example 47

Terbinafine-Bovine Hoof Permeation XV-C

TABLE 74

Terbinafine-Bovine Hoof Permeation XV-C

| Ingredients | Formulations-XV-C | | |
|---|---|---|---|
| | F231-B | F232-B | F40 |
| Terbinafine HCl | 10 | 10 | Control 2 |
| Ethanol | 32.5 | | |

TABLE 74-continued

Terbinafine-Bovine Hoof Permeation XV-C

| Ingredients | Formulations-XV-C | | |
|---|---|---|---|
| | F231-B | F232-B | F40 |
| Ethyl acetate | 15 | | |
| Disodium cocoamphodiacetate | 10 | | |
| Water | 12.5 | | |
| Lactic acid | 5 | | |
| Urea | 10 | | |
| Menthol | 5 | | |
| Na isethionate | | 10 | |
| Ethanol | | 46 | |
| Urea | | 10 | |
| Water | | 12 | |
| Ammonium thio-glycolate (60% aqueous solution) | | 10 | |
| HPC (HY117) | | 2 | |

Table 76 FXVII-C = F232-B

Figure 49A:
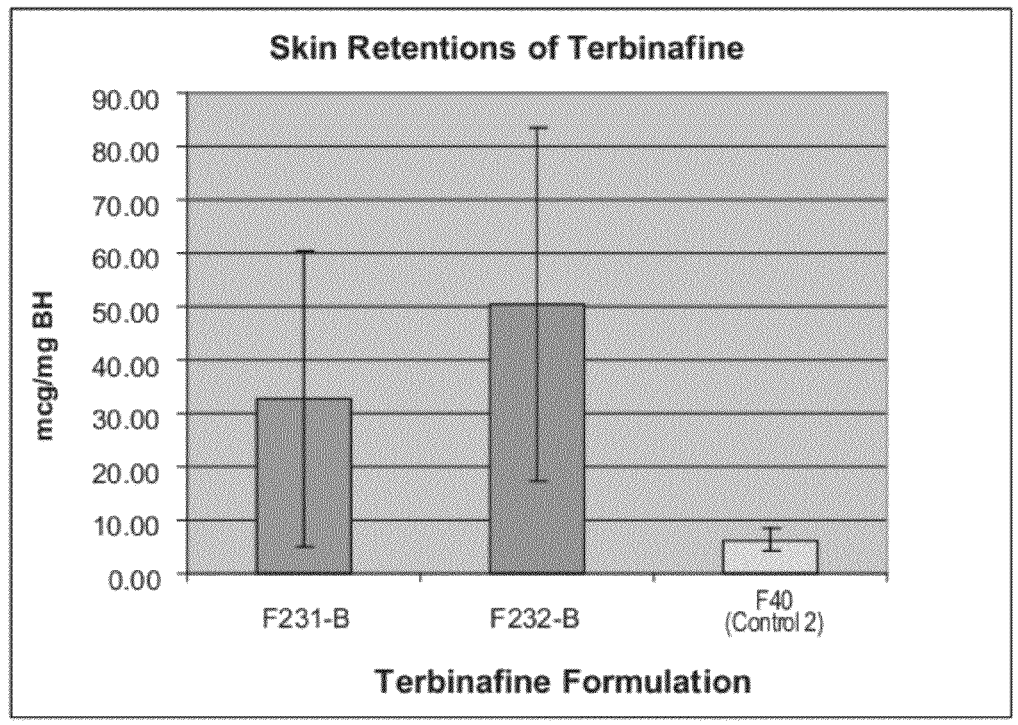
FIGS. 49A-B illustrate the results of shed snakeskin permeation studies on Formulations XV-C versus the prior art formulation of Control 2 (Table 74).
Figure 49B:
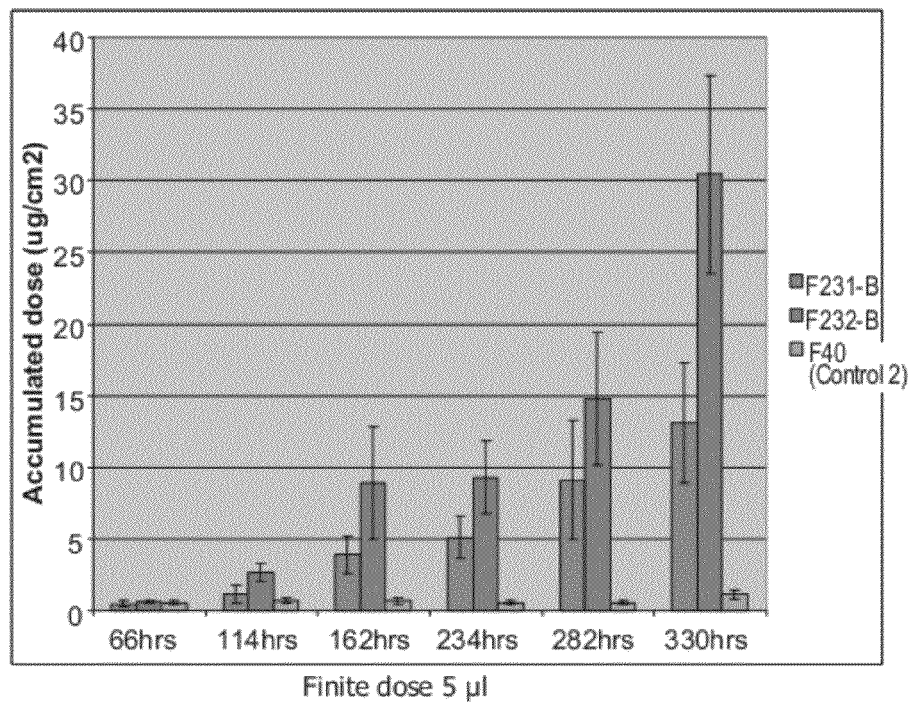

FIGS. 49A and 49B illustrate the results of transdermal studies on the formulations of Table 73. FIG. 49A shows the total amount of active ingredient as a skin retention value; FIG. 49B shows the permeation of active ingredient over time.

When compared to Control 2 (F40; Lamisil®), both disodium cocoamphodiacetate and ammonium thioglycolate ("ATG") formulations show higher permeation enhancement through the bovine hoof ATG formulation has somewhat higher permeation (~2×) at long term. At early hours, permeation differences are not significant.

Example 48

ATG/Carnitines Chassis Formulations

TABLE 75

ATG/Carnitines Chassis Formulations

| Ingredients | ATG/Carnitines Chassis Formulations | | | | | | |
|---|---|---|---|---|---|---|---|
| | FI-B | FII-B | FIII-B | FIV-B | FV-B | FVI-B | FVII-B |
| Terbinafine HCl | 10 | 10 | 10 | 10 | 10 | 10 | 10 |
| Ethanol | 55 | 42 | 45 | 45 | 45 | 43 | 43 |
| Water | 10 | 8 | 10 | 10 | 10 | 10 | 10 |
| Urea | | 15 | | | | | |
| Carnitine | 7.5 | 7.5 | 7.5 | 7.5 | 7.5 | 7.5 | 7.5 |
| Acetyl carnitine | 7.5 | 7.5 | 7.5 | 7.5 | 7.5 | 7.5 | 7.5 |
| Menthol | | | 5 | 5 | | 5 | 5 |
| Ammonium thioglycolate (60% aqueous solution) | 10 | 10 | 10 | 10 | 10 | 10 | 10 |
| Lactic acid | | | 5 | | 5 | 5 | 5 |
| Acetic acid | | | | 5 | | | |
| Phenol | | | | | 5 | | |
| HPC HY117 | | | | | | 2 | |
| PVP-30 | | | | | | | 2 |
| Eudragit L100 | | | | | | | |

TABLE 75-continued

| ATG/Carnitines Chassis Formulations |
|---|

Xanthan gum
Glycerin mono laurate

| | ATG/Carnitines Chassis Formulations II | | | | | |
|---|---|---|---|---|---|---|
| Ingredients | FVIII-B | FIX-B* | FX-B** | FXI-B | FXII-B | FXIII-B |
| Terbinafine HCl | 10 | 10 | 10 | 10 | 10 | 10 |
| Ethanol | 43 | 42 | 42 | 60 | 55 | 57 |
| Water | 10 | 17 | 17 | 15 | 15 | 15 |
| Urea | | | | | 5 | |
| Carnitine | 7.5 | 5 | 5 | 5 | 5 | 5 |
| Acetyl carnitine | 7.5 | 5 | 5 | 5 | 5 | 5 |
| Menthol | 5 | 3 | 3 | | | |
| Ammonium thioglycolate (60% aqueous solution) | 10 | 10 | 10 | | | |
| Lactic acid | 5 | 5 | 5 | 5 | 5 | 5 |
| Acetic acid | | | | | | |
| Phenol | | | | | | |
| HPC HY117 | | | | | | |
| PVP-30 | | | | | | |
| Eudragit L100 | 2 | 2 | 2 | | | |
| Xanthan gum | | 1 | 1 | | | |
| Glycerin mono laurate | | | | | | 3 |

\*, \*\*Formulations were divided into 2 components: (1) active; (2) ammonium thioglycolate (as part of 60% aqueous solution).
\*\*Formulation contains additional metabisulfite.

Unless otherwise stated, all exploratory experiments described herein were performed using shed snakeskin as the model membrane. Final studies were performed with bovine hoof and human cadaver nail.

In certain embodiments, the present invention provides a formulation comprising, consisting essentially of, or consisting of the components recited in Table 75 for each of the formulations listed. For example, the present invention provides a formulation I-B, comprising, consisting essentially of, or consisting of 10% terbinafine hydrochloride; 55% ethanol; 10% water; 7.5% carnitine; 7.5% acetyl carnitine; and 10% of a 60% aqueous solution of ammonium thioglycolate.

Example 49

ATG/Isethionate Chassis

TABLE 76

| ATG/Isethionate Chassis |
|---|

| | ATG/Isethionate Chassis Formulations | | | | | | | | |
|---|---|---|---|---|---|---|---|---|---|
| Ingredients | FI-C | FII-C | FIII-C | FIV-C | FV-C | FVI-C | FVII-C | FVIII-C | FIX-C |
| Terbinafine HCl | 10 | 10 | 10 | 10 | 10 | 10 | 10 | 10 | 10 |
| Ethanol | 40 | 40 | 39 | 42 | 37 | 39 | 39 | 30 | 37 |
| Water | 14 | 14 | 20 | 13 | 13 | 11 | 11 | 10 | 11 |
| DCAM | 15 | 15 | | | | | | | |
| Urea | 15 | 15 | 15 | 15 | 15 | 15 | 15 | 15 | 15 |
| Sodium isethionate | | | 10 | 10 | 10 | 10 | 10 | 15 | 10 |
| Potassium thioglycolate | 6 | | 6 | | | | | | |
| Ammonium thioglycolate (60% aqueous solution) | | 6 | | 10 | 10 | 10 | 10 | 10 | 10 |
| Tween 80 | | | | | 5 | | | 5 | 5 |
| Octyltrimethylammonium bromide | | | | | | 5 | | 5 | |
| Cetyltrimethylammonium bromide | | | | | | | 5 | | |
| PVP30 | | | | | | | | | 2 |
| Tween 20 | | | | | | | | | |
| HPC HY 117 | | | | | | | | | |
| Lactic acid | | | | | | | | | |
| Eudragit L100 | | | | | | | | | |
| Xanthan gum | | | | | | | | | |

TABLE 76-continued

ATG/Isethionate Chassis

ATG/Isethionate Chassis Formulations

| Ingredients | FI-C | FII-C | FIII-C | FIV-C | FV-C | FVI-C | FVII-C | FVIII-C | FIX-C |
|---|---|---|---|---|---|---|---|---|---|
| Glycerin mono laurate | | | | | | | | | |

*Formulations were divided into two components: (1) active; (2) ammonium thioglycolate (as part of 60% aqueous solution).

| | ATG/Isethionate Chassis Formulations | | | | | | | |
|---|---|---|---|---|---|---|---|---|
| Ingredients | FX-C | FXI-C | FXII-C | FXIII-C | FXIV-C | FXV-C* | FXVI-C | FXVII-C |
| Terbinafine HCl | 10 | 10 | 10 | 10 | 10 | 10 | 10 | 10 |
| Ethanol | 45 | 50 | 45 | 43 | 45 | 39.5 | 41 | 46 |
| Water | 12 | 12 | 12 | 12 | 20 | 13 | 12 | 12 |
| DCAM | | | | | | | | |
| Urea | 10 | 10 | 10 | 10 | 10 | 10 | 10 | 10 |
| Sodium isethionate | 10 | 5 | 10 | 10 | 5 | 10 | 10 | 10 |
| Potassium thioglycolate | | | | | | | | |
| Ammonium thioglycolate (60% aqueous solution) | 10 | 10 | 10 | 10 | | 10 | 10 | 10 |
| Tween 80 | | | 3 | 3 | | | | |
| Octyltrimethylammonium bromide | | | | | | | | |
| Cetyltrimethylammonium bromide | | | | | | | | |
| PVP30 | | | | | | | | |
| Tween 20 | 3 | 3 | | | 3 | | | |
| HPC HY 117 | | | | 2 | | | | 2 |
| Lactic acid | | | | | 4 | 5 | 5 | |
| Eudragit L100 | | | | | | 2 | 2 | |
| Xanthan gum | | | | | | 0.5 | | |
| Glycerin mono laurate | | | | | 3 | | | |

*Formulations were divided into two components: (1) active; (2) ammonium thioglycolate (as part of 60% aqueous solution).

In certain embodiments, the present invention provides a formulation comprising, consisting essentially of, or consisting of the components recited in Table 76 for each of the formulations listed. For example, the present invention provides a formulation I-C, comprising, consisting essentially of, or consisting of 10% terbinafine hydrochloride; 40% ethanol; 14% water; 15% DCAM; 15% urea; and 6% sodium thioglycolate.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A hydroalcoholic formulation for the treatment of onychomycosis, wherein the formulation comprises:
   2% to 20% (w/w) terbinafine or a salt thereof;
   a zwitterionic surfactant or a salt thereof, wherein the zwitterionic surfactant or the salt thereof is selected from the group consisting of a cocoamphodiacetate and a salt of cocoamphodiacetate;
   a carboxylic acid, wherein the acid is selected from the group consisting of acetic acid, lactic acid, tartaric acid, malic acid, succinic acid, glycolic acid, citric acid, caprylic acid, caproic acid, and a mixture thereof;
   at least 25% (w/w) of a lower alcohol; and
   water;
   wherein the formulation is suitable for topical administration to a nail.

2. The formulation of claim 1, wherein said terbinafine or the salt thereof is terbinafine hydrochloride.

3. The formulation of claim 1, wherein the formulation has about 5% to 20% (w/w) of terbinafine or the salt thereof.

4. The formulation of claim 1, wherein the formulation has from about 0.5% to 20% (w/w) of the zwitterionic surfactant or the salt thereof.

5. The formulation of claim 1, wherein the zwitterionic surfactant or a salt thereof is the salt of cocoamphodiacetate.

6. The formulation of claim 1, wherein the carboxylic acid is selected from the group consisting of acetic acid, lactic acid, tartaric acid, malic acid, glycolic acid, and citric acid.

7. The formulation of claim 6, wherein the formulation has from about 3% to 10% (w/w) of the carboxylic acid.

8. The formulation of claim 7, wherein the carboxylic acid is lactic acid.

9. The formulation of claim 1, wherein the formulation has from about 25% to 50% (w/w) of the lower alcohol.

10. The formulation of claim 1, wherein the lower alcohol is ethanol.

11. The formulation of claim 1, wherein the formulation further comprises a keratolytic agent or a triol.

12. The formulation of claim 1, wherein the formulation further comprises an ester solvent.

13. The formulation of claim 12, wherein the formulation has from about 1% to 25% (w/w) of the ester solvent.

14. The formulation of claim 12, wherein the ester solvent is ethyl acetate.

15. The formulation of claim 1, wherein the formulation further comprises a thickener.

16. The formulation of claim 15, wherein the thickener is hydroxypropyl cellulose.

17. The formulation of claim 15, wherein the formulation has about 0.5% to 5% (w/w) of the thickener.

18. The formulation of claim 1, wherein the formulation has a pH value between about 7 and 10.

19. A method for treating onychomycosis, the method comprising:
topically administering a composition of claim 1 to a patient with onychomycosis, thereby treating onychomycosis.

20. The formulation of claim 1, wherein the formulation has about 10% to 17% (w/w) of terbinafine or a salt thereof.

21. The formulation of claim 1, wherein the formulation has about 10% (w/w) of terbinafine or a salt thereof.

22. The formulation of claim 1, wherein the formulation has about 15% (w/w) of terbinafine or a salt thereof.

23. The formulation of claim 1, wherein the formulation has from about 10% to 20% (w/w) of the zwitterionic surfactant or the salt thereof.

24. The formulation of claim 1, wherein the formulation has about 10% w/w of the zwitterionic surfactant or the salt thereof.

25. The formulation of claim 1, wherein the formulation has from about 25% to 45% (w/w) of the lower alcohol.

26. The formulation of claim 12, wherein the formulation has from about 5% to 20% (w/w) of the ester solvent.

27. The formulation of claim 1, wherein the formulation has a pH value between about 3 and 7.

28. The formulation of claim 1, wherein the concentration of terbinafine in test nails treated with the formulation reaches at least 18 µg/mg after 336 h.

29. The formulation of claim 1, wherein the concentration of terbinafine in test nails treated with the formulation reaches at least 18.91±5.82 µg/cm² after 336 h compared to a control at 2.14±0.55 µg/cm².

30. The formulation of claim 1, wherein the formulation dries in from about 1 to about 15 minutes after its application to a nail.

31. A unit-dosage form, wherein the unit-dosage form contains the formulation of claim 1.

32. A hydroalcoholic formulation for the treatment of onychomycosis, wherein the formulation comprises:
1% to 20% (w/w) of terbinafine or a salt thereof;
0.5% to 20% (w/w) of a zwitterionic surfactant or a salt thereof, wherein the zwitterionic surfactant or the salt thereof is selected from the group consisting of a cocoamphodiacetate and a salt of cocoamphodiacetate;
3% to 10% (w/w) of a carboxylic acid, wherein the acid is selected from the group consisting of a short-chain hydroxy acid, a short-chain fatty acid, and a mixture thereof;
about 25% to 45% (w/w) of a lower alcohol; and
water;
wherein the formulation is suitable for topical administration to a nail.

33. The hydroalcoholic formulation of claim 32, wherein the formulation further comprises about 5% to 20% (w/w) of an ester solvent.

34. The hydroalcoholic formulation of claim 32, wherein the formulation further comprises about 0.5% to 5% (w/w) of a thickener.

35. The hydroalcoholic formulation of claim 32, wherein the formulation further comprises about 5% to 20% (w/w) of a keratolytic agent.

36. The formulation of claim 32, wherein the formulation has a pH value between about 3 and 7.

37. The formulation of claim 32, wherein the formulation has from about 0.5% to 5% (w/w) of the zwitterionic surfactant or the salt thereof.

38. The formulation of claim 5, wherein the salt of cocoamphodiacetate is disodium cocoamphodiacetate.

39. The method of claim 19, wherein the formulation is administered by transungual application.

40. The method of claim 19, wherein the formulation is topically administered to a nail and a surrounding tissue of the nail.

* * * * *